(12) United States Patent
Sholev et al.

(10) Patent No.: US 10,206,672 B2
(45) Date of Patent: Feb. 19, 2019

(54) ARTHROSCOPIC SURGICAL DEVICE

(71) Applicant: MININVASIVE LTD., Magal (IL)

(72) Inventors: Mordechai Sholev, Amikam (IL); Raphael Meloul, Caesarea (IL); Arnon Mousaiuf, Atlit (IL); Boaz Harari, Haifa (IL); Ronen Raz, Magal (IL)

(73) Assignee: MININVASIVE LTD., Magal (IL)

( * ) Notice: Subject to any disclaimer, the term of this patent is extended or adjusted under 35 U.S.C. 154(b) by 348 days.

(21) Appl. No.: 14/766,490

(22) PCT Filed: Mar. 18, 2014

(86) PCT No.: PCT/IL2014/050299
§ 371 (c)(1),
(2) Date: Aug. 7, 2015

(87) PCT Pub. No.: WO2014/147619
PCT Pub. Date: Sep. 25, 2014

(65) Prior Publication Data
US 2016/0015380 A1    Jan. 21, 2016

Related U.S. Application Data

(60) Provisional application No. 61/802,958, filed on Mar. 18, 2013, provisional application No. 61/887,561, filed on Oct. 7, 2013.

(51) Int. Cl.
*A61B 17/00*       (2006.01)
*A61B 17/04*       (2006.01)
(Continued)

(52) U.S. Cl.
CPC ...... *A61B 17/0469* (2013.01); *A61B 17/0482* (2013.01); *A61B 17/0485* (2013.01);
(Continued)

(58) Field of Classification Search
CPC combination set(s) only.
See application file for complete search history.

(56) References Cited

U.S. PATENT DOCUMENTS 2,579,192 A   12/1951   Kohl
5,250,055 A   10/1993   Moore et al.
(Continued)

FOREIGN PATENT DOCUMENTS

CN   101193600   9/2010
EP   1898812     3/2008
(Continued)

OTHER PUBLICATIONS

European Search Report dated May 11, 2017, which issued during the prosecution of Applicant's European App No. 11806391.6.
(Continued)

*Primary Examiner* — Sameh Boles
(74) *Attorney, Agent, or Firm* — Sughrue Mion, PLLC

(57) ABSTRACT

An arthroscopic bone channel forming and suturing method including forming a first generally straight channel in a bone, forming a second generally straight channel in the bone, the second generally straight channel not intersecting the first generally straight channel, inserting a curved needle into the first generally straight channel, inserting a suture through the second generally straight channel in the bone to a suture pick-up location, manipulating the curved needle to form a curved junction between the first generally straight channel and the second generally straight channel; and pulling the suture by the curved needle from the suture pick-up location through the junction and though the first generally straight channel.

8 Claims, 76 Drawing Sheets

(51) Int. Cl.
- *A61B 17/062* (2006.01)
- *A61B 17/16* (2006.01)
- *A61B 17/06* (2006.01)
- *A61B 90/00* (2016.01)

(52) U.S. Cl.
CPC ...... *A61B 17/062* (2013.01); *A61B 17/06066* (2013.01); *A61B 17/06166* (2013.01); *A61B 17/1604* (2013.01); *A61B 17/1615* (2013.01); *A61B 2017/00349* (2013.01); *A61B 2017/00353* (2013.01); *A61B 2090/0811* (2016.02)

(56) References Cited

U.S. PATENT DOCUMENTS

| | | |
|---|---|---|
| 5,387,221 A | 2/1995 | Bisgaard |
| 5,499,991 A | 3/1996 | Garman et al. |
| 5,665,096 A | 9/1997 | Yoon |
| 5,681,333 A | 10/1997 | Burkhart et al. |
| 5,961,530 A | 10/1999 | Moore |
| 6,328,744 B1 | 12/2001 | Harari |
| 6,443,963 B1 | 9/2002 | Baldwin |
| 6,523,417 B1 | 2/2003 | Donahue |
| 7,029,479 B2 | 4/2006 | Tallarida |
| 7,097,648 B1 | 8/2006 | Globerman et al. |
| 7,166,116 B2 | 1/2007 | Lizardi et al. |
| 7,662,171 B2 | 2/2010 | West, Jr. |
| 8,088,130 B2 | 1/2012 | Kaiser et al. |
| 8,282,657 B2 | 10/2012 | McClurg et al. |
| 2002/0040227 A1 | 4/2002 | Harari |
| 2003/0078599 A1 | 4/2003 | O'Quinn |
| 2006/0195121 A1 | 8/2006 | Chu |
| 2006/0271060 A1 | 11/2006 | Gordon |
| 2007/0005067 A1 | 1/2007 | Dross |
| 2007/0179509 A1 | 8/2007 | Nagata et al. |
| 2008/0109015 A1 | 5/2008 | Chu et al. |
| 2008/0228224 A1 | 9/2008 | Sauer |
| 2009/0012538 A1 | 1/2009 | Saliman et al. |
| 2009/0062819 A1 | 3/2009 | Burkhart |
| 2009/0069823 A1 | 3/2009 | Foerster |
| 2009/0105729 A1 | 4/2009 | Zentgraf |
| 2009/0105743 A1 | 4/2009 | Chu |
| 2009/0131956 A1 | 5/2009 | Dewey |
| 2009/0138029 A1 | 5/2009 | Saliman et al. |
| 2009/0157076 A1 | 6/2009 | Athas et al. |
| 2009/0206128 A1 | 8/2009 | Hueil et al. |
| 2009/0270862 A1 | 10/2009 | Arcenio |
| 2009/0312782 A1 | 12/2009 | Park |
| 2010/0076436 A1 | 3/2010 | Hajianpour |
| 2010/0106194 A1 | 4/2010 | Bonutti et al. |
| 2010/0152751 A1 | 6/2010 | Meade et al. |
| 2010/0191248 A1 | 7/2010 | Mehta et al. |
| 2010/0198258 A1 | 8/2010 | Heaven et al. |
| 2010/0318139 A1 | 12/2010 | Beauchamp |
| 2011/0022063 A1 | 1/2011 | McClurg |
| 2011/0106124 A1 | 5/2011 | Beauchamp |
| 2012/0239085 A1 | 9/2012 | Schlotterback et al. |
| 2012/0323248 A1 | 12/2012 | Dross |
| 2013/0123810 A1 | 5/2013 | Brown et al. |
| 2013/0144337 A1 | 6/2013 | Stone et al. |
| 2013/0178854 A1 | 7/2013 | Sholev et al. |
| 2013/0296931 A1 | 11/2013 | Sengun |
| 2014/0214038 A1 | 7/2014 | Sholev |
| 2014/0303625 A1 | 10/2014 | Sholev |
| 2015/0045795 A1* | 2/2015 | Sholev ............... A61B 17/0469 606/79 |
| 2015/0258332 A1 | 9/2015 | Bentley et al. |
| 2015/0351743 A1 | 12/2015 | Stiggelbout |
| 2015/0351759 A1 | 12/2015 | Bennett et al. |

FOREIGN PATENT DOCUMENTS

| | | |
|---|---|---|
| EP | 1970016 | 9/2008 |
| EP | 2698128 | 2/2014 |
| GB | 2154484 | 9/1985 |
| JP | 1996-033635 | 2/1996 |
| JP | 1996-509918 | 10/1996 |
| JP | 10-52431 A | 2/1998 |
| JP | 2003-501132 | 1/2003 |
| JP | 2008-510526 | 4/2008 |
| JP | 2008-546489 A | 12/2008 |
| JP | 5474996 B2 | 4/2014 |
| WO | 96/27331 | 9/1996 |
| WO | 97/47246 | 12/1997 |
| WO | 2000/74578 | 12/2000 |
| WO | 2002/007609 | 1/2002 |
| WO | 2009/107121 | 9/2009 |
| WO | 10/056785 | 5/2010 |
| WO | 10/056786 | 5/2010 |
| WO | 10/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013/071234 | 5/2013 |
| WO | 2013/102909 | 7/2013 |
| WO | 2014/147619 | 9/2014 |
| WO | 2017/051404 | 3/2017 |

OTHER PUBLICATIONS

An Office Action dated Mar. 21, 2017, which issued during the prosecution of U.S. Appl. No. 14/240,227.

An Office Action dated Mar. 20, 2017, which issued during the prosecution of U.S. Appl. No. 14/240,082.

European Search Report dated Jan. 17, 2017, which issued during the prosecution of Applicant's European App No. 14769413.7.

An Office Action dated Nov. 22, 2016 which issued during the prosecution of Japanese Patent Application No. 550801/2014.

An Office Action dated Oct. 13, 2016, which issued during the prosecution of U.S. Appl. No. 14/240,082.

Notice of Allowance together with the English translation dated Nov. 1, 2017, which issued during the prosecution of Korean Patent Application No. 10-2013-7003093.

U.S. Appl. No. 61/636,751, filed Apr. 23, 2012.

U.S. Appl. No. 61/584,267, filed Jan. 8, 2012.

U.S. Appl. No. 61/526,717, filed Aug. 24, 2011.

U.S. Appl. No. 61/363,247, filed Jul. 11, 2010.

U.S. Appl. No. 61/714,813, filed Oct. 17, 2012.

An International Search Report and a Written Opinion both dated Jan. 23, 2013, which issued during the prosecution of Applicant's PCT/IL2012/000318.

An International Search Report and a Written Opinion both dated Dec. 5, 2011, which issued during the prosecution of Applicant's PCT/IL2011/000549.

An International Search Report and a Written Opinion both dated May 10, 2013 which issued during the prosecution of Applicant's PCT/IL2013/050030.

An International Search Report dated Jan. 8, 2013 which issued during the prosecution of Applicant's PCT/IL2012/000319.

An English translation of an Office Action dated Mar. 24, 2015, which issued during the prosecution of Japanese Patent Application No. 519213/2013.

An English translation of an Office Action dated Jul. 3, 2014 which issued during the prosecution of Chinese Patent Application 2011800437287.

An International Search Report and Written Opinion both dated Jul. 11, 2014, which issued during the prosecution of Applicant's PCT/IL 14/50299.

An International Preliminary Search Report dated Aug. 26, 2014, which issued during the prosecution of Applicant's PCT/IL2013/050030.

An International Preliminary Report dated Feb. 25, 2014 which issued during the prosecution of Applicant's PCT/IL2012/000319.

Written Opinion dated Jan. 8, 2013 which issued during the prosecution of Applicant's PCT/IL2012/000319.

An International Preliminary Report dated Feb. 25, 2014 which issued during the prosecution of Applicant's PCT/IL2012/000318.

(56) References Cited

OTHER PUBLICATIONS

An Office Action dated Apr. 5, 2014 which issued during the prosecution of Australian Patent Application No. 2011277949.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
European Search Report dated Jun. 11, 2015 which issued during the prosecution of Applicant's European App No. 12826407.
European Search Report dated Jan. 20, 2016 which issued during the prosecution of Applicant's European App No. 13733888.
An Invitation to pay additional fees dated Dec. 23, 2015, which issued during the prosecution of Applicant's PCT/IL2015/050923.
Notice of Allowance dated Jan. 7, 2016, which issued during the prosecution of Japanese Patent Application No. 519213/2013.
An Office Action dated Feb. 25, 2016, which issued during the prosecution of U.S. Appl. No. 13/809,562.
An Office Action dated Sep. 1, 2016, which issued during the prosecution of U.S. Appl. No. 14/240,227.
An Invitation to pay additional fees dated Mar. 30, 2016, which issued during the prosecution of Applicant's PCT/IL2015/050978.
An English translation of an Office Action dated Oct. 13, 2015, which issued during the prosecution of Chinese Patent Application 2012800518842.
An English translation of an Office Action dated May 16, 2016, which issued during the prosecution of Chinese Patent Application 2012800518842.
U.S. Appl. No. 61/802,958, filed Mar. 18, 2013.
U.S. Appl. No. 61/887,561, filed Oct. 7, 2013.
An International Preliminary Report dated Sep. 22, 2016, which issued during the prosecution of Applicant's PCT/IL2014/050299.
U.S. Appl. No. 62/273,632, filed Dec. 31, 2015.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
An English translation of an Office Action dated Sep. 6, 2016, which issued during the prosecution of Japanese Patent Application No. 526597/2014.
An International Search Report and a Written Opinion both dated Aug. 23, 2017, which issued during the prosecution of Applicant's PCT/IL2016/051379.
An International Search Report and a Written Opinion both dated May 24, 2018, which issued during the prosecution of Applicant's PCT/IL2018/050180.
An Office Action dated May 8, 2018, which issued during the prosecution of U.S. Appl. No. 15/665,838.

\* cited by examiner

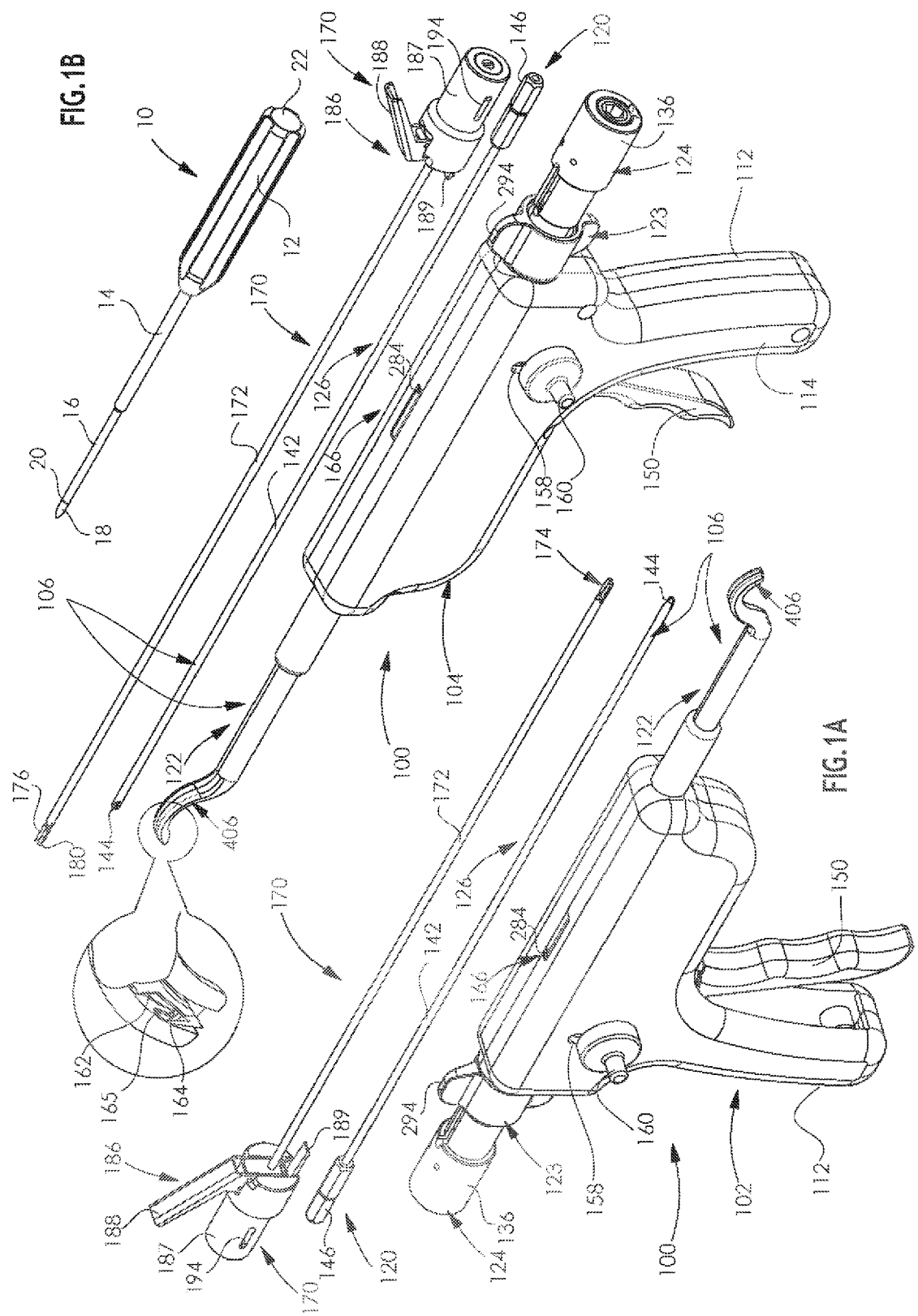

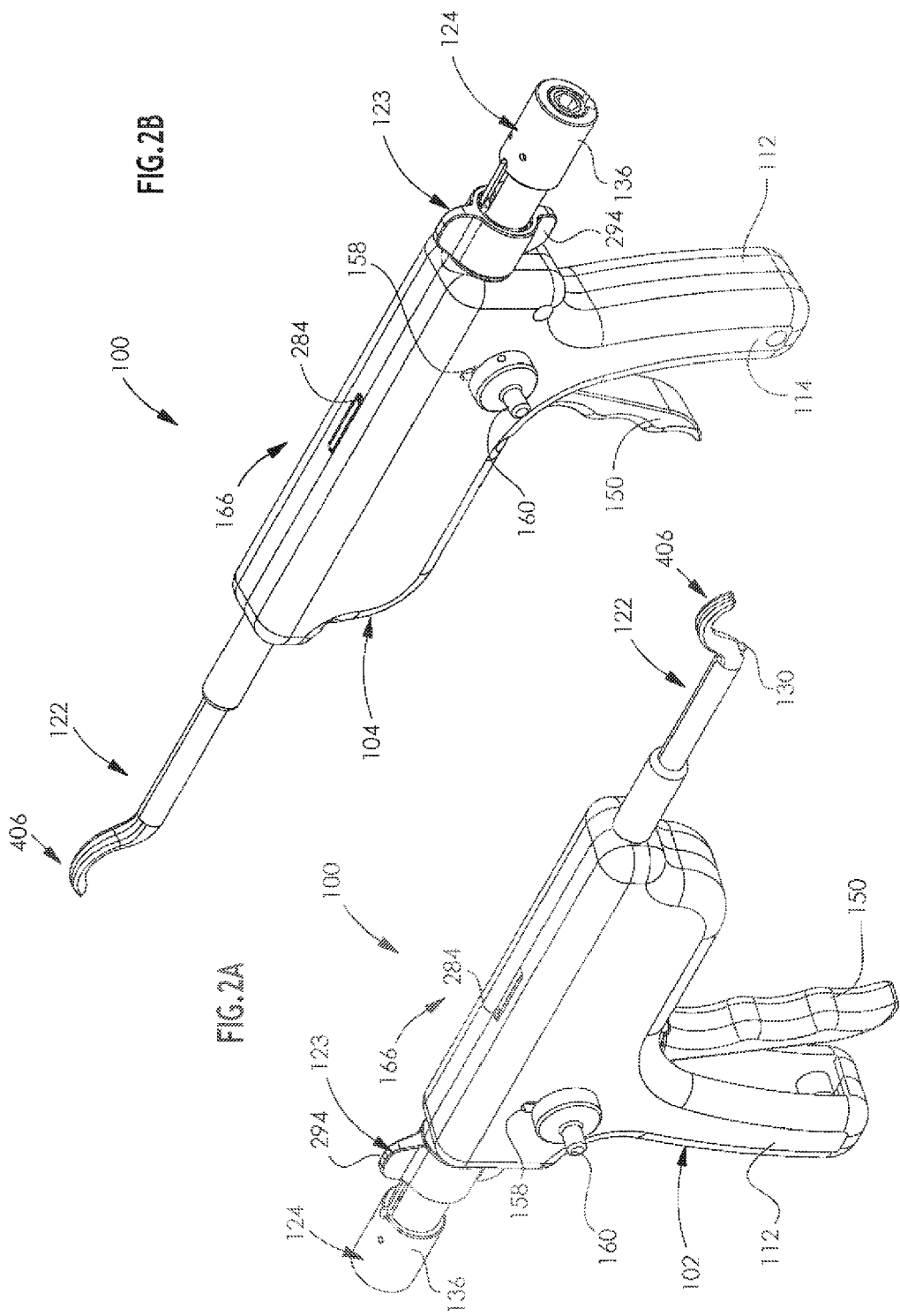

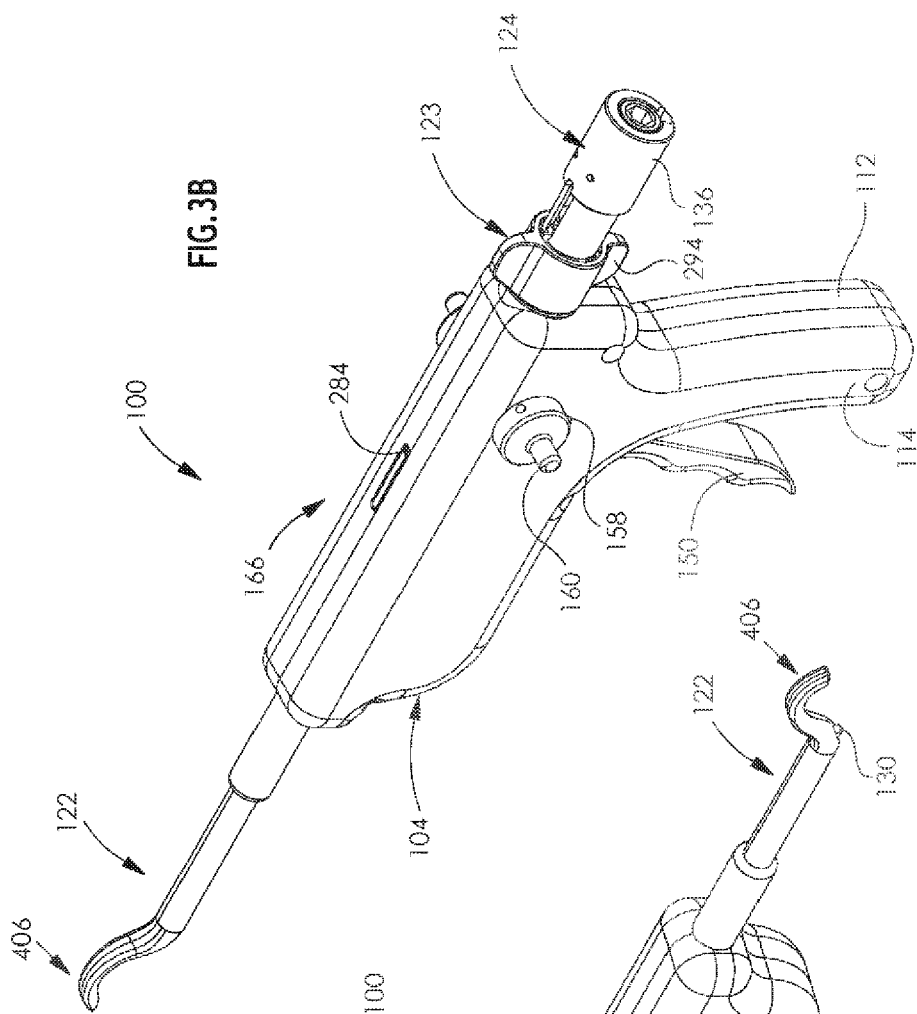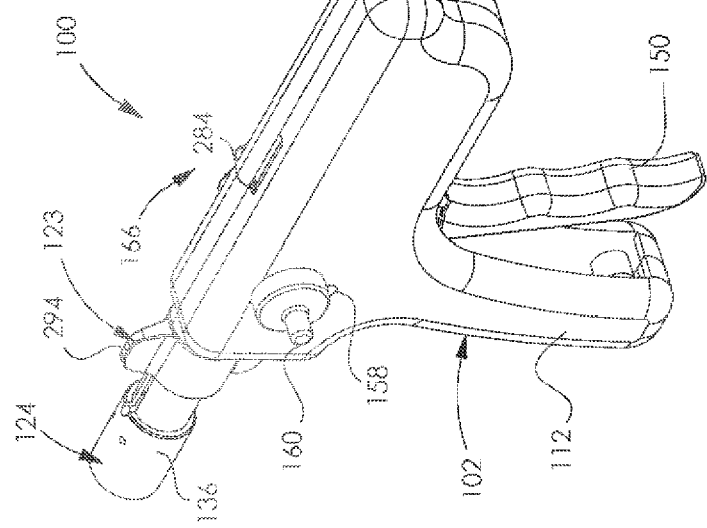

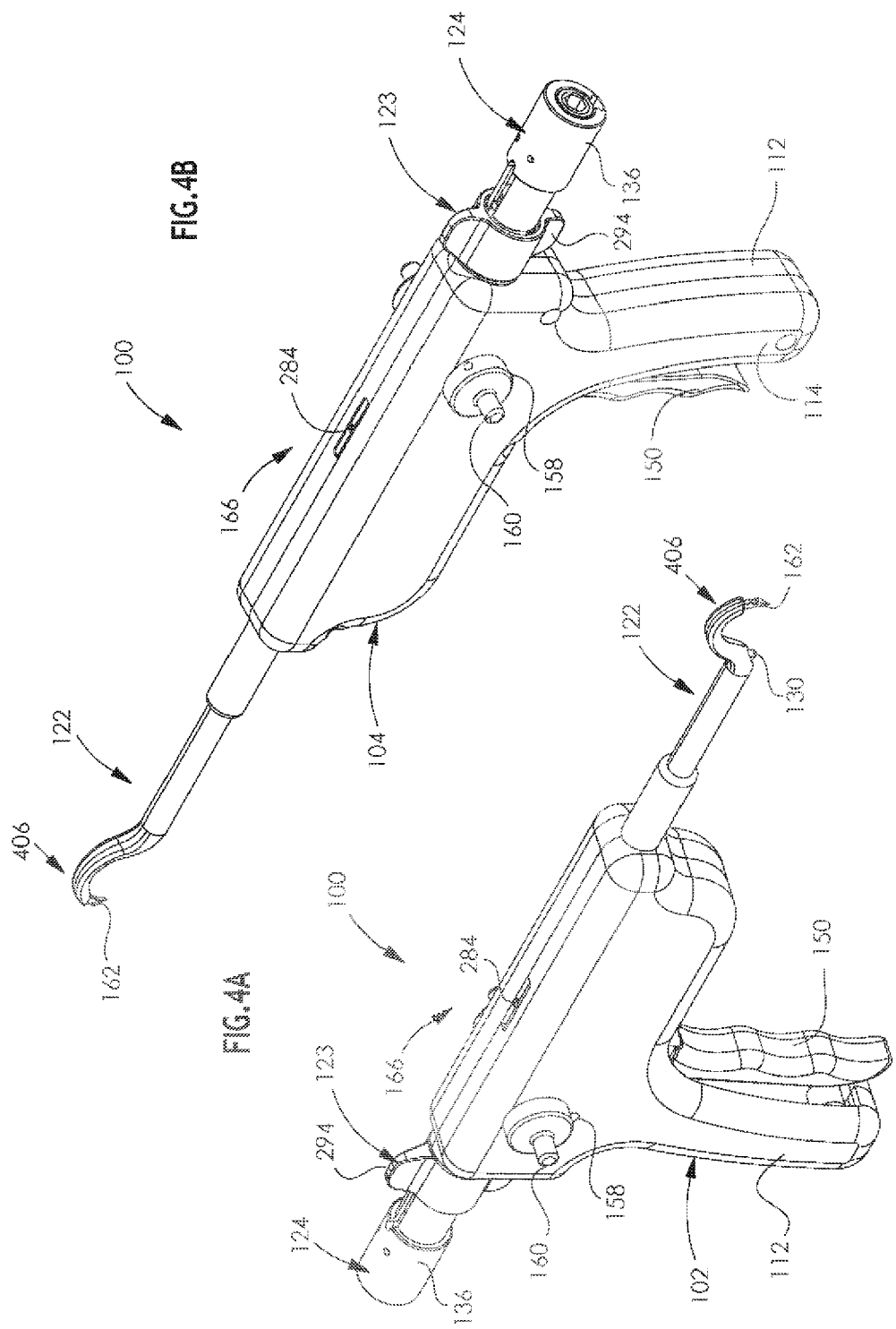

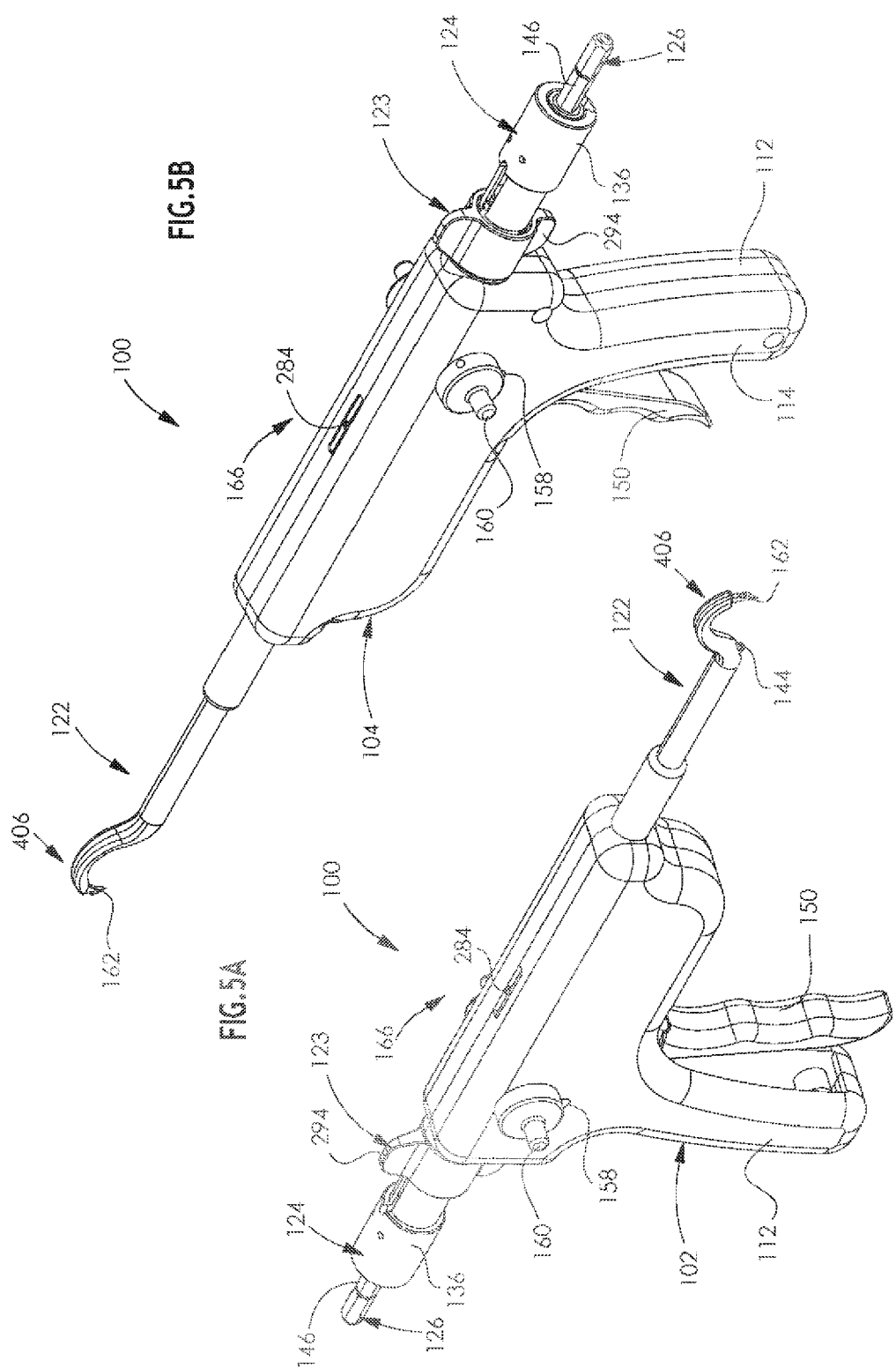

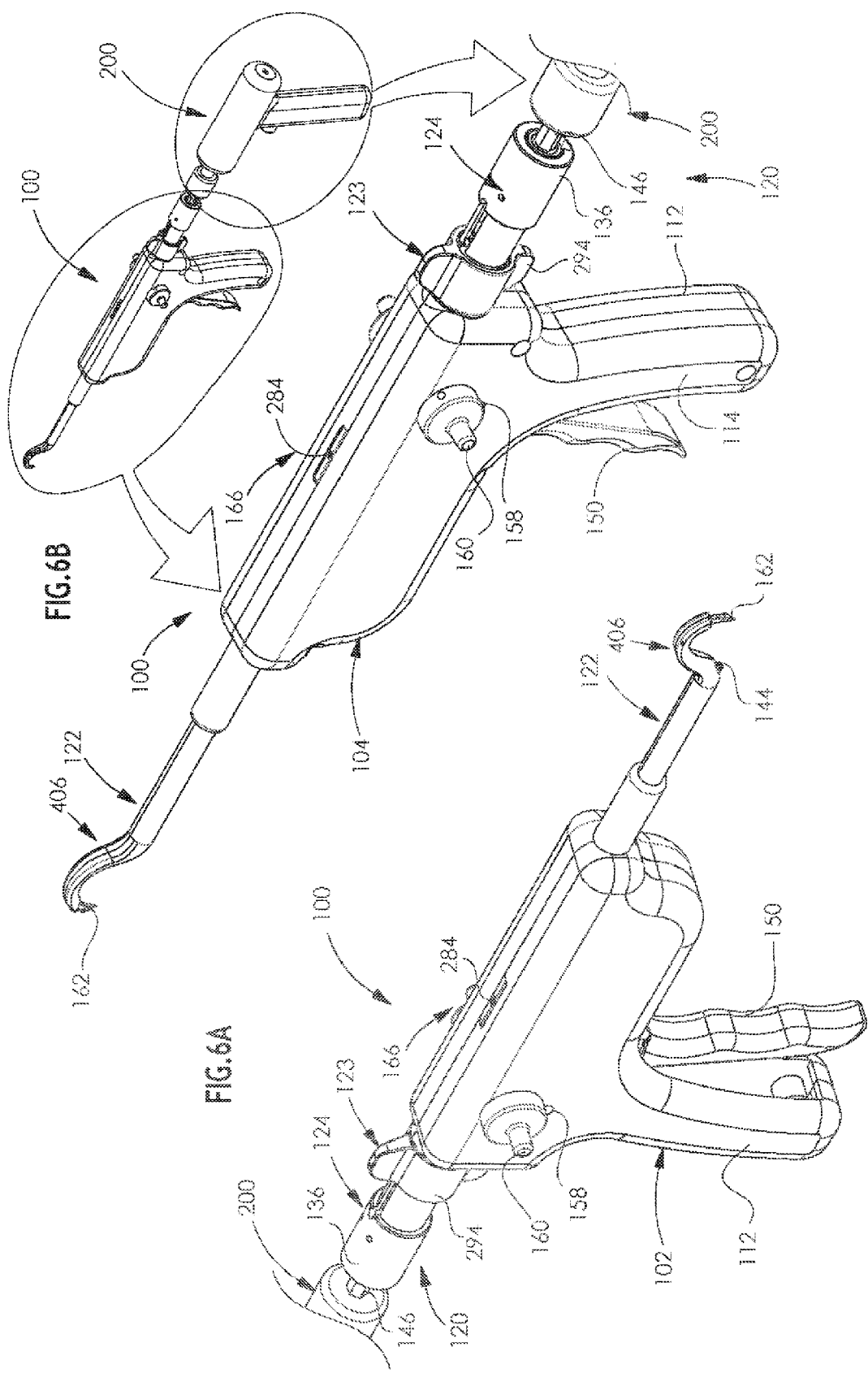

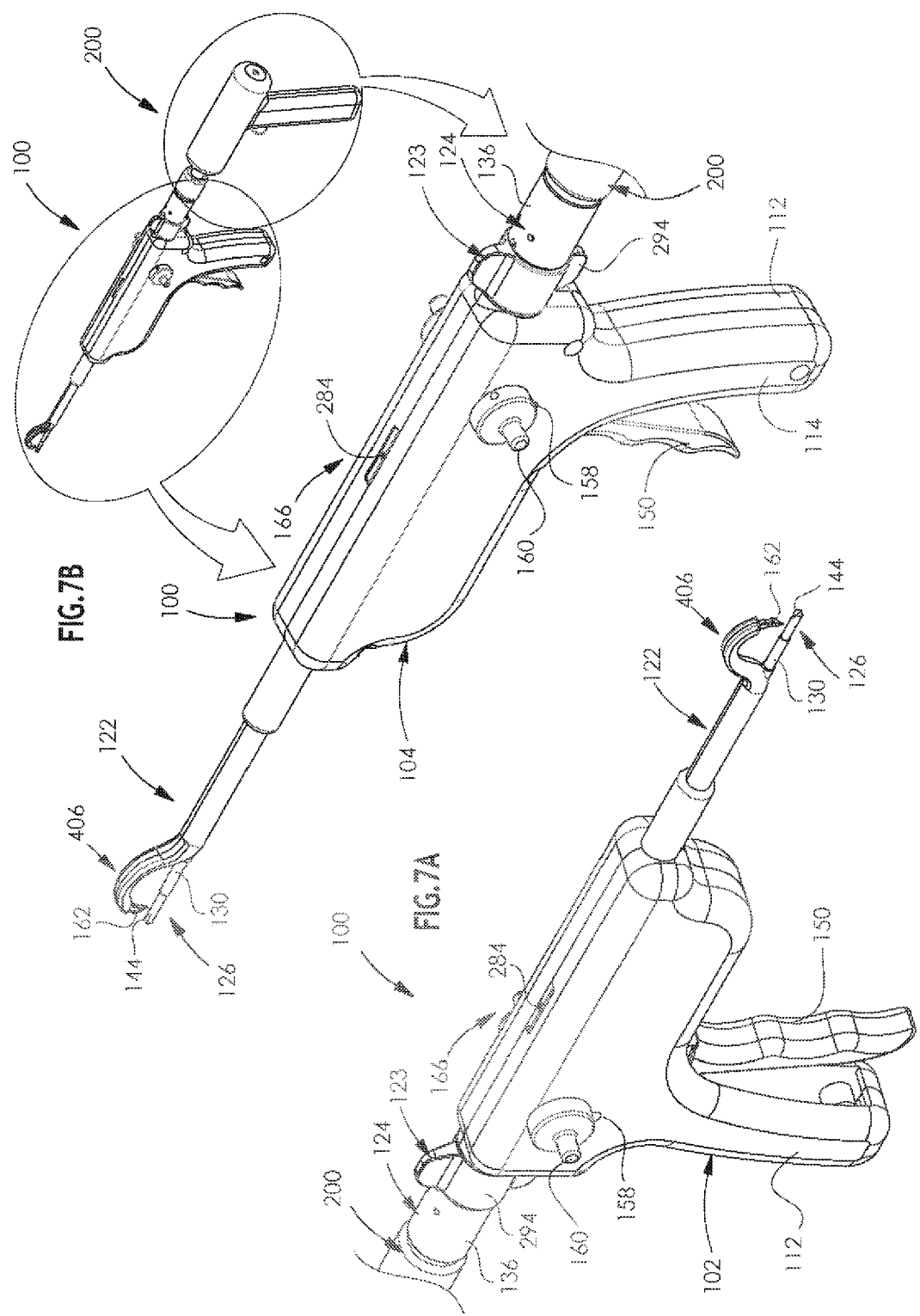

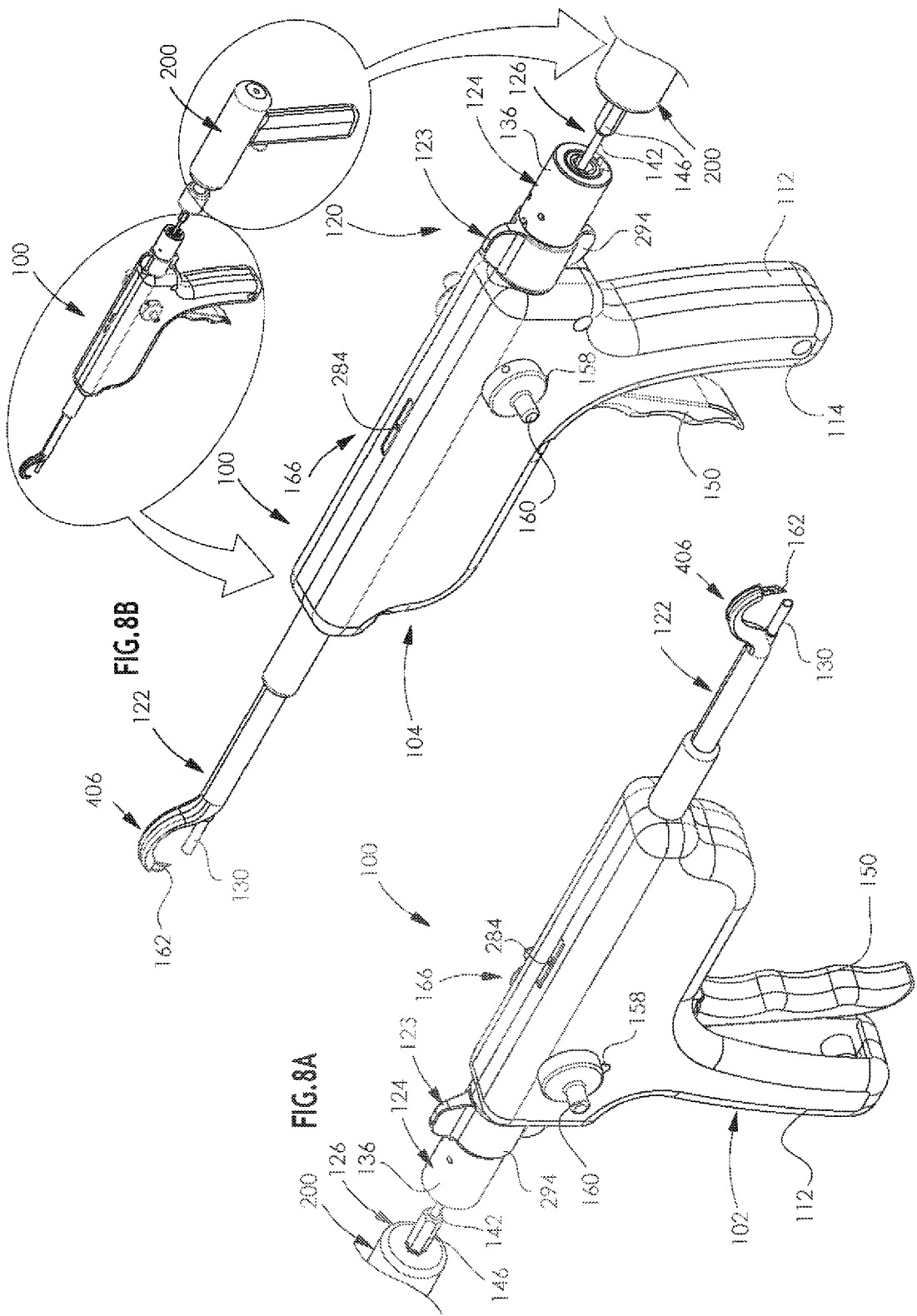

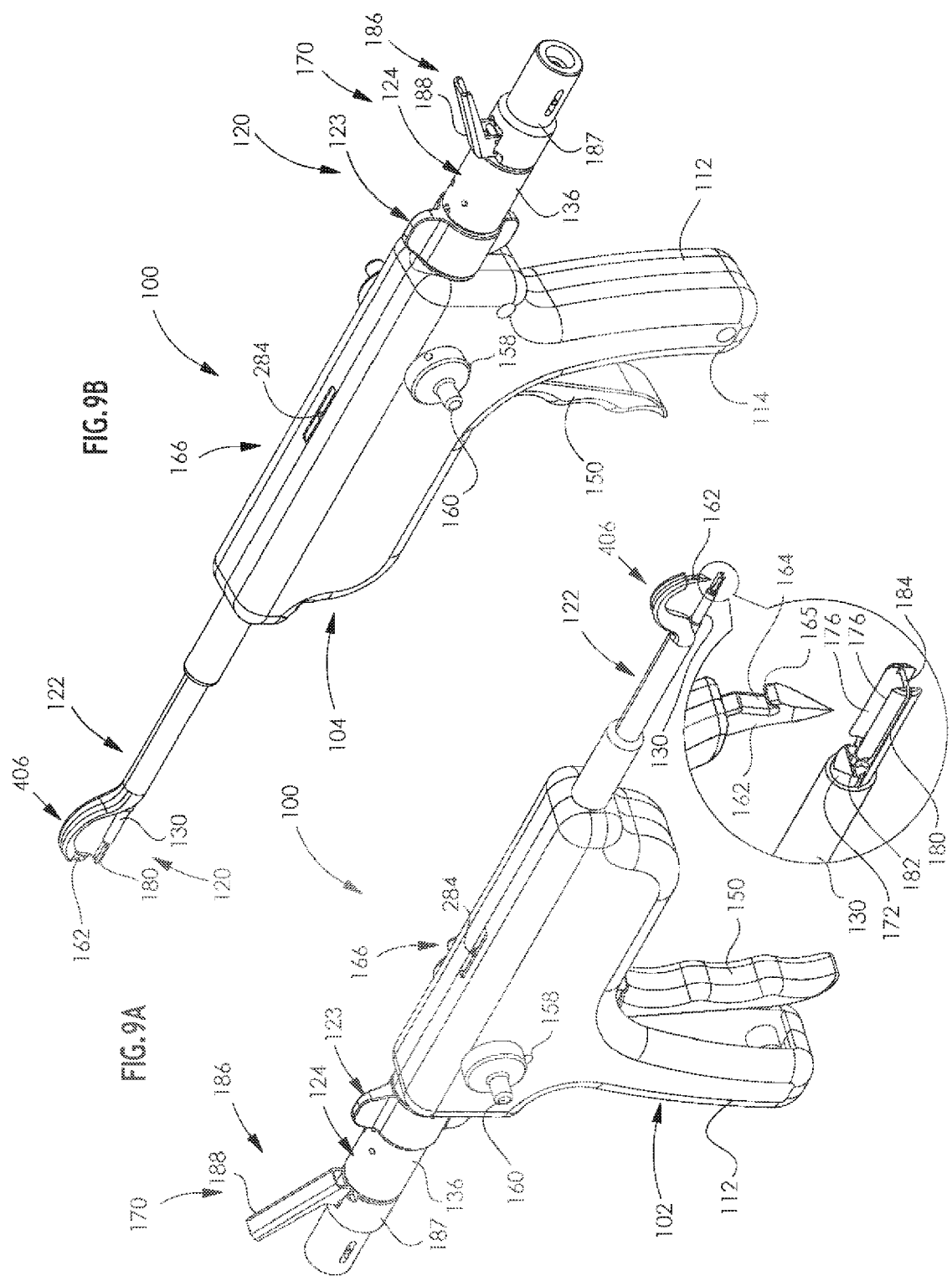

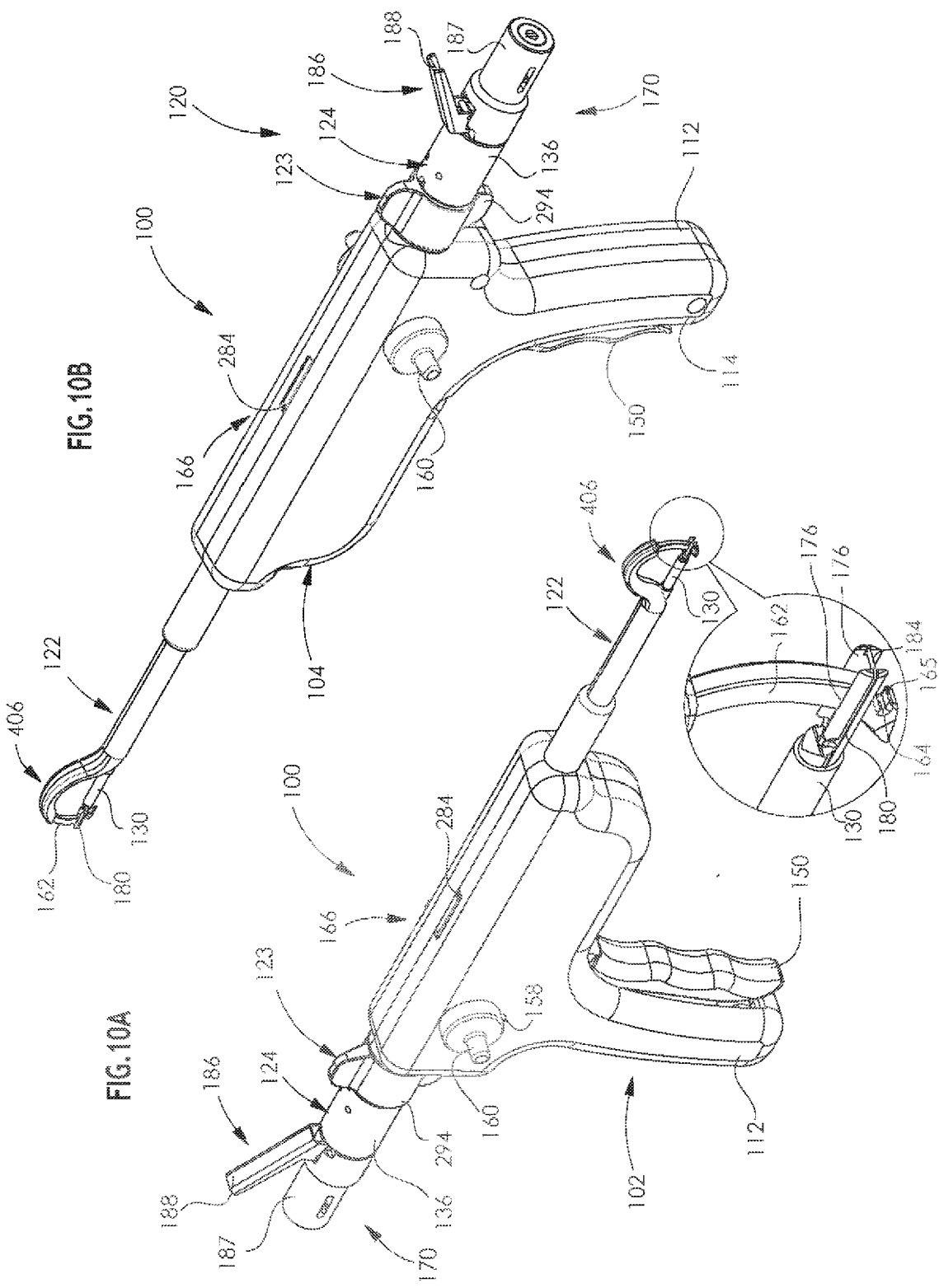

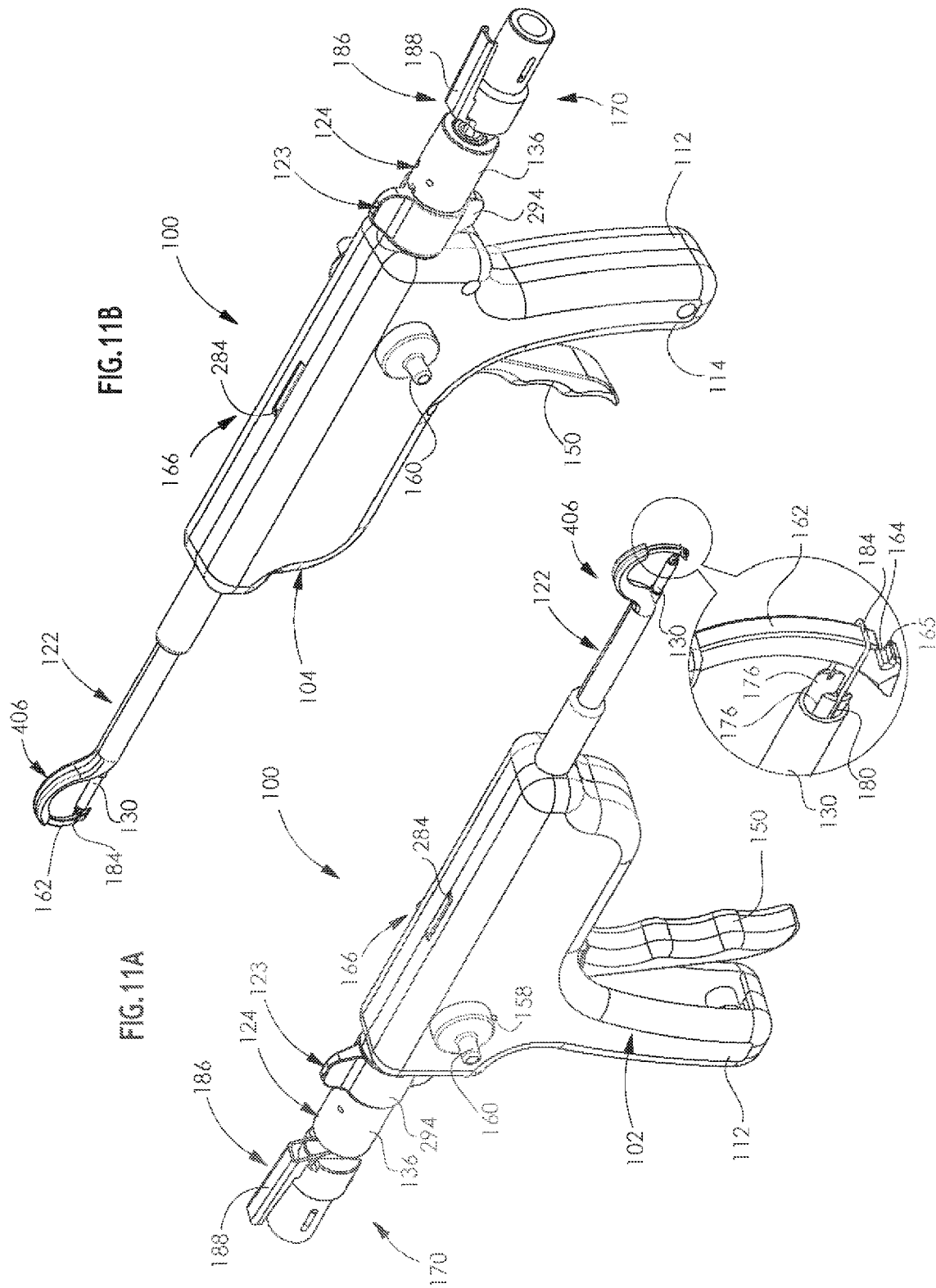

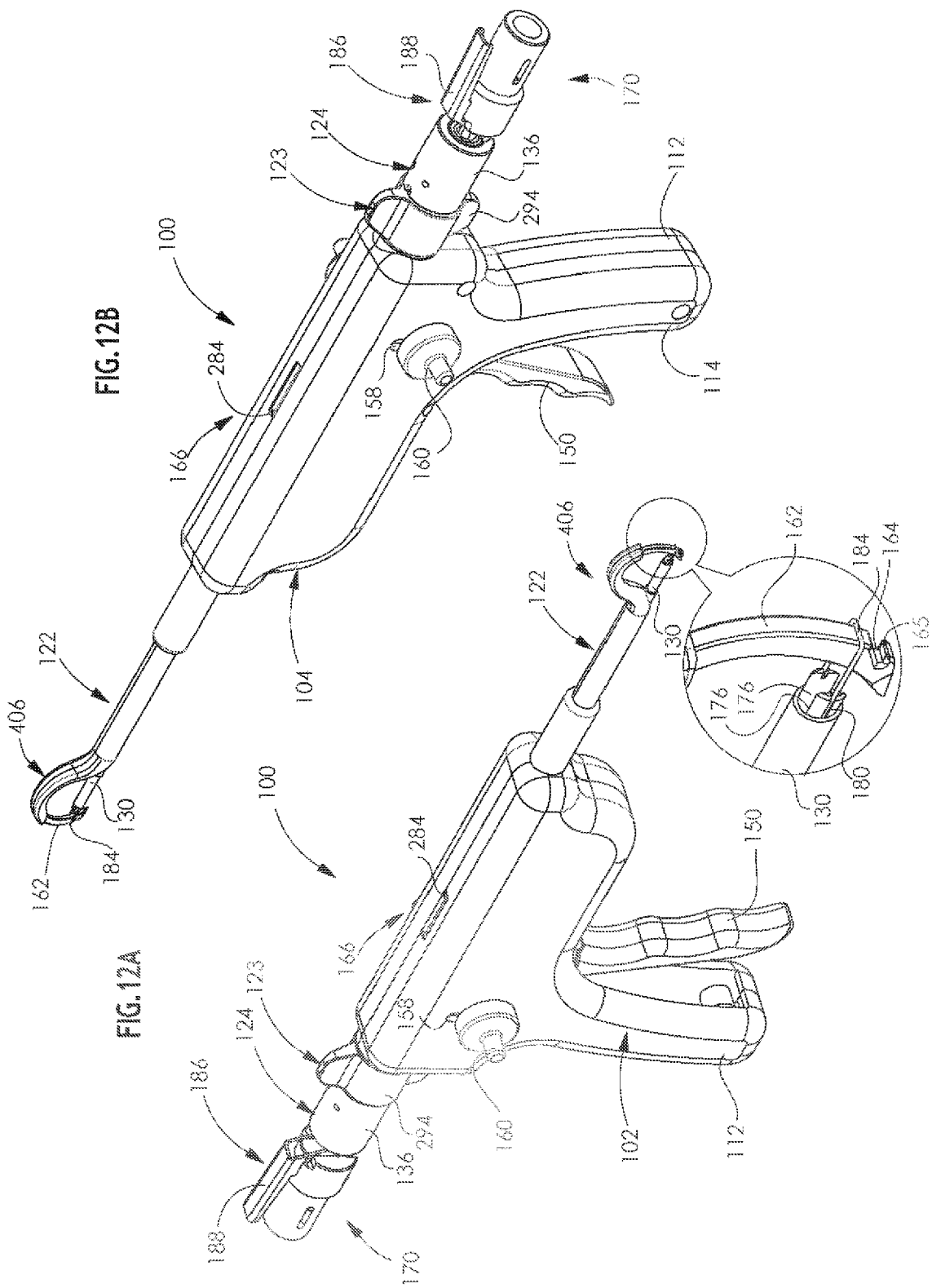

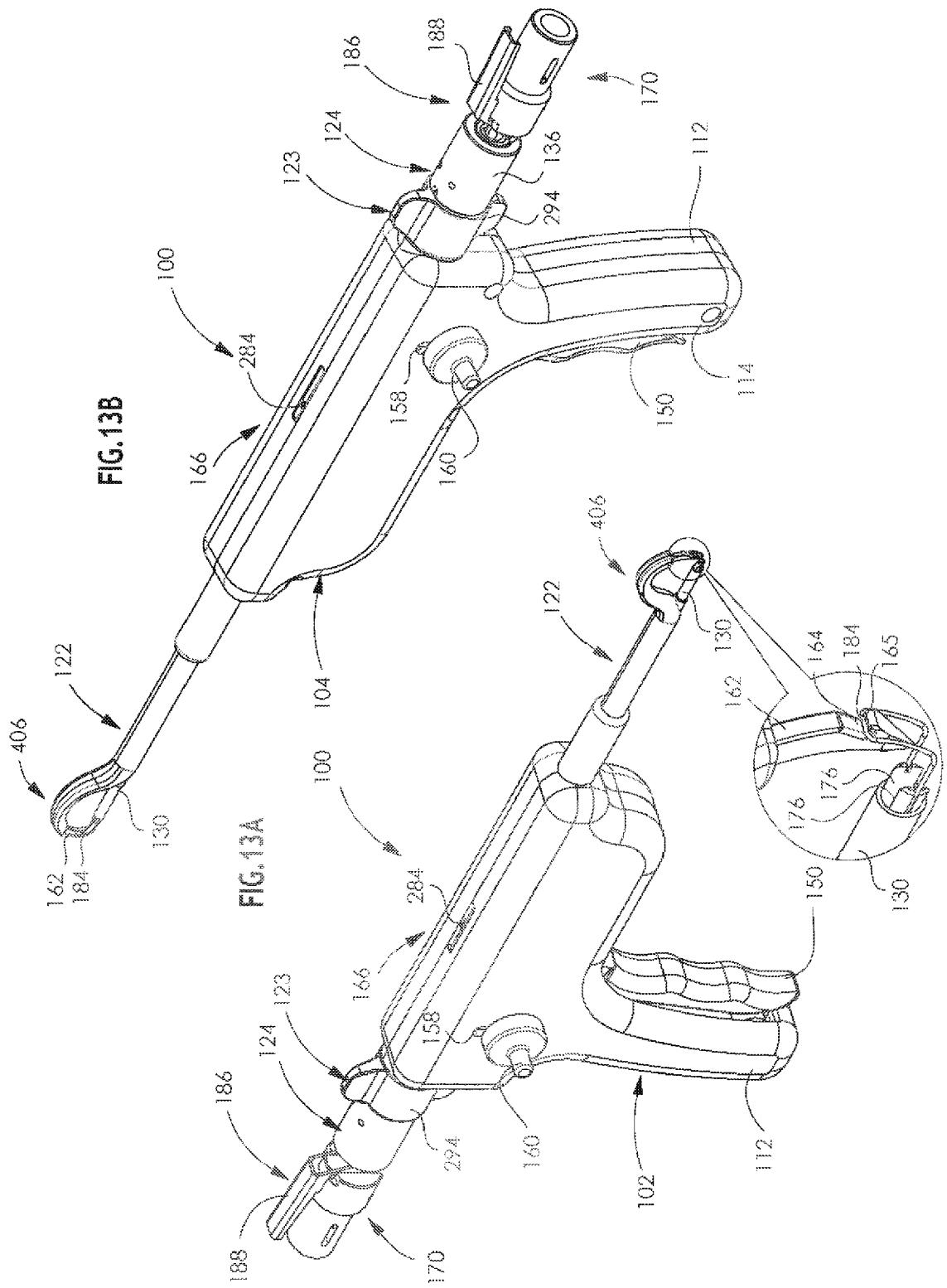

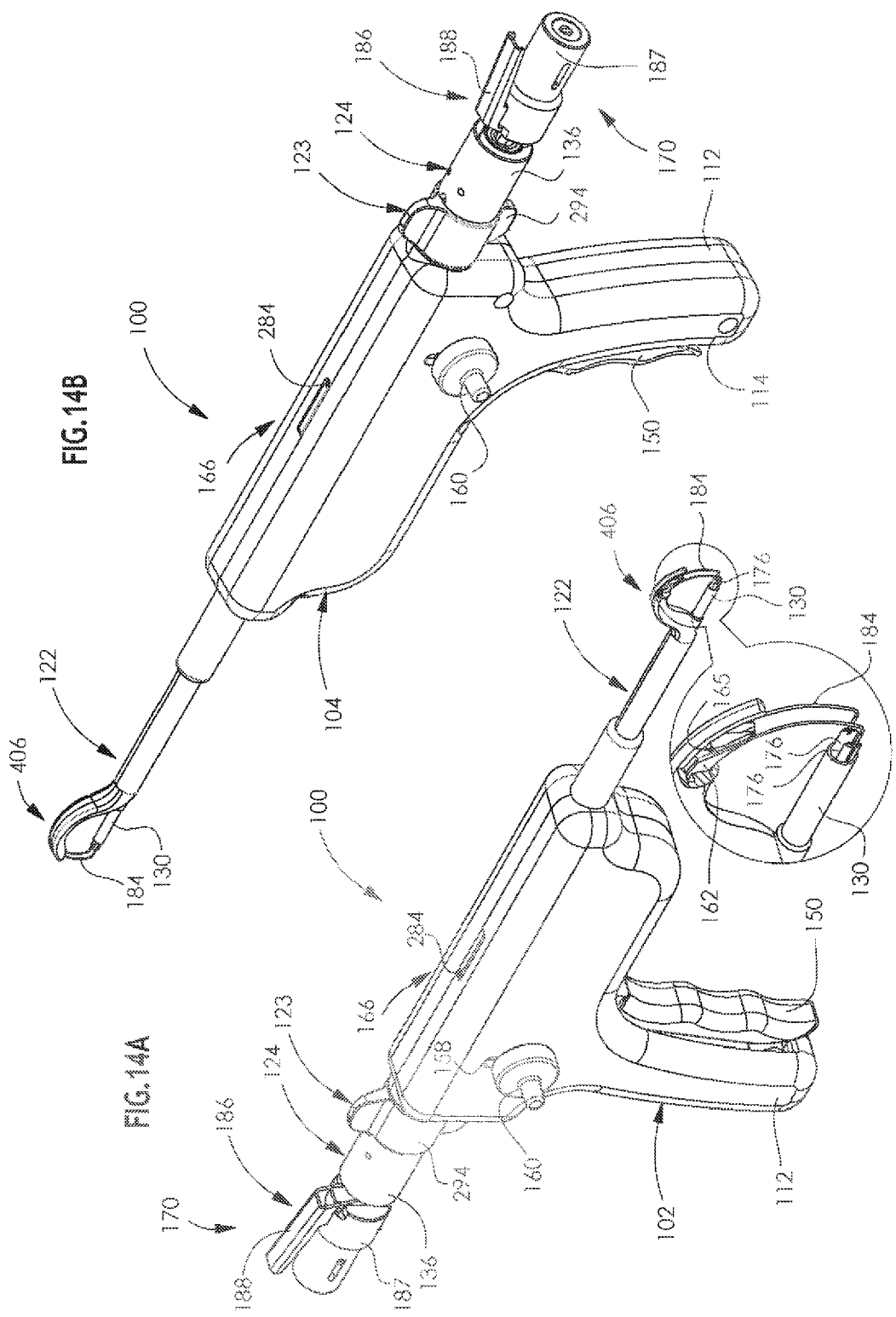

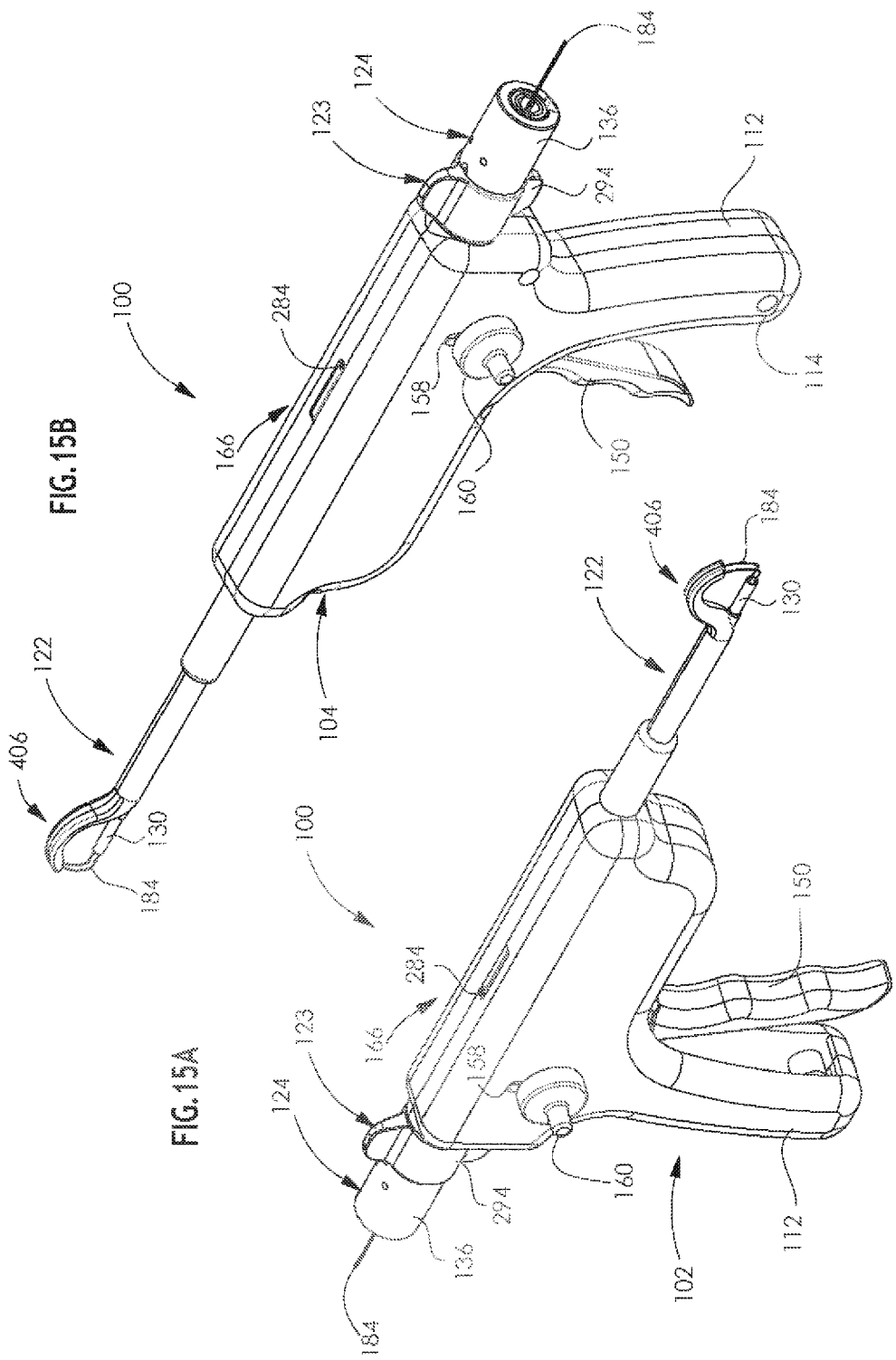

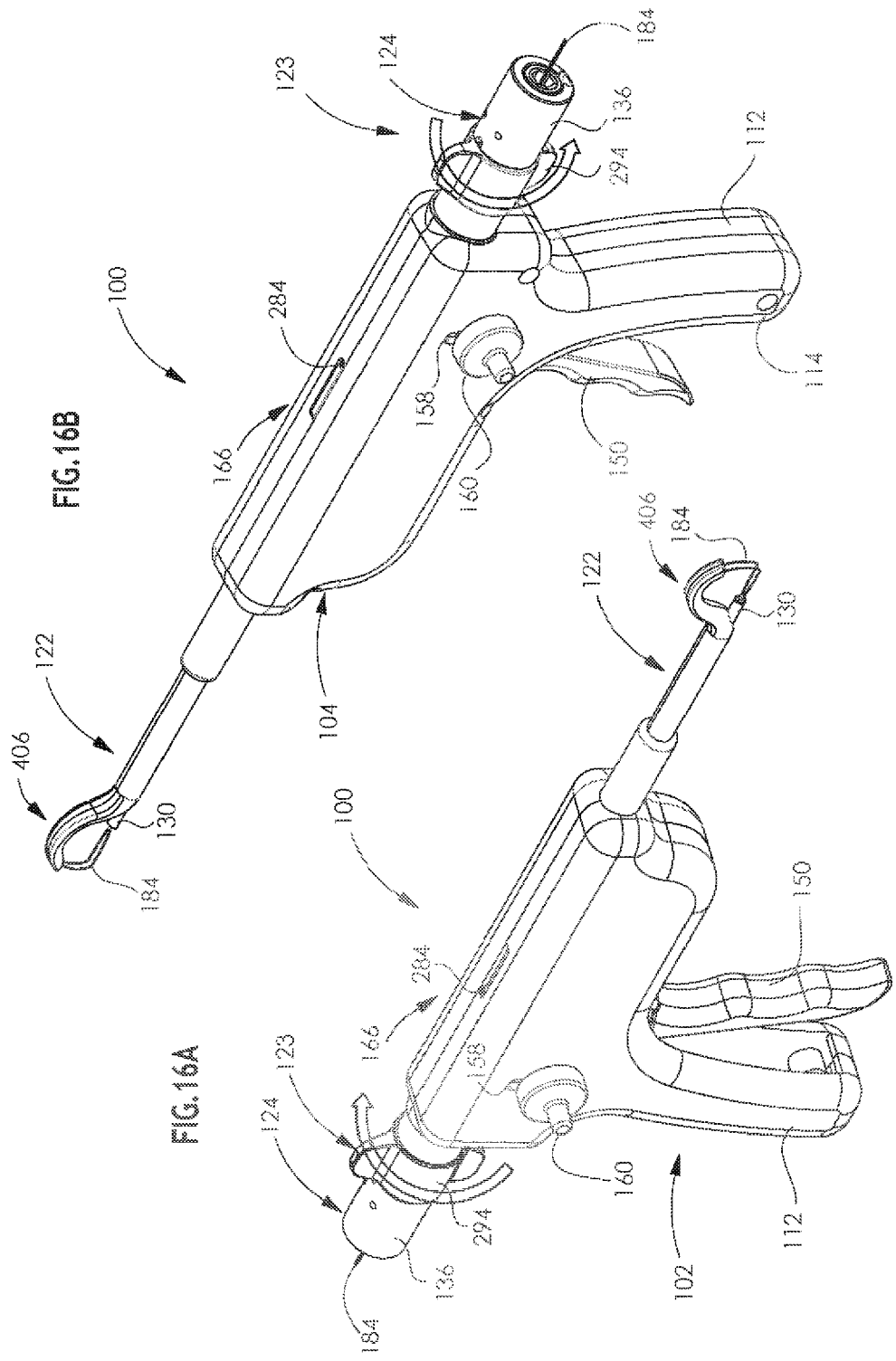

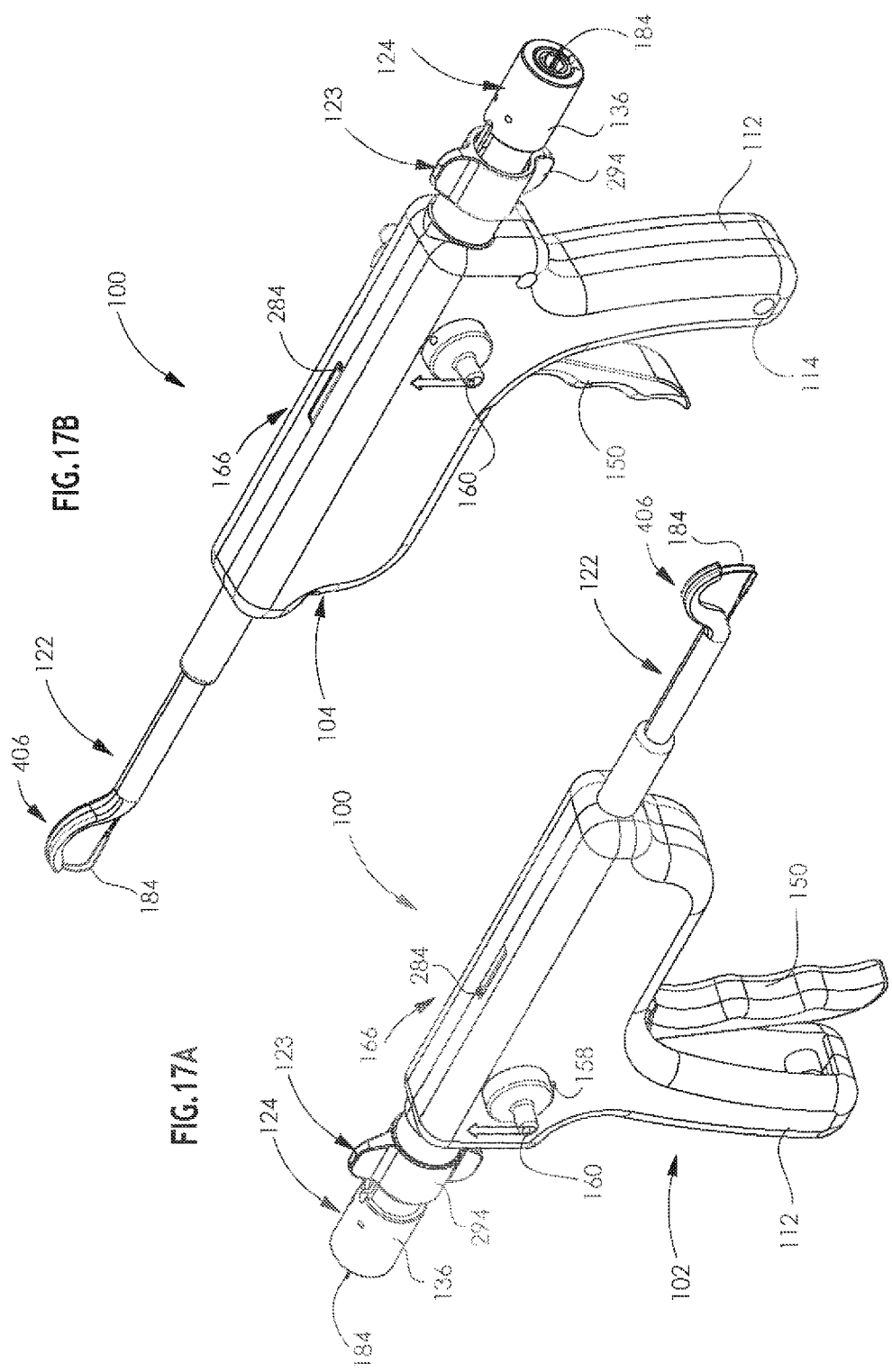

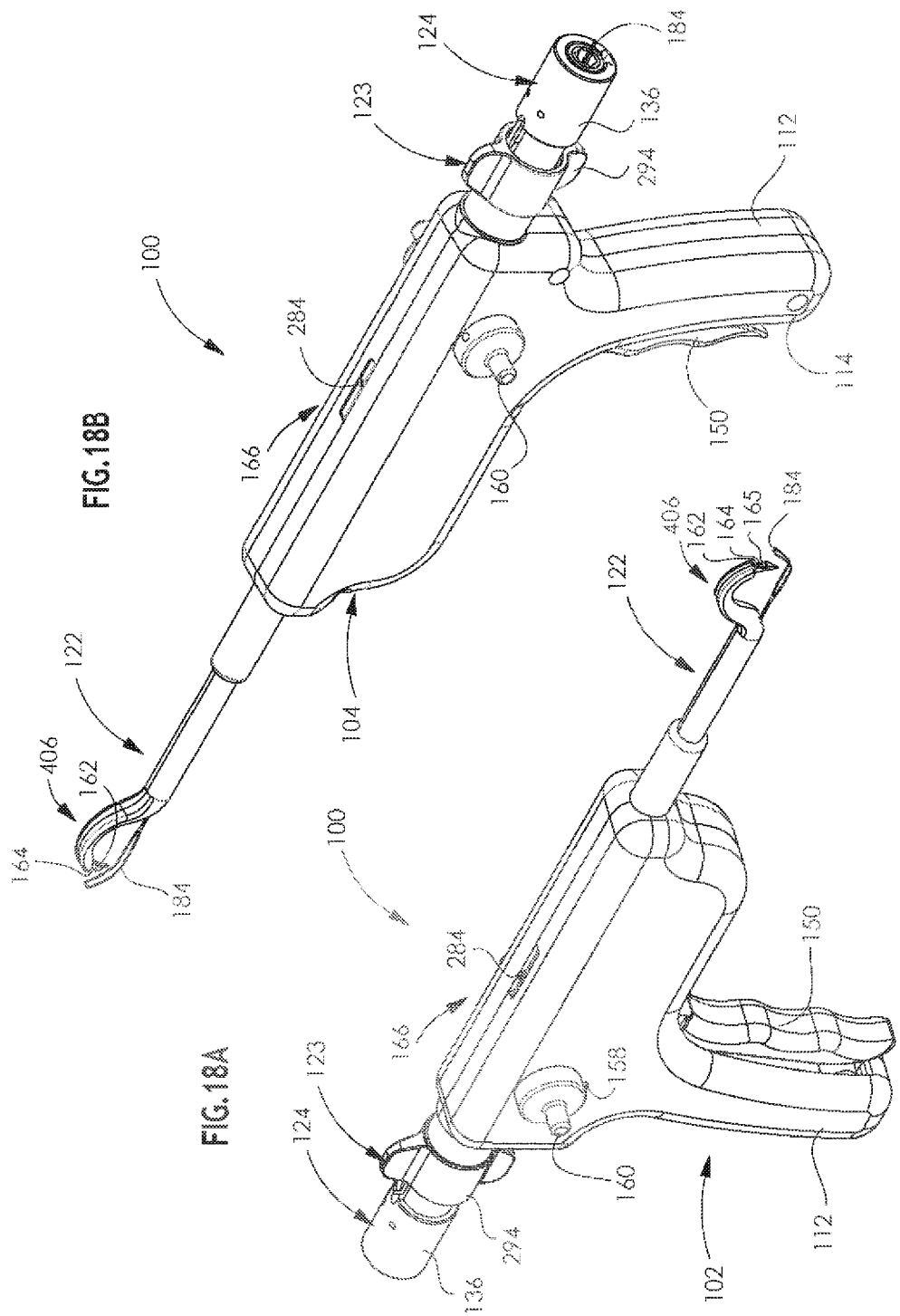

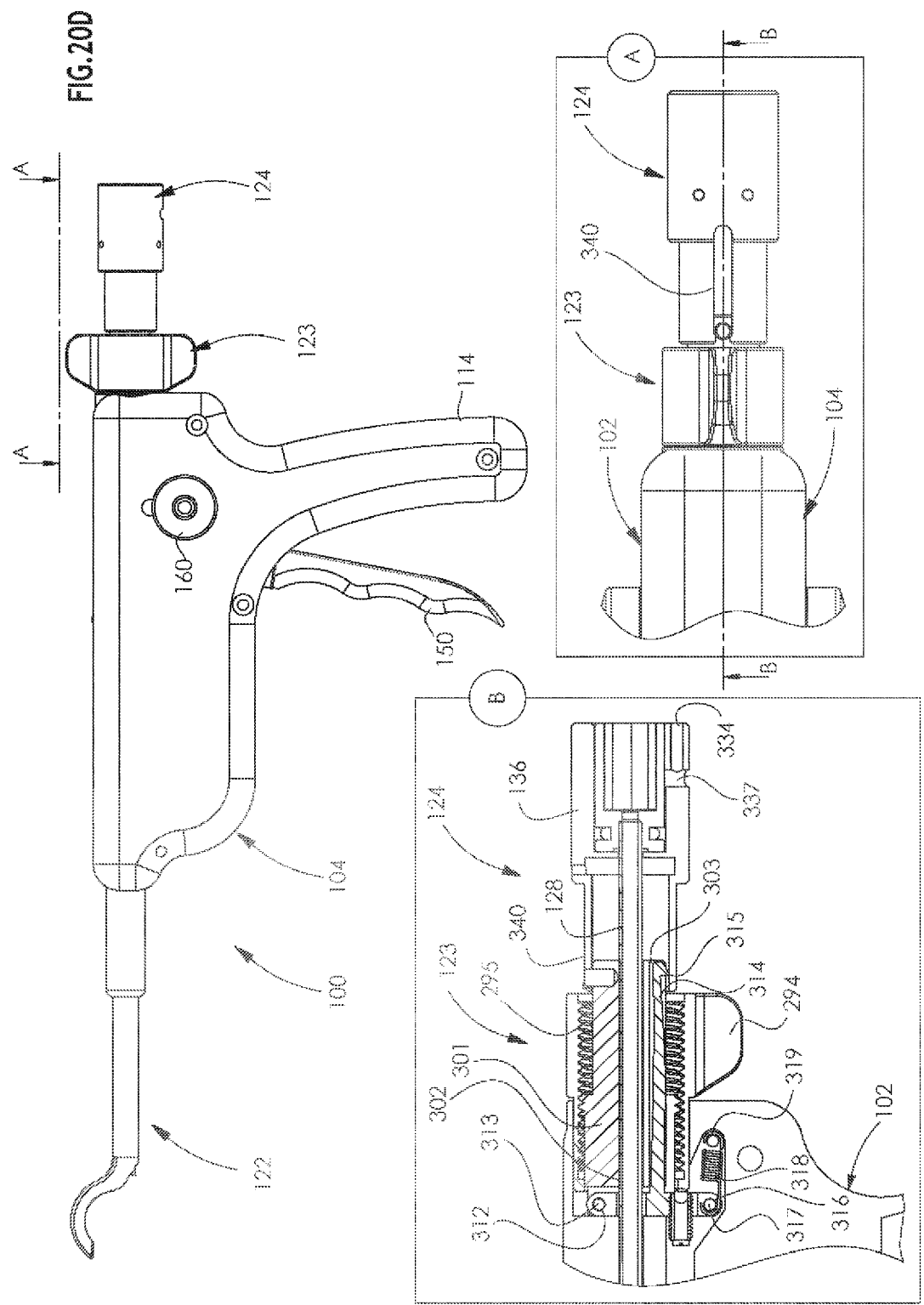

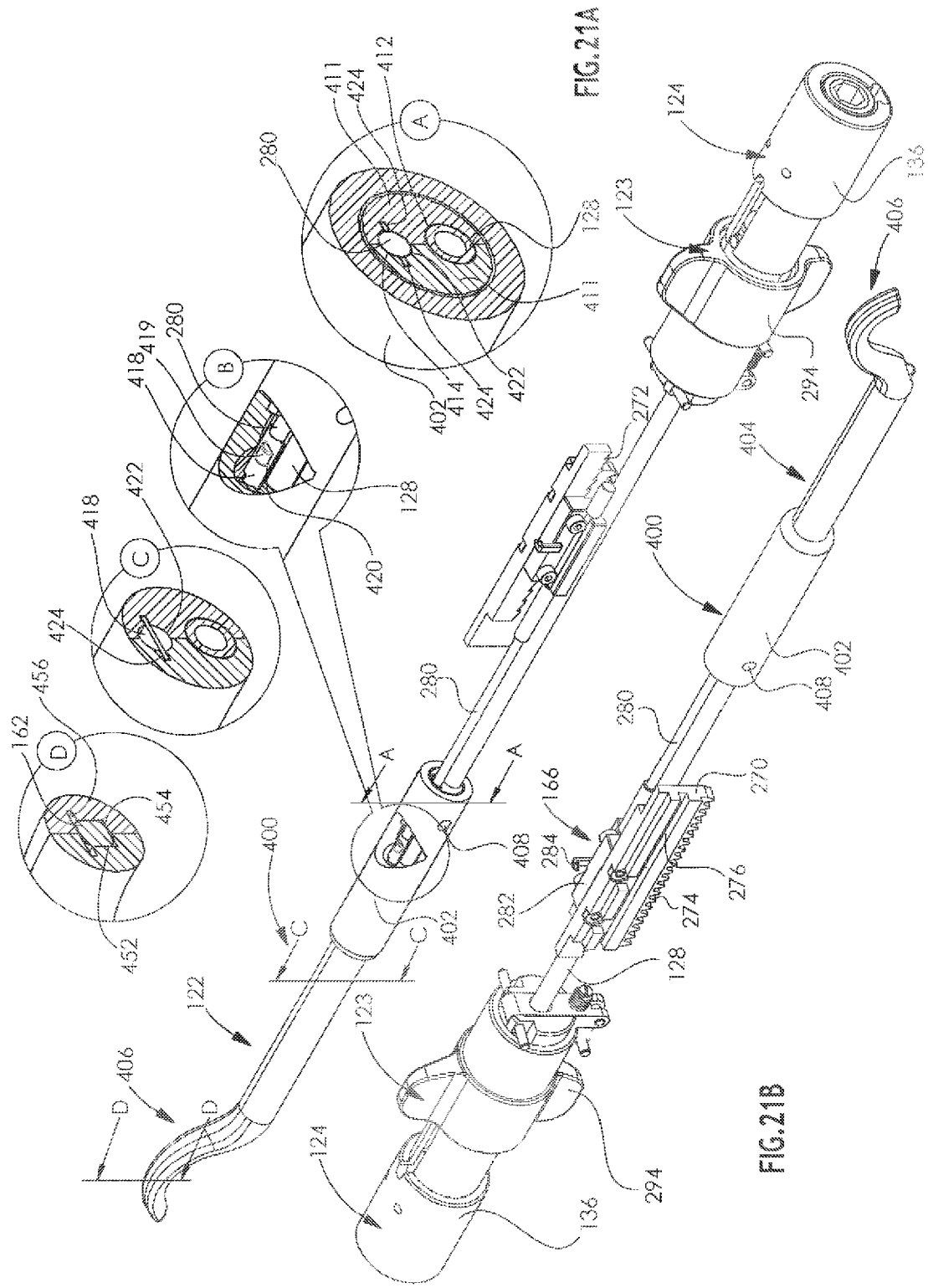

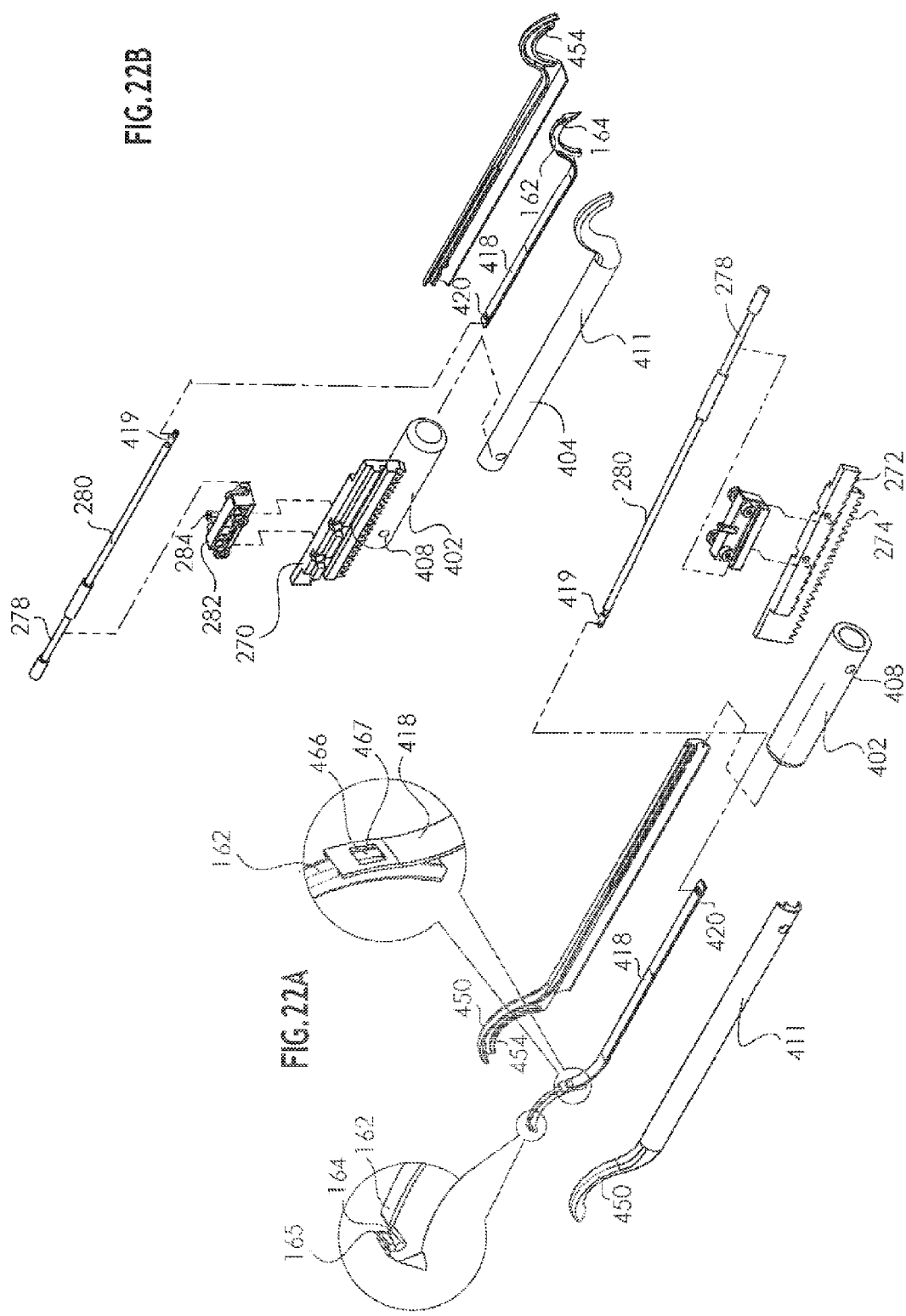

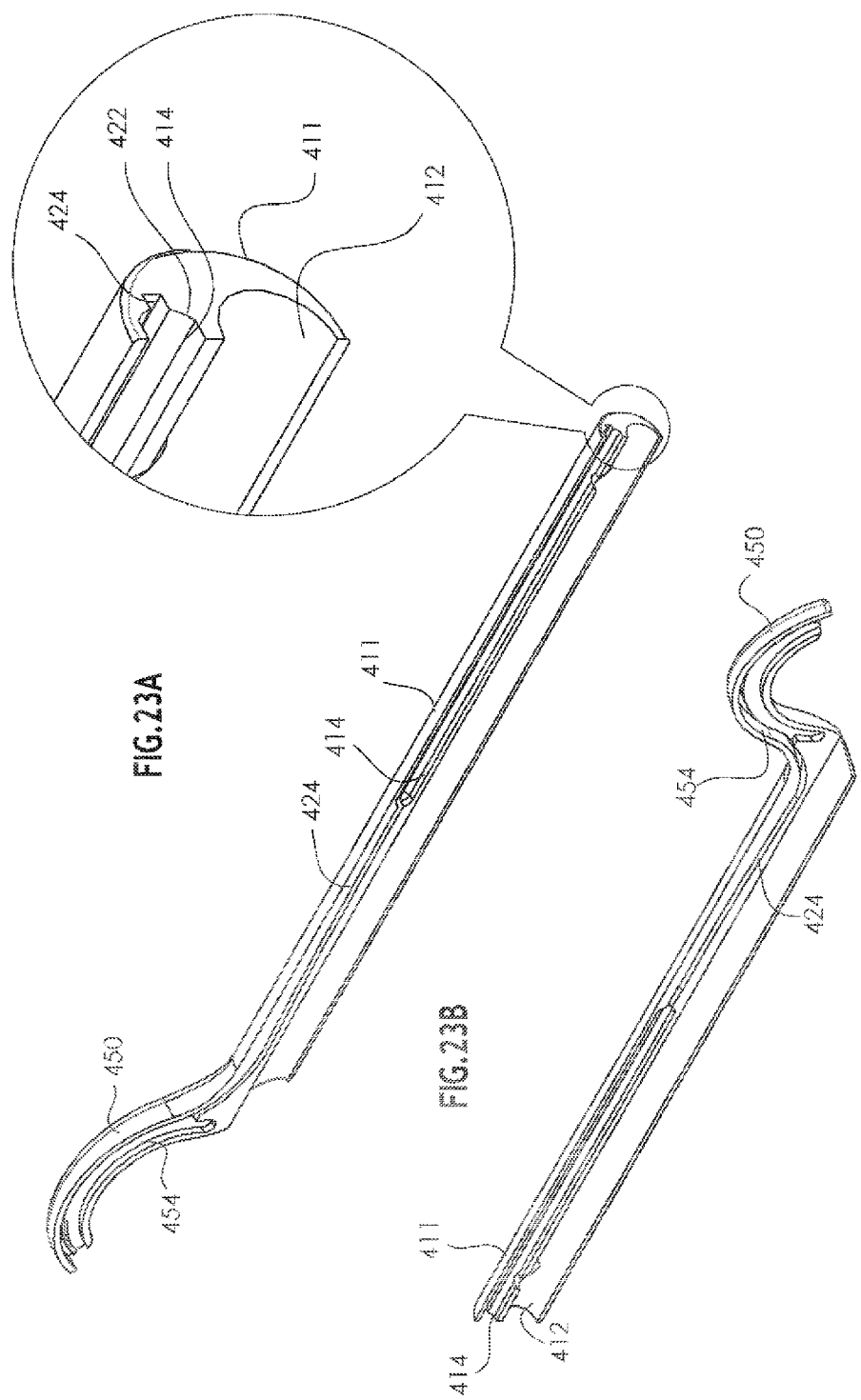

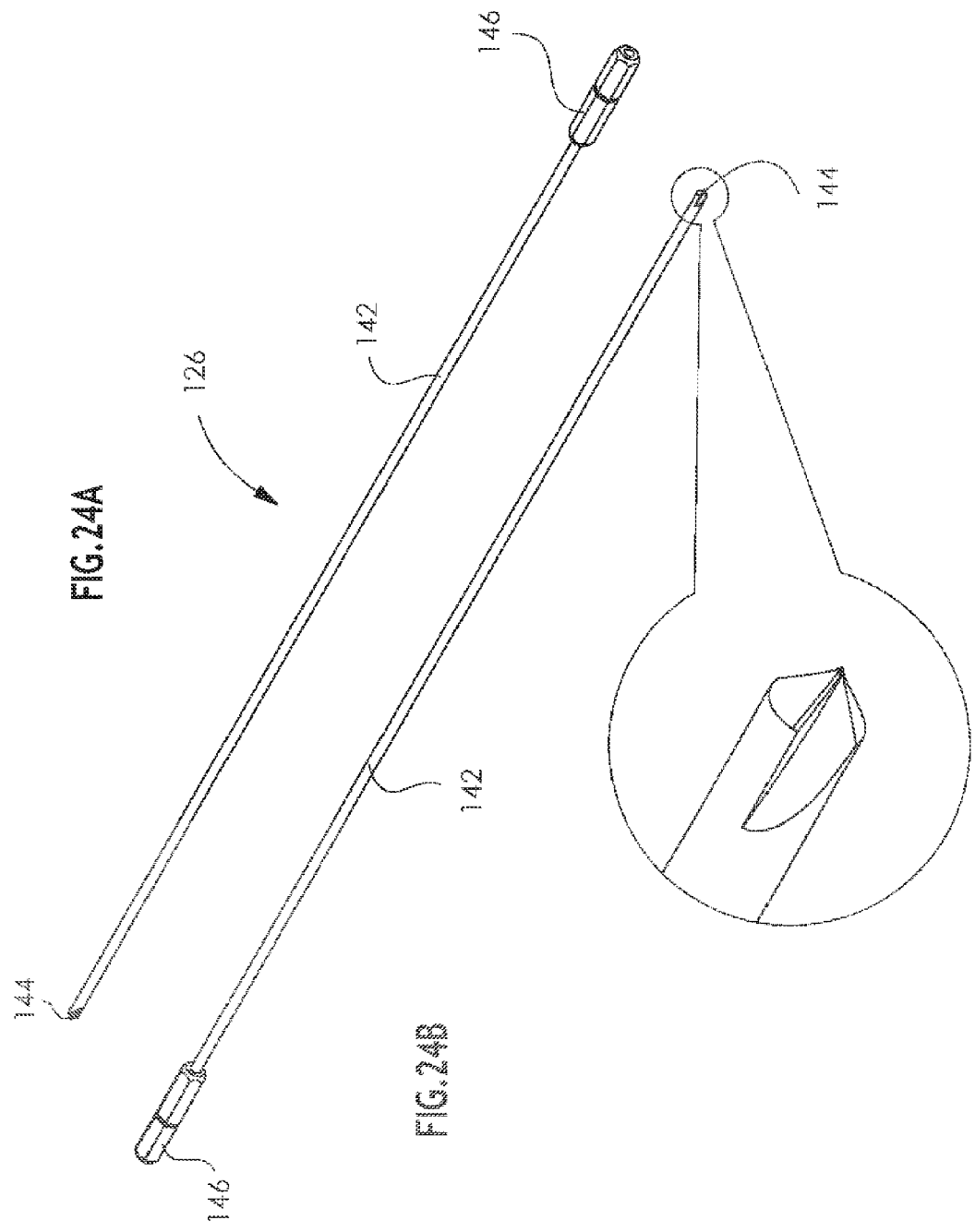

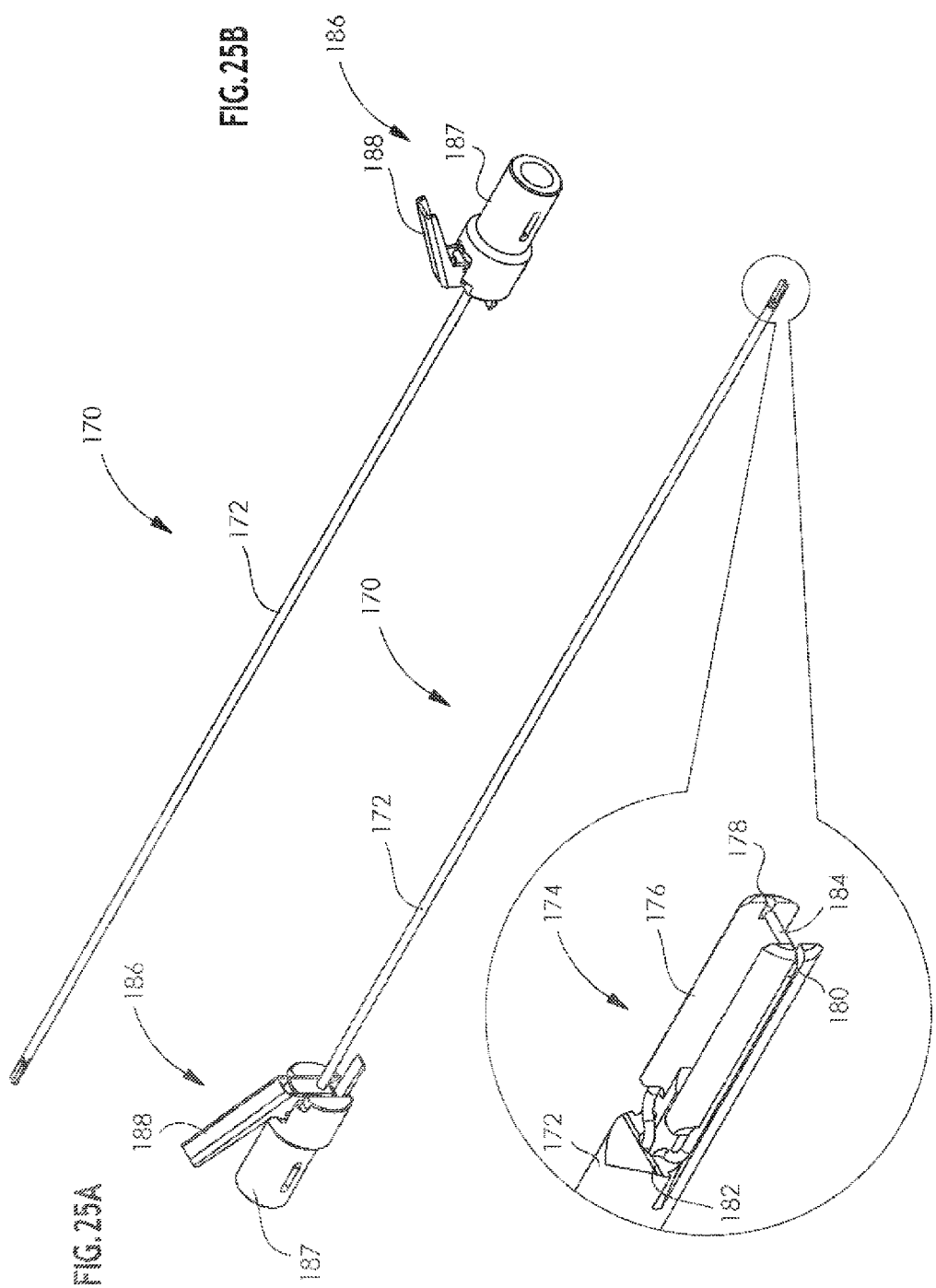

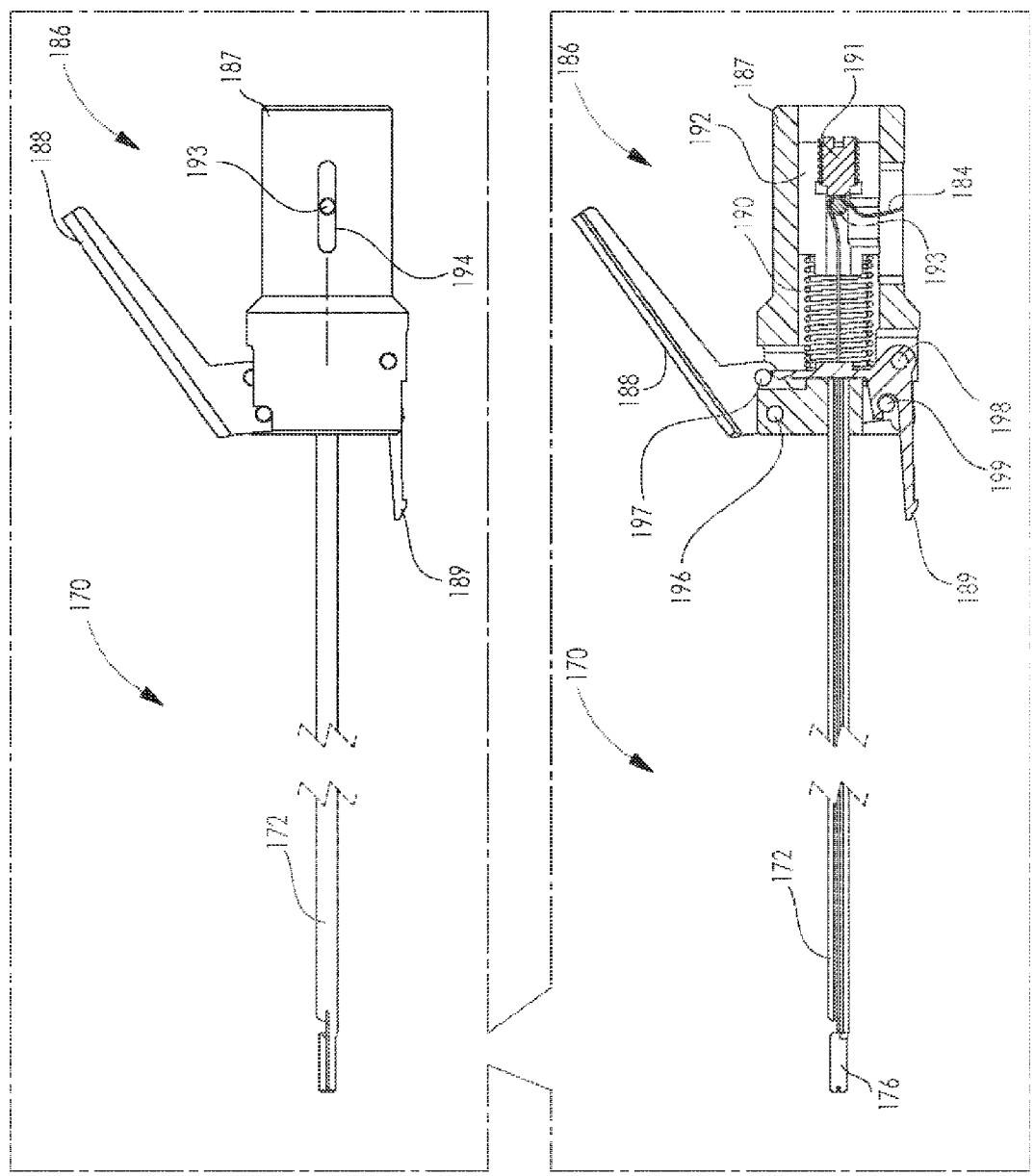

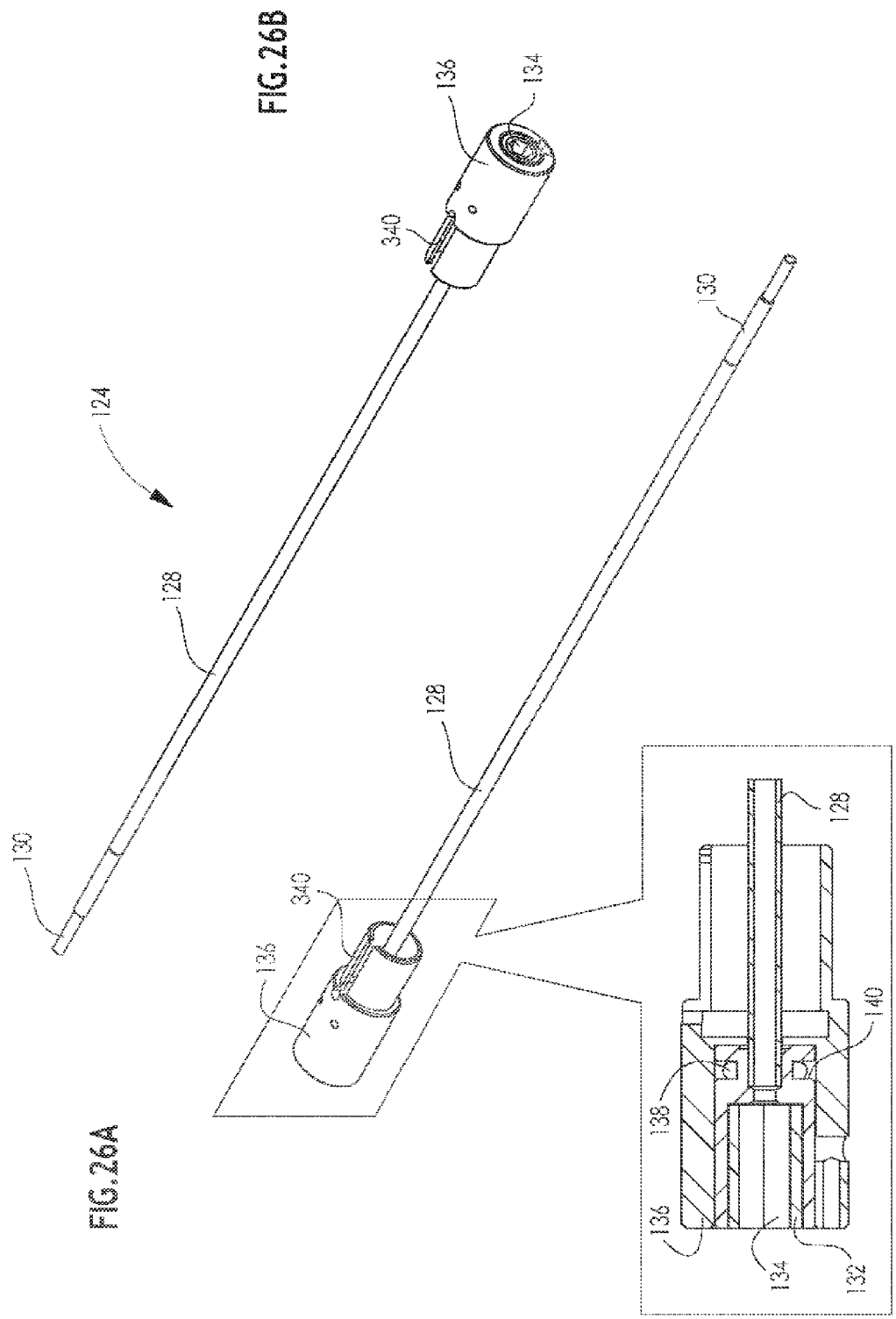

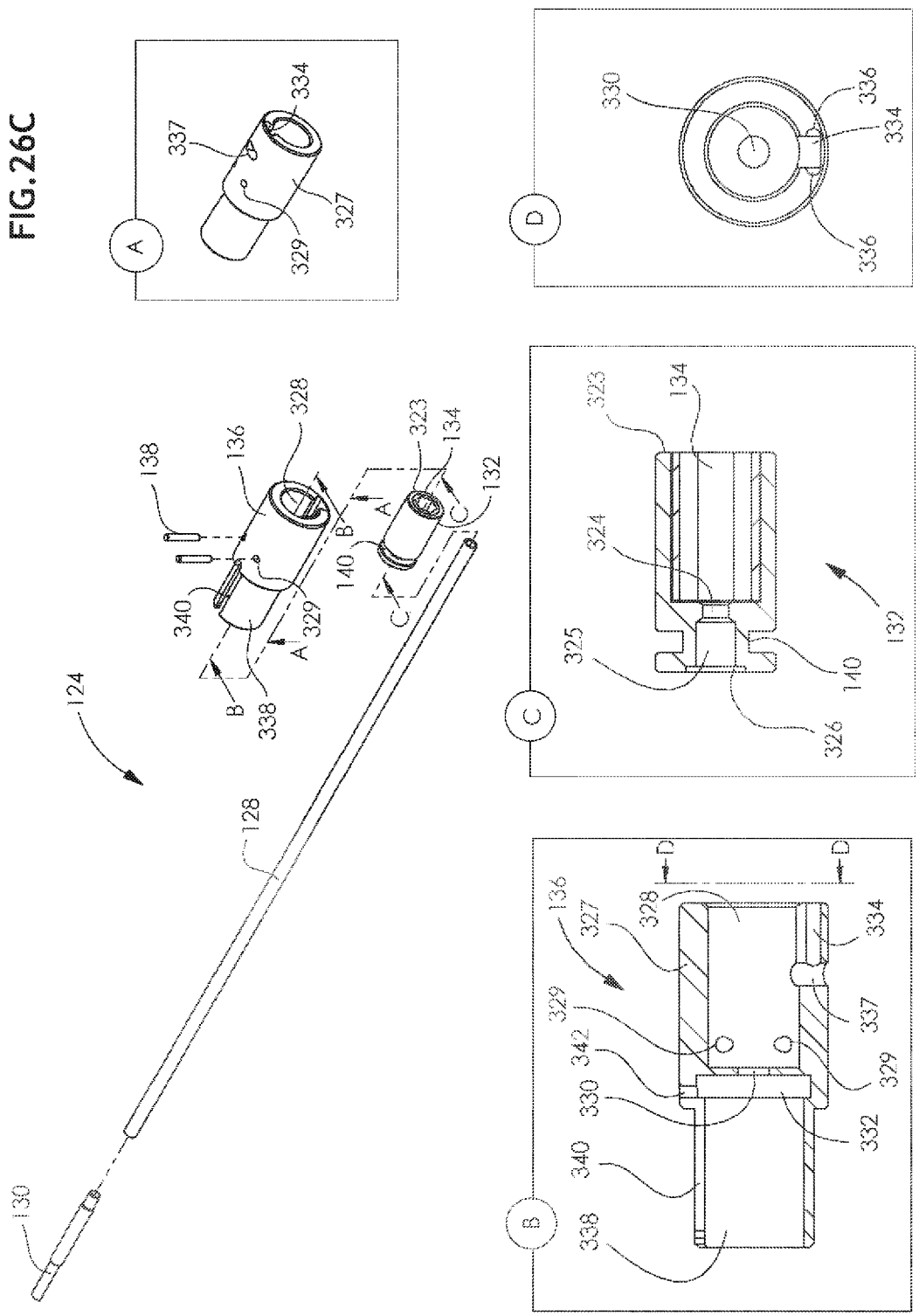

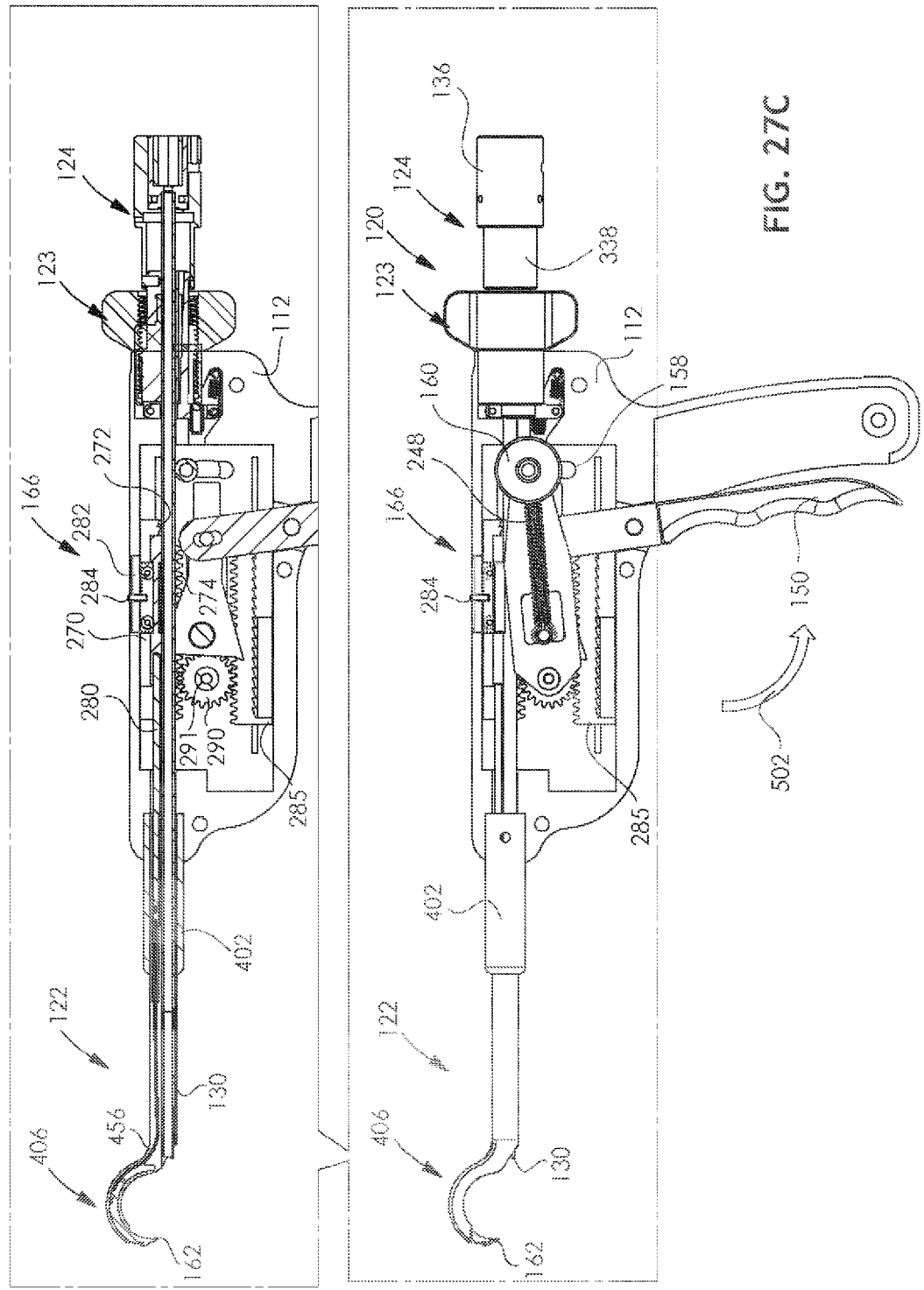

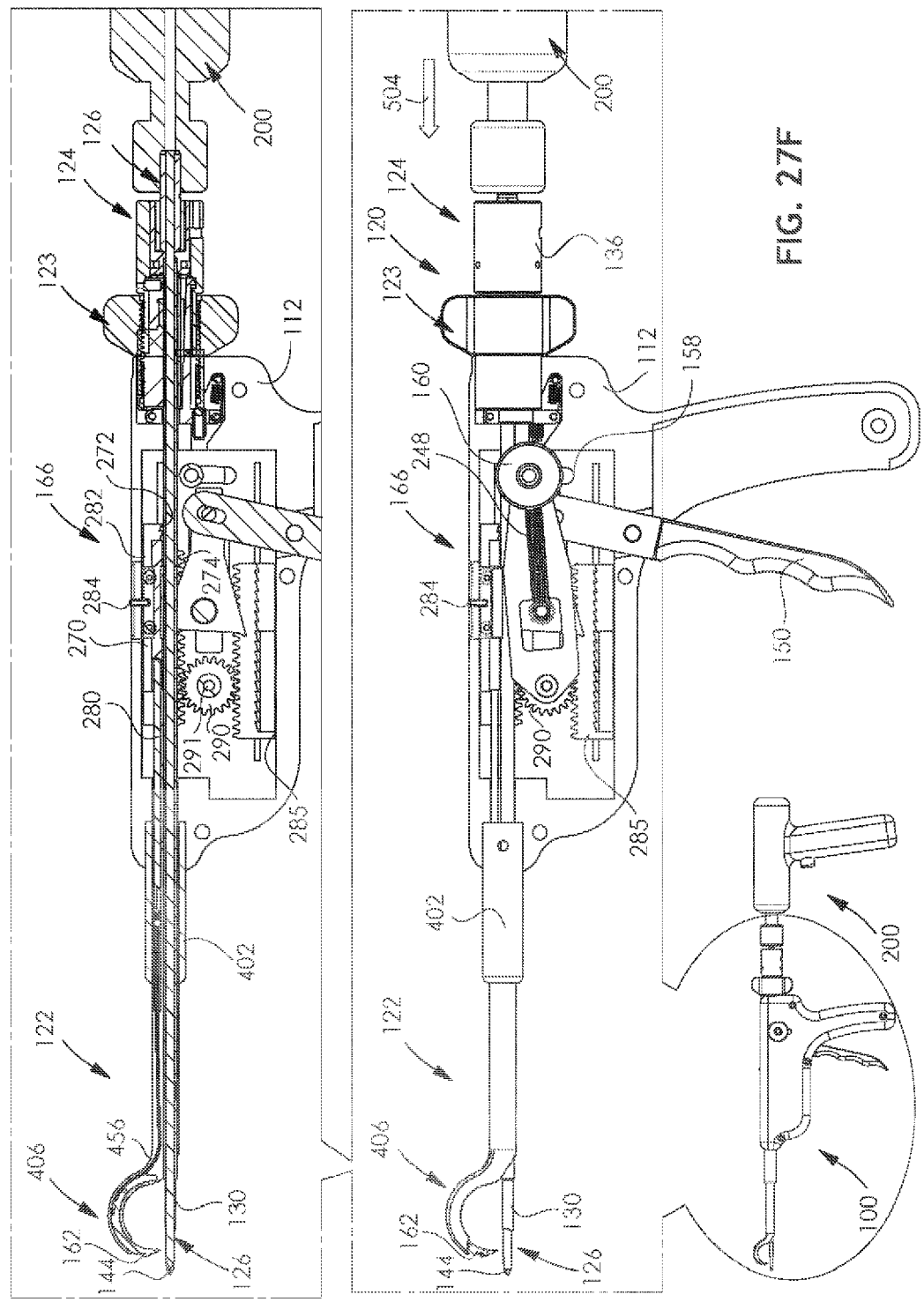

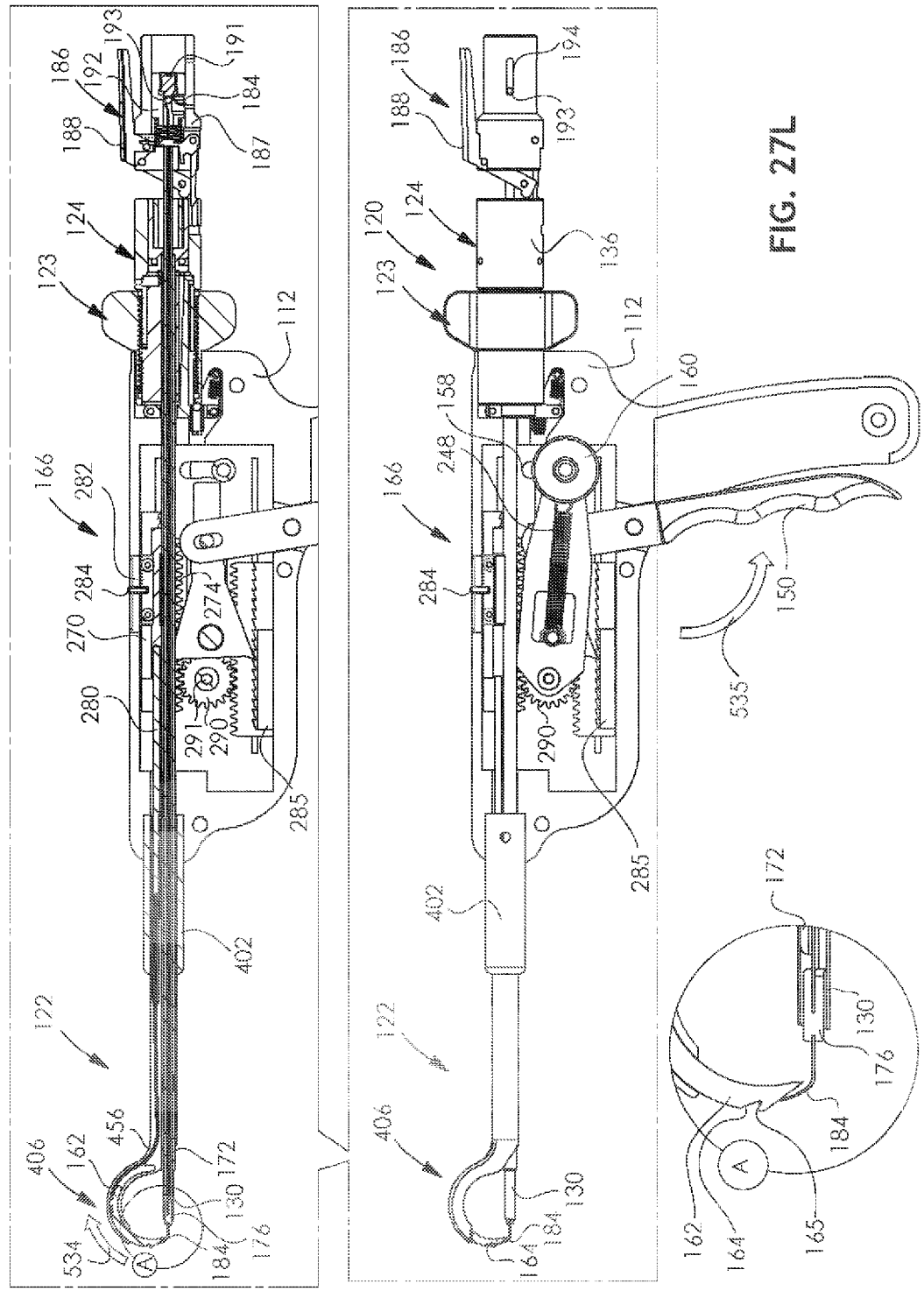

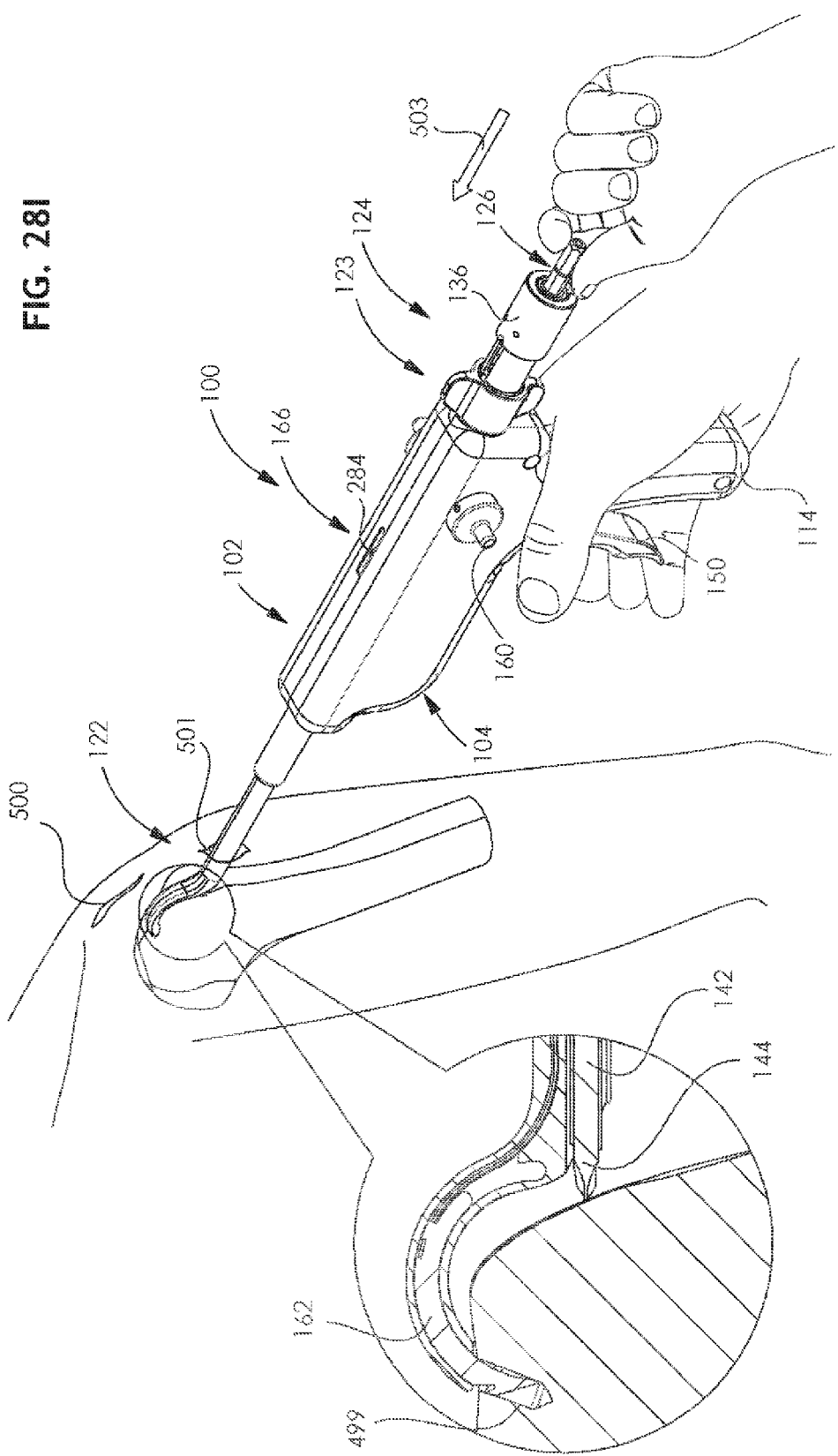

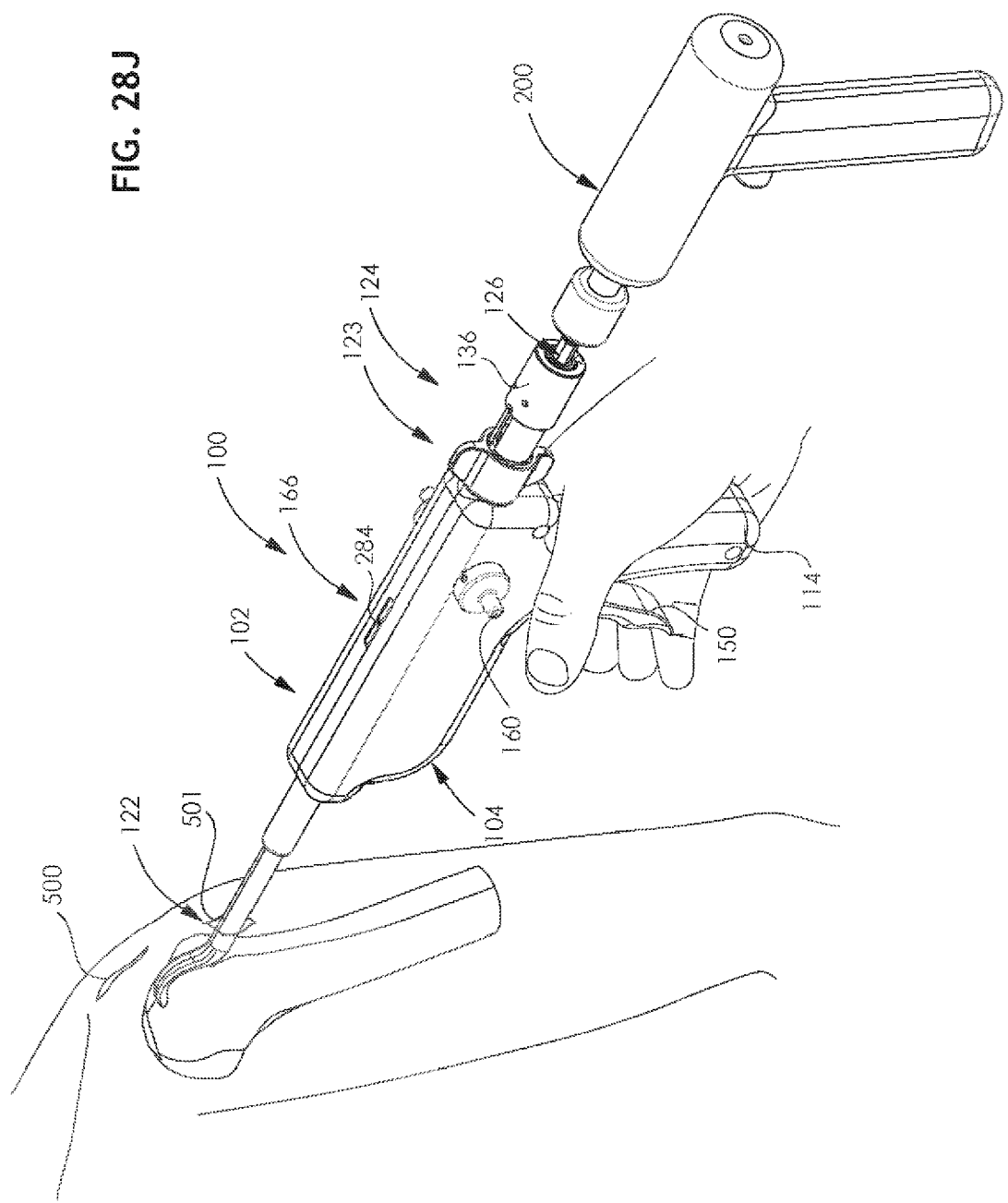

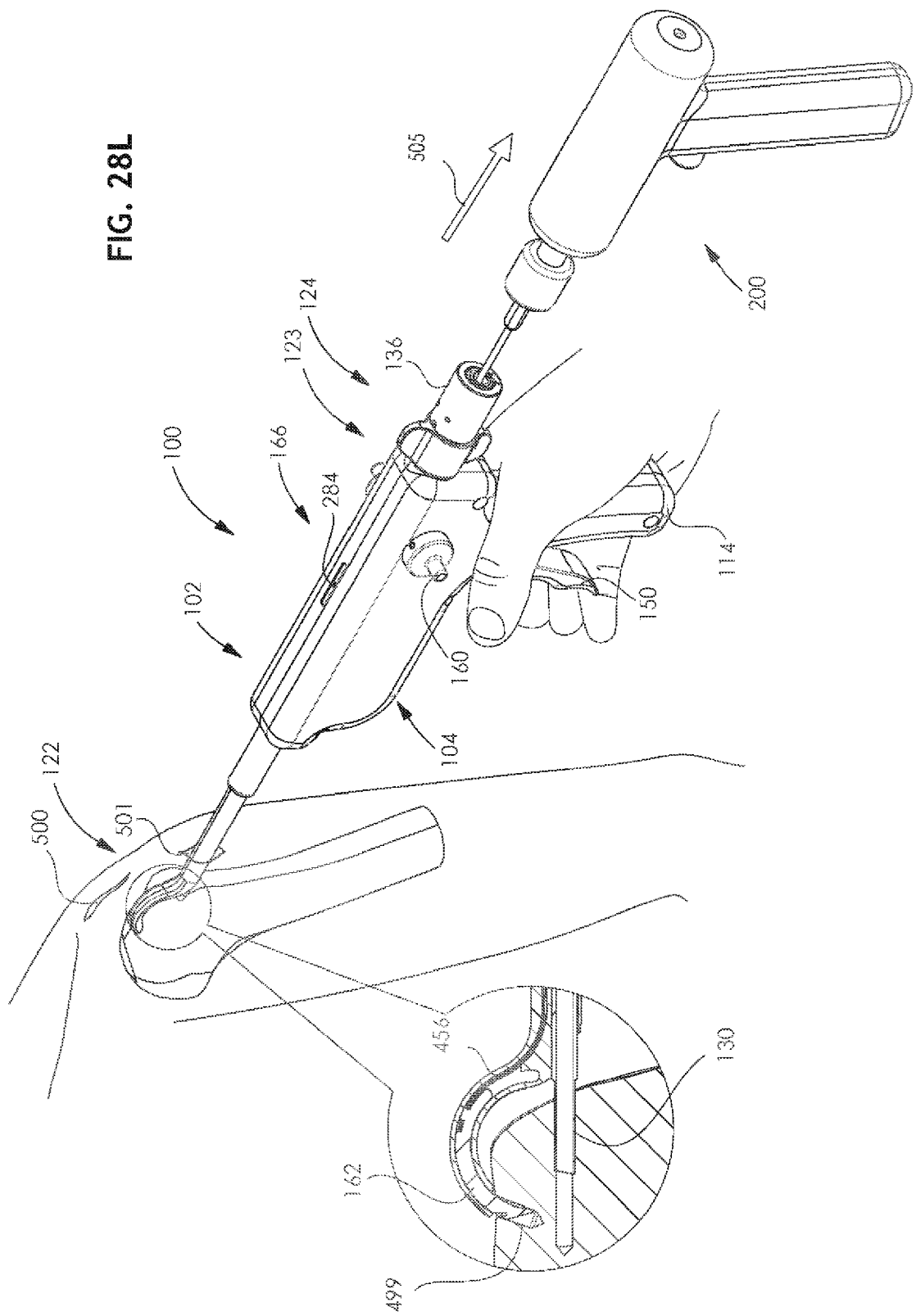

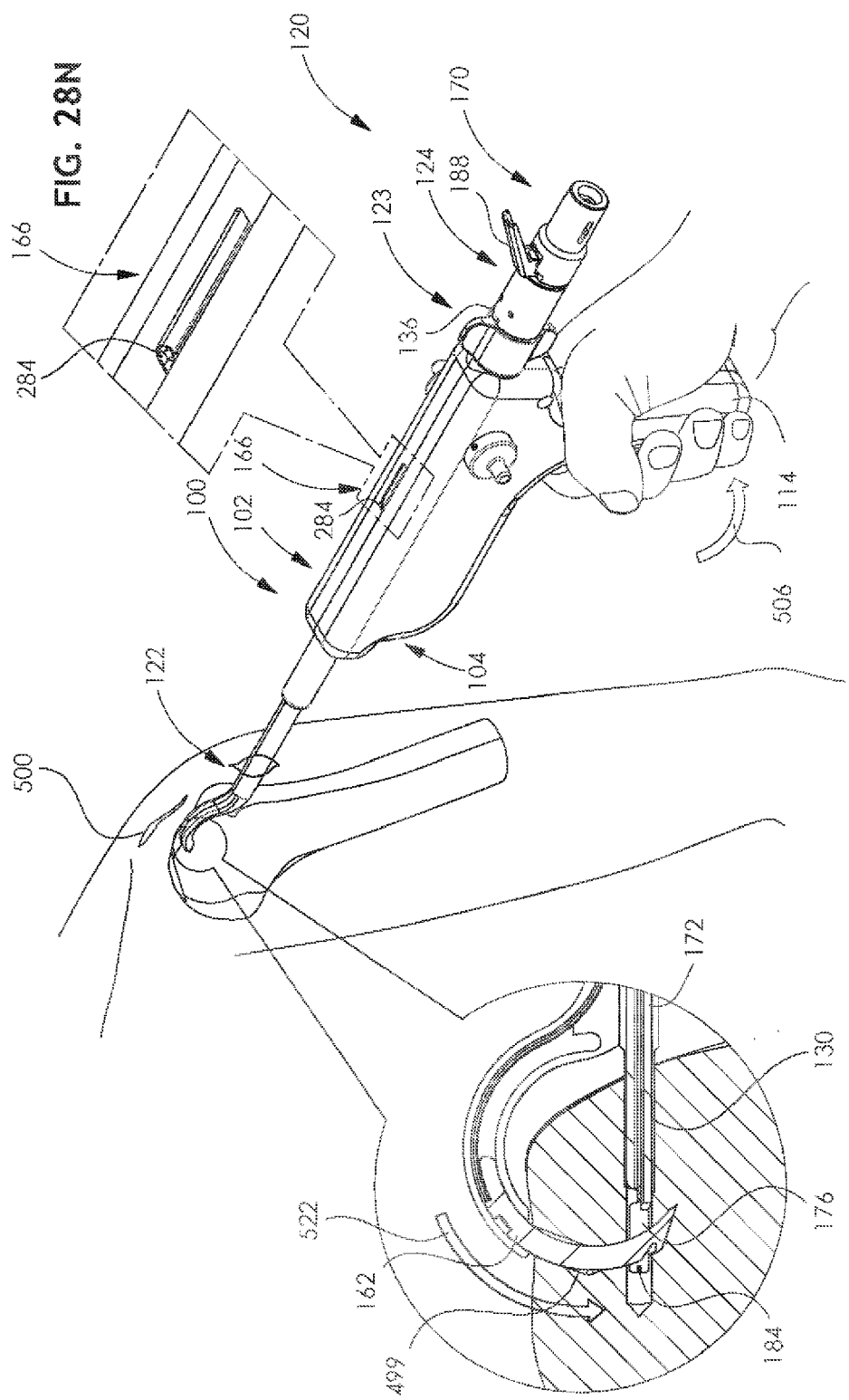

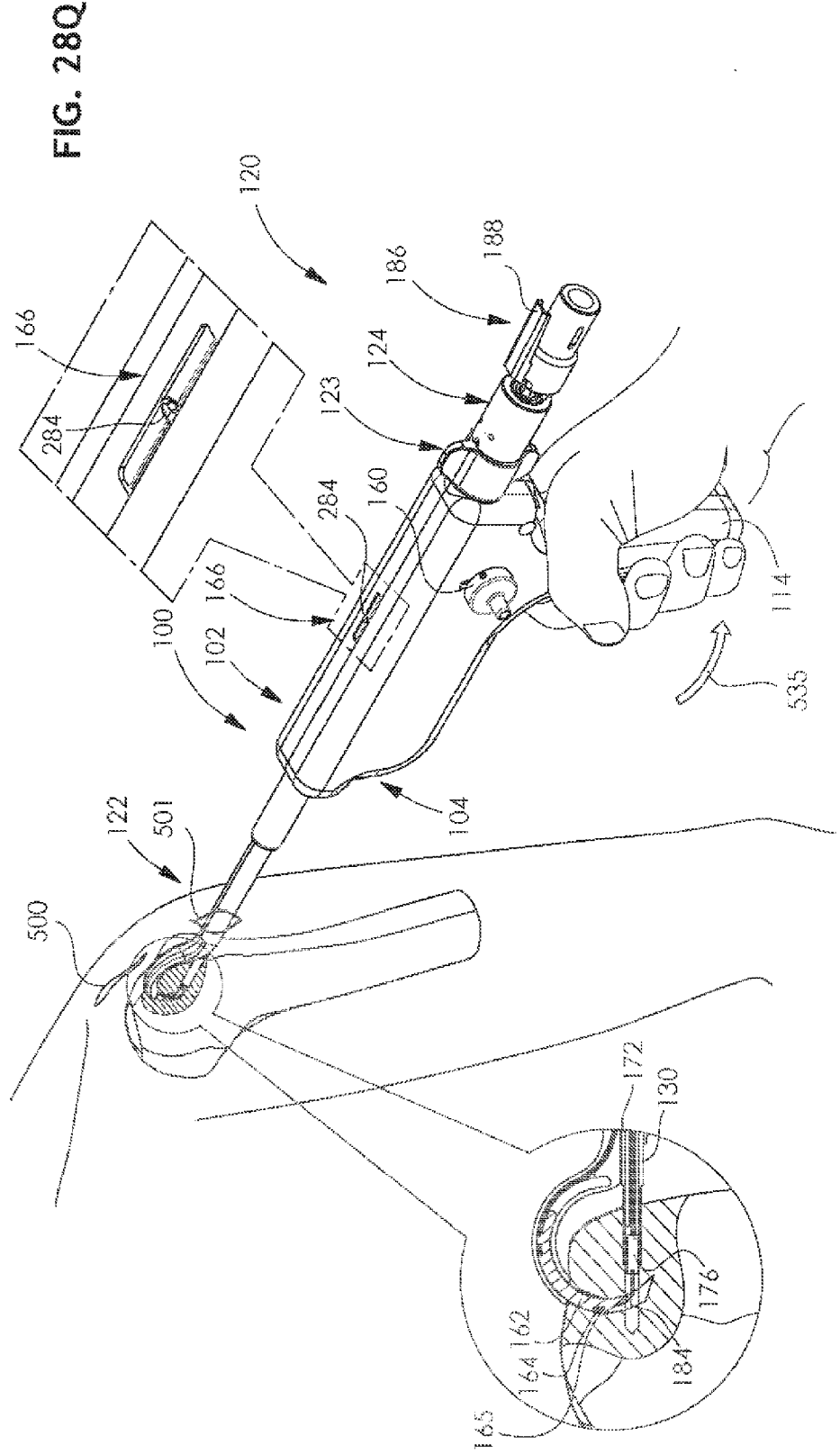

ARTHROSCOPIC SURGICAL DEVICE

REFERENCE TO RELATED APPLICATIONS

Reference is made to the following U.S. Provisional Patent Application which are believed to be related to the present application, the contents of which are hereby incorporated by reference herein and priority of which is hereby claimed under 37 CFR 1.78(a)(4) and (5)(i):

U.S. Provisional Patent Application Ser. No. 61/802,958, entitled "Arthroscopic Surgical Device" and filed Mar. 18, 2013.

U.S. Provisional Patent Application Ser. No. 61/887,561, entitled "Arthroscopic Surgical Device" and filed Oct. 7, 2013.

Reference is also made to the following PCT Patent Applications and U.S. Provisional Applications which are believed to be related to the present application, the contents of which are hereby incorporated by reference herein:

PCT Patent Application No. PCT/IL2013/050030, entitled "Arthroscopic Surgical Device" and filed Jan. 15, 2013;

PCT Patent Application No. PCT/IL2012/000318, entitled "Arthroscopic Surgical Device" and filed Aug. 23, 2012;

PCT Patent Application No. PCT/IL2012/000319, entitled "Circular Bone Tunneling Device Employing a Stabilizing Element" and filed Aug. 23, 2012;

Published PCT Patent Application No. WO 2012/007941, entitled "Circular Bone Tunneling Device" and filed Jul. 11, 2011;

U.S. Provisional Patent Application Ser. No. 61/636,751, entitled "Circular Bone Tunneling Device Employing a Stabilizing Element" and filed Apr. 23, 2012;

U.S. Provisional Patent Application Ser. No. 61/526,717, entitled "Circular Bone Tunneling Device" and filed Aug. 24, 2011;

U.S. Provisional Patent Application Ser. No. 61/714,813, entitled "Arthroscopic Surgical Device" and filed Oct. 17, 2012; and U.S. Provisional Patent Application Ser. No. 61/584,267, entitled "Circular Bone Tunneling Device" and filed Jan. 8, 2012.

FIELD OF THE INVENTION

The present invention relates generally to arthroscopic surgical devices and more particularly to arthroscopic bone tunneling devices.

BACKGROUND OF THE INVENTION

Various types of arthroscopic surgical instruments are known for various applications including orthopedic surgery.

SUMMARY OF THE INVENTION

It is appreciated that the terms 'tunnel' and 'channel' are used interchangeably in the description of the present invention and refer to a hollow bore, such as a cylindrically circular hollow bore, formed in a bone. It is also appreciated that the terms 'tunneling' and 'channeling' are used interchangeably in the description of the present invention and refer to a method of forming a hollow bore, such as a cylindrically circular hollow bore, in a bone.

It is further appreciated that the term "suture" as used throughout the description of the present invention refers to any suitable suture and also refers to a transfer wire which is used to pull a suture through the bone. Typically, a transfer wire is used with the system and method of the present invention and is formed of Nitinol. Typically, a transfer wire used with the system and method of the present invention is folded over to form a loop at one end.

The present invention seeks to provide an improved arthroscopic bone tunneling and suturing device.

There is thus provided in accordance with a preferred embodiment of the present invention an arthroscopic bone channel forming and suturing method including forming a first generally straight channel in a bone, inserting a curved needle into the first generally straight channel, forming a second generally straight channel in the bone, the second generally straight channel not intersecting the first generally straight channel, inserting a suture through the second generally straight channel in the bone to a suture pick-up location, manipulating the curved needle to form a curved junction between the first generally straight channel and the second generally straight channel and pulling the suture by the curved needle from the suture pick-up location through the junction and though the first generally straight channel.

Preferably, the inserting the suture includes locating a folded over end of the suture at the suture pick-up location. Additionally or alternatively, free ends of the suture extend outside of the second channel.

In accordance with a preferred embodiment of the present invention the second generally straight channel is substantially longer than the first generally straight channel.

Preferably, the curved needle has a radius of curvature which is generally equal to or greater than a length of the first generally straight channel. Additionally or alternatively, the geometry of the curved needle and the geometry of the first generally straight channel are such that the curved needle can pass through the first generally straight channel without changing the configuration of the first generally straight channel to add curvature thereto. Additionally, the geometry of the curved needle includes its width and its inner and outer radii of curvature and wherein the geometry of the first generally straight channel includes its width and its length.

There is also provided in accordance with another preferred embodiment of the present invention an arthroscopic bone channel forming and suturing system including a punch configured to form a first generally straight channel in a bone, a drill configured to form a second generally straight channel in the bone, the second generally straight channel not intersecting the first generally straight channel, a curved needle configured to be insertable into the first generally straight channel, a needle driving assembly configured to manipulate the curved needle to form a curved junction between the first generally straight channel and the second generally straight channel and a suture assembly configured to insert a suture to a suture pick-up location via the second generally straight channel in the bone, the curved needle being configured to pull the suture from the suture pick up location and through the junction and the first generally straight channel.

Preferably, the curved needle has a radius of curvature which is generally equal to or greater than a length of the first generally straight channel.

There is further provided in accordance with yet another preferred embodiment of the present invention an arthroscopic bone channel forming and suturing method including forming a first channel in a bone, inserting a curved needle into the first channel, forming a second channel in the bone by using a straight drill extending through a straight working channel, removing the drill from the working channel, inserting a suture through the working channel extending through the second channel in the bone to a suture pick-up location and pulling the suture by the curved needle from the suture pick-up location though the first channel.

Preferably, the method also includes forming a single incision in a patient's body for insertion and removal of the curved needle and the drill. Additionally, the inserting a suture includes locating a folded over portion of the suture at the suture pick-up location and free ends of the suture remain outside of the incision.

In accordance with a preferred embodiment of the present invention the second channel is substantially longer than the first channel.

Preferably, the curved needle has a radius of curvature which is generally equal to or greater than a length of the first channel. Additionally or alternatively, the geometry of the curved needle and the geometry of the first channel are such that the curved needle can pass through the first channel without changing the configuration of the first channel to add curvature thereto. Additionally, the geometry of the curved needle includes its width and its inner and outer radii of curvature and wherein the geometry of the first channel includes its width and its length.

There is even further provided in accordance with still another preferred embodiment of the present invention an arthroscopic bone channeling and suturing system including a punch configured to form a first channel in a bone, a straight drill extending through a straight working channel and being adapted to form a second channel and to insert the working channel in the straight channel in the bone, a needle driving assembly configured to insert a tunneling needle into the first channel and a suture assembly configured to insert a suture through the working channel and through the second channel in the bone to a suture pick-up location, the needle driving assembly being configured to retract the tunneling needle together with the suture from the suture pick-up location though the first channel.

Preferably, the drill is removable from the working channel to allow insertion of the suture assembly into the working channel. Additionally or alternatively, the drill is formed with a drill bit configuration at a forward end thereof.

In accordance with a preferred embodiment of the present invention the suture assembly includes a pair of forward arms and the suture looped over the pair of forward arms.

In accordance with a preferred embodiment of the present invention the needle driving assembly is configured to drive the tunneling needle through the bone from the first channel to the suture pick-up location.

Preferably, the tunneling needle includes a suture engagement groove configured to retain the suture and pull the suture from the suture pick-up location through the first channel. Additionally, the arthroscopic bone channeling and suturing device also includes a suture tensioning assembly and the suture is configured to slide into engagement with the suture engagement groove by tension provided by the tensioning assembly.

BRIEF DESCRIPTION OF THE DRAWINGS

The present invention will be understood and appreciated from the following detailed description, taken in conjunction with the drawings in which:

FIGS. 1A & 1B are simplified pictorial illustrations of an arthroscopic surgical assembly constructed and operative in accordance with a preferred embodiment of the present invention, showing opposite views;

FIGS. 2A & 2B are simplified pictorial illustrations of an arthroscopic surgical device forming part of the arthroscopic surgical assembly of FIGS. 1A & 1B, constructed and operative in accordance with a preferred embodiment the present invention, showing opposite views in a first operative orientation;

FIGS. 3A & 3B are simplified pictorial illustrations of an arthroscopic surgical device constructed and operative in accordance with a preferred embodiment of the present invention, showing opposite views in a second operative orientation;

FIGS. 4A & 4B are simplified pictorial illustrations of an arthroscopic surgical device constructed and operative in accordance with a preferred embodiment of the present invention, showing opposite views third operative orientation;

FIGS. 5A & 5B are simplified pictorial illustrations of an arthroscopic surgical device constructed and operative in accordance with a preferred embodiment of the present invention, showing opposite views in a fourth operative orientation;

FIGS. 6A & 6B are simplified pictorial illustrations of an arthroscopic surgical device constructed and operative in accordance with a preferred embodiment of the present invention, showing opposite views in a fifth operative orientation;

FIGS. 7A & 7B are simplified pictorial illustrations of an arthroscopic surgical device constructed and operative in accordance with a preferred embodiment of the present invention, showing opposite views in a sixth operative orientation;

FIGS. 8A & 8B are simplified pictorial illustrations of an arthroscopic surgical device constructed and operative in accordance with a preferred embodiment of the present invention, showing opposite views in a seventh operative orientation;

FIGS. 9A & 9B are simplified pictorial illustrations of an arthroscopic surgical device constructed and operative in accordance with a preferred embodiment of the present invention, showing opposite views in an eighth operative orientation;

FIGS. 10A & 10B are simplified pictorial illustrations of an arthroscopic surgical device constructed and operative in accordance with a preferred embodiment of the present invention, showing opposite views in a ninth operative orientation;

FIGS. 11A & 11B are simplified pictorial illustrations of an arthroscopic surgical device constructed and operative in accordance with a preferred embodiment of the present invention, showing opposite views in a tenth operative orientation;

FIGS. 12A & 12B are simplified pictorial illustrations of an arthroscopic surgical device constructed and operative in accordance with a preferred embodiment of the present invention, showing opposite views in an eleventh operative orientation;

FIGS. 13A & 13B are simplified pictorial illustrations of an arthroscopic surgical device constructed and operative in accordance with a preferred embodiment of the present invention, showing opposite views in a twelfth operative orientation;

FIGS. 14A & 14B are simplified pictorial illustrations of an arthroscopic surgical device constructed and operative in accordance with a preferred embodiment of the present invention, showing opposite views in an thirteenth operative orientation;

FIGS. 15A & 15B are simplified pictorial illustrations of an arthroscopic surgical device constructed and operative in accordance with a preferred embodiment of the present invention, showing opposite views in a fourteenth operative orientation;

FIGS. 16A & 16B are simplified pictorial illustrations of an arthroscopic surgical device constructed and operative in accordance with a preferred embodiment of the present invention, showing opposite views in a fifteenth operative orientation;

FIGS. 17A & 17B are simplified pictorial illustrations of an arthroscopic surgical device constructed and operative in accordance with a preferred embodiment of the present invention, showing opposite views in a sixteenth operative orientation;

FIGS. 18A & 18B are simplified pictorial illustrations of an arthroscopic surgical device constructed and operative in accordance with a preferred embodiment of the present invention, showing opposite views in a seventeenth operative orientation;

FIGS. 20D and 20E are simplified illustrations of the apparatus of FIGS. 20A-20C in two different operative orientations;

FIGS. 21A and 21B are simplified illustrations of another portion of the arthroscopic surgical device of FIGS. 1A-19C, showing opposite views;

FIGS. 22A and 22B are simplified exploded view illustrations of the portion of the arthroscopic surgical device of FIGS. 21A & 21B, showing opposite views;

FIGS. 23A and 23B are simplified illustrations of part of the portion of the arthroscopic surgical device of FIGS. 21A & 21B;

FIGS. 24A and 24B are simplified assembled view illustrations of a drill portion of the arthroscopic surgical device of FIGS. 1A-19C, showing opposite views;

FIGS. 25A and 25B are simplified assembled view illustrations of a suture cartridge portion of the arthroscopic surgical device of FIGS. 1A-24B, showing opposite views;

FIG. 25D is a simplified side view illustration of the suture cartridge portion of the arthroscopic surgical device shown in FIGS. 25A-25C;

FIGS. 26A and 26B are simplified assembled view illustrations of a working channel portion of the arthroscopic surgical device of FIGS. 1A-25D, showing opposite views;

FIG. 26C is a simplified exploded view illustration of the working channel portion of the arthroscopic surgical device shown in FIGS. 26A and 26B;

FIGS. 27A, 27B, 27C, 27D, 27E, 27F, 27G, 27H, 27I, 27J, 27K, 27L, 27M, 27N, 27O, 27P, 27Q and 27R are respective simplified illustrations of details of the operation of the arthroscopic surgical device of FIGS. 1A-26C; and FIGS. 28A, 28B, 28C, 28D, 28E, 28F, 28G, 28H, 28I, 28J, 28K, 28L, 28M, 28N, 28O, 28P, 28Q, 28R, 28S, 28T, 28U, 28V, 28W and 28X are simplified illustrations of operation of the arthroscopic surgical device of FIGS. 1A-27R in a clinical context.

DETAILED DESCRIPTION OF PREFERRED EMBODIMENTS

Figure 19A:
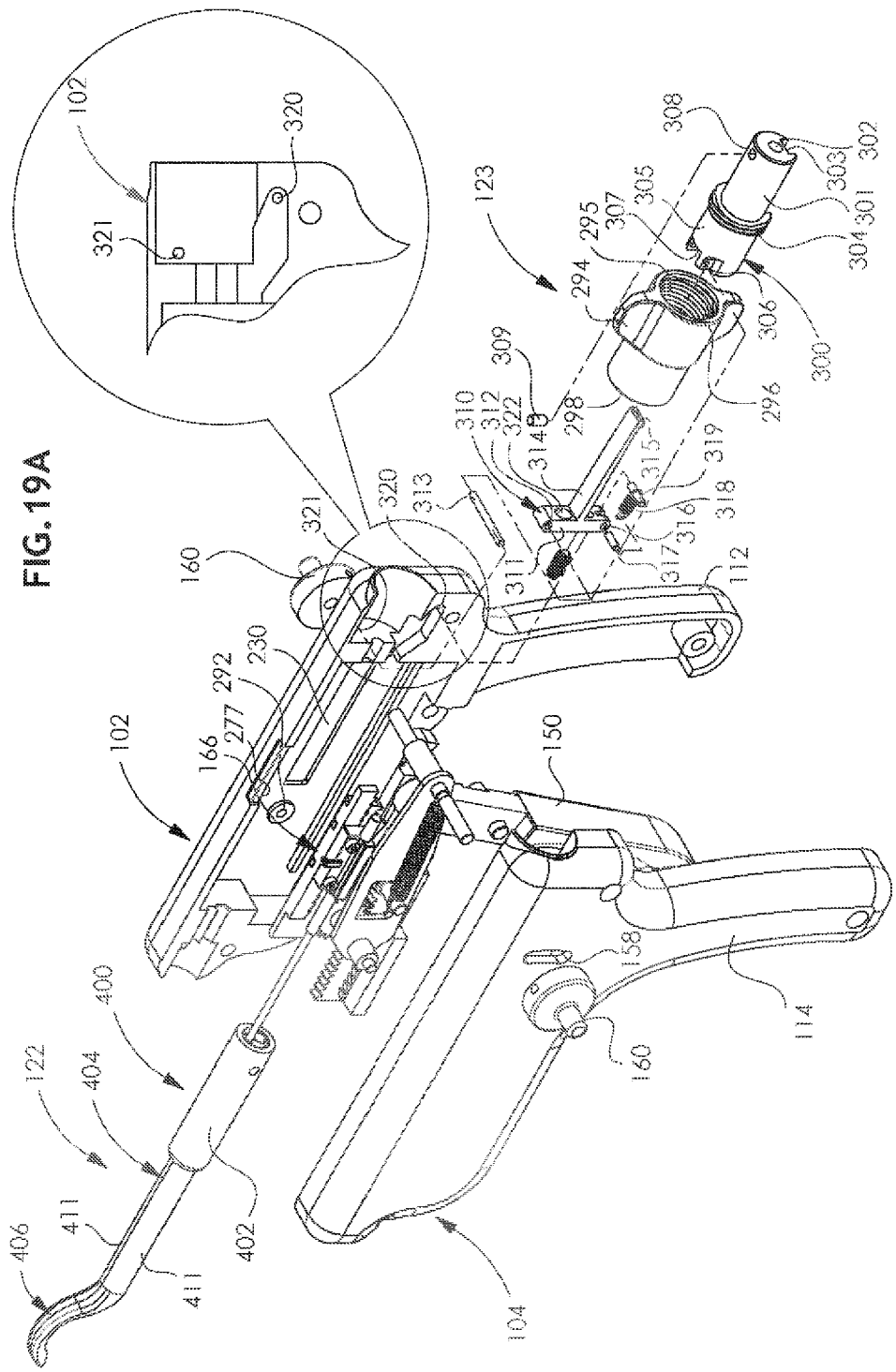
FIGS. 19A and 19B are respectively a simplified partially exploded view illustration of part of the arthroscopic surgical device of FIGS. 1A-18B in the first operative orientation and a fully exploded view illustration of a portion of the part of the device shown in FIG. 19A.

It is appreciated that the terms 'tunnel' and 'channel' are used interchangeably in the description of the present invention and refer to a hollow bore, such as a cylindrically circular hollow bore, formed in a bone. It is also appreciated that the terms 'tunneling' and 'channeling' are used interchangeably in the description of the present invention and refer to a method of forming a hollow bore, such as a cylindrically circular hollow bore, in a bone.

It is further appreciated that the term "suture" as used throughout the description of the present invention refers to any suitable suture and also refers to a transfer wire which is used to pull a suture through the bone. Typically, a transfer wire is used with the system and method of the present invention and is formed of Nitinol. Typically, a transfer wire used with the system and method of the present invention is folded over to form a loop at one end.

Reference is now made to FIGS. 1A & 1B, which are simplified pictorial illustrations of an arthroscopic surgical assembly, constructed and operative in accordance with a preferred embodiment of the present invention, showing opposite views, and to various additional drawings which are specifically referenced in parentheses hereinbelow.

As seen in FIG. 1B, there is provided a bone punch 10, preferably including a handle portion 12, an intermediate portion 14, and a forward portion 16, having a pointed tip 18. A line 20 is preferably formed on forward portion 16 to indicate a desired extent of bone penetration to a surgeon using the punch. A generally concave impact surface 22 is preferably formed on a rearward end of punch 10, for impact thereon by a surgical hammer.

As seen in FIGS. 1A & 1B and shown specifically in FIGS. 2A & 2B, an arthroscopic surgical device 100 according to a preferred embodiment of the present invention includes a housing portion, preferably formed of right and left housing elements 102 and 104, and a multiple action driving assembly 106, only part of which is seen in FIGS. 1A & 1B. The housing portion includes a handle portion, which is defined by respective right and left housing element handle portions 112 and 114, respectively.

The multiple action driving assembly 106 preferably includes a bone-engaging pin insertion assembly 120, a bone-engaging needle driving assembly 122 and a selectable attachment assembly 123.

Bone-engaging pin insertion assembly 120 preferably includes a working channel assembly 124, which is shown and described in detail hereinbelow with reference to FIGS. 26A-26C, and a drill 126, which is shown and described in detail hereinbelow with reference to FIGS. 24A & 24B.

Referring now additionally to FIGS. 26A-26C, it is seen that the working channel assembly 124 includes a main longitudinal rigid tube 128, typically formed of stainless steel, and a hardened forward tube 130, typically formed of hardened stainless steel, which fits into a forward end of main rigid tube 128. Preferably, welded onto a rear end of main tube 128 is a driving socket element 132 having formed, at a rear end thereof, a recess 134, typically having a hexagonal cross section.

Driving socket element 132 is rotatably mounted within a collar member 136, which is shown and described in detail hereinbelow, with reference to FIGS. 19A & 19B, and which is mounted onto the housing so as to have limited axial movement with respect thereto. Driving socket element 132 is restrained against axial movement relative to collar member 136, preferably by a pair of retaining pins 138, which extend through transverse apertures formed in collar member 136 and engage a groove 140 formed in driving socket element 132.

Referring now additionally to FIGS. 24A-24B, it is seen that drill 126 preferably comprises a solid rod 142 of circular cross section, having a drill bit configuration at a forward end 144 thereof and being formed at a widened rear end 146 thereof with a hexagonal cross section, such that rear end 146 is suitable for drivable engagement with a chuck of a conventional surgical drill (not shown).

Figure 19B:
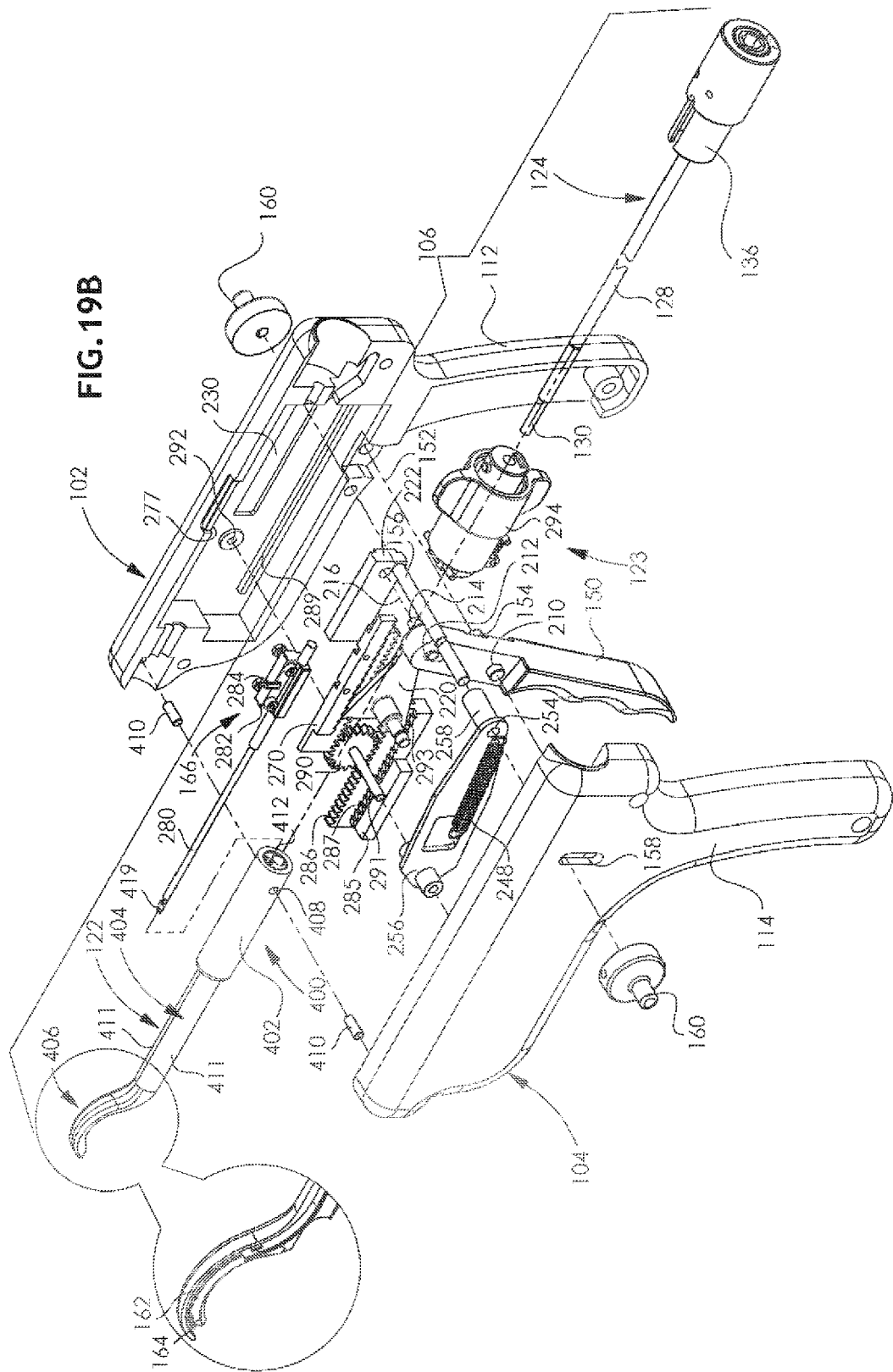
Figure 19C:
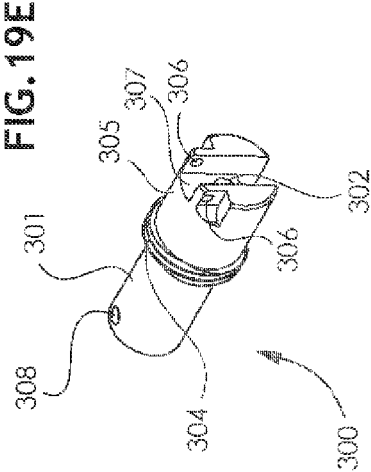
FIG. 19C is a simplified illustration of another part of the arthroscopic surgical device of FIGS. 1A-19B.
Figure 19E:
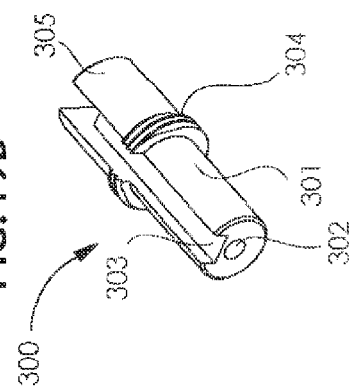
FIGS. 19D and 19E are simplified illustrations, from two different perspectives, of another part of the arthroscopic surgical device of FIGS. 1A-19B.
Figure 19D:
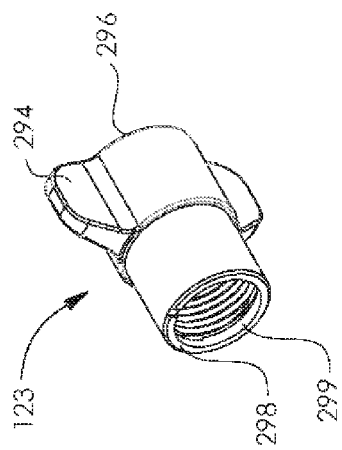
Figure 19F:
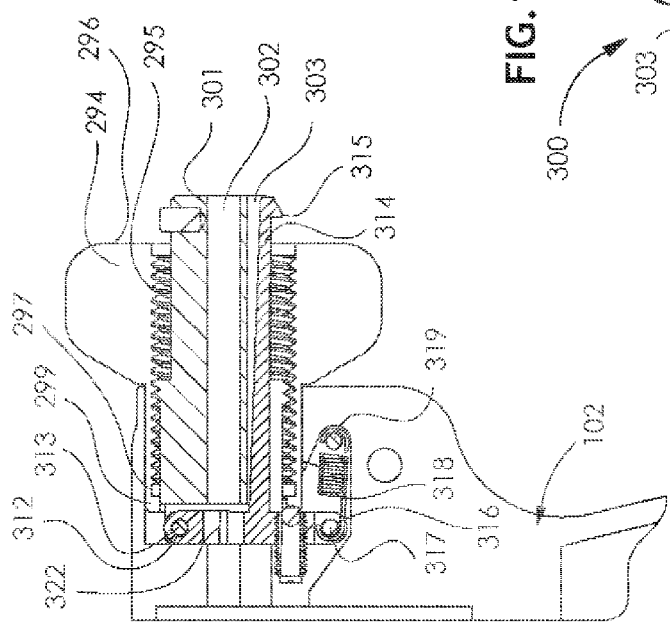
FIG. 19F is a simplified sectional view of a portion of the arthroscopic surgical device of FIGS. 1A-19B.

The bone-engaging needle driving assembly 122 preferably includes a hand-engageable ratchet handle 150 which is arranged for reciprocal motion about an axis 152 (FIG. 19B). A selectable direction ratchet shaft 156 (FIG. 19B) extends through slots 158 in respective right and left housing element handle portions 112 and 114, and terminates in knobs 160, whose positions in slots 158 govern the direction of motion of an arthroscopic arcuate tunneling needle 162 having a suture engagement groove 164 partially defined by a needle end portion 165.

As noted above, it is appreciated that the terms 'tunneling' and channeling' are used interchangeably in the description of the present invention and refer to a method of forming a hollow bore, such as a cylindrically circular hollow bore, in a bone.

A visible mechanical indicator 166 is preferably arranged on the top of respective housing portions 102 and 104. Indicator 166 preferably provides a visible indication of the extent that arcuate tunneling needle 162 is displaced from its fully retracted position shown in FIGS. 2A & 2B.

Figure 25C:
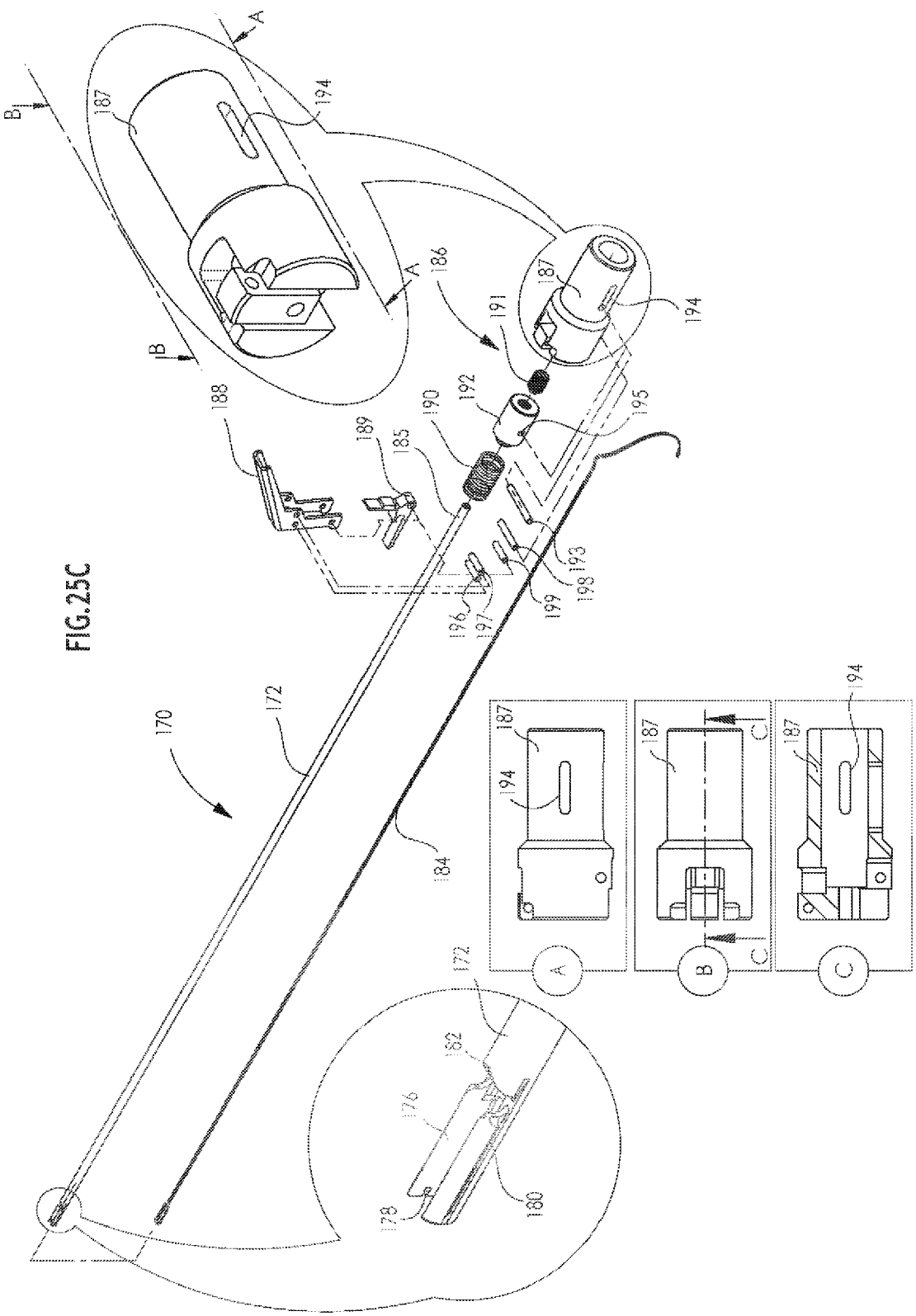
FIG. 25C is a simplified exploded view illustration of the suture cartridge portion of the arthroscopic surgical device shown in FIGS. 25A and 25B.

A suture cartridge assembly 170 is provided for selectable engagement with the housing and is illustrated in FIGS. 25A-25D. Suture cartridge assembly 170 preferably includes a longitudinal tube 172 having a specially configured forward end 174. As seen particularly in FIG. 25C, the forward end 174 is configured to have a pair of mutually spaced forwardly extending arms 176 which are each formed with a suture retaining end notch 178 and a suture retaining side notch 180. A transverse slot 182 is formed rearwardly of arms 176 to enable a folded over suture 184 which extends through a longitudinal bore in longitudinal tube 172 to be looped over arms 176 at notches 178 and 180 as shown in FIG. 25A.

As noted above, it is appreciated that the term "suture" as used throughout the description of the present invention refers to any suitable suture and also refers to a transfer wire which is used to pull a suture through the bone. Typically, a transfer wire is used with the system and method of the present invention and is formed of Nitinol.

Mounted at a rearward end 185 of tube 172, there is provided a selectable suture tensioning assembly 186. Assembly 186 includes an assembly housing 187 onto which is pivotably mounted a user-operable suture release lever 188, which, in turn, operates a pivotably mounted release element 189. Release element 189 selectably retains the assembly housing 187 against rearward axial movement under the urging of a compression spring 190. Frictional engagement between a screw 191, threaded into engagement with a retaining member 192, and a transversely extending rod 193 maintains tension on the suture 184 up to a predetermined threshold force beyond which the ends of the suture 184 become released from assembly 186. Rod 193 engages a pair of slots 194 on opposite sides of assembly housing 187 and extends through a transverse aperture 195 in retaining member 192.

A pivot pin 196 pivotably mounts release lever 188 onto assembly housing 187. A pusher pin 197, mounted onto release lever 188, engages release element 189 and produces pivoted movement thereof about a pivot pin 198, fixed to housing 187, in response to pressing on release lever 188. A latch pin 199, fixed onto assembly housing 187 selectably engages release element 189.

The operation of selectable suture tensioning assembly 186 may be summarized as follows. Insertion of the suture cartridge assembly 170 into engagement with collar member 136 causes release element 189 to be latched to collar member 136. Downward pushing on release lever 188 produces pivotal motion of release element 189, which pushes spring 190 rearwardly against retaining member 192. This produces retraction of tube 172 and of arms 176 and tensions the forward folded over end of suture 184 and draws it tightly into engagement with arcuate tunneling needle 162, which is adapted to selectably engage suture 184 at needle-suture engagement location located between arms 176. The free ends of the suture 184 thereafter become released from the suture tensioning assembly 186 in response to retraction of the needle 162 along its arcuate path, which produces tensile force on the suture 184 which overcomes the grip between rod 193 and screw 191 produced by spring 190.

It is appreciated that free ends of suture 184 remain outside of an incision made in a patient's body before, during and after the insertion procedure described hereinbelow with reference to FIGS. 27A-27R and 28A-28X.

Reference is now made to FIGS. 3A & 3B, which are simplified pictorial illustrations of the arthroscopic surgical device of FIGS. 1A-2B in a second operative orientation. It is seen that the transition from the first operative orientation of FIGS. 2A & 2B to the second operative orientation, which preferably occurs following insertion of a forward portion of the bone-engaging needle driving assembly 122 through an arthroscopic incision, as described hereinbelow with reference to FIGS. 28E and 27B, involves shifting the position of knobs 160 from a lowered position to a raised position in slot 158.

Reference is now made to FIGS. 4A & 4B, which are simplified pictorial illustrations of the arthroscopic surgical device of FIGS. 1A-3B in a third operative orientation and which illustrate partial extension of arcuate tunneling needle 162, as indicated by indicator 166. This extension is produced by rotation of hand-engageable ratchet handle 150 about axis 152 (FIG. 19B) when knobs 160 are in the upper position in slots 158. Needle 162 enters a channel earlier formed in a humerus, as will be described hereinbelow with reference to FIGS. 27C & 28H.

Reference is now made to FIGS. 5A & 5B, which are simplified pictorial illustrations of the arthroscopic surgical device of FIGS. 1A-4B in a fourth operative orientation and which show insertion of the bone-engaging pin insertion assembly 120 through the housing of the arthroscopic surgical device 100 of FIGS. 4A & 4B so that tip 144 extends nearly to the surface of the bone, as described hereinbelow with reference to FIGS. 27D and 28I.

Reference is now made to FIGS. 6A & 6B, which are simplified pictorial illustrations of the arthroscopic surgical device of FIGS. 1A-5B in a fifth operative orientation. It is seen that the widened rear end 146 of bone-engaging pin insertion assembly 120 is engaged by the chuck of a surgical drill 200, as described hereinbelow in detail with reference to FIGS. 27E and 28J.

Reference is now made to FIGS. 7A & 7B, which are simplified pictorial illustrations of the arthroscopic surgical device of FIGS. 1A-6B in a sixth operative orientation. It is seen that due to operation of surgical drill 200, the forward tip 144 of the drill 126 is fully extended, as described hereinbelow in detail with reference to FIGS. 27F and 28K. It is seen that concomitantly, due to the operation of surgical drill 200, working channel assembly 124, including collar member 136, has moved to its full axially forward position with respect to the selectable attachment assembly 123. It is noted, as will be described hereinbelow, that collar member 136 is automatically latched to selectable attachment assembly 123 at this stage.

Reference is now made to FIGS. 8A & 8B, which are simplified pictorial illustrations of the arthroscopic surgical device of FIGS. 1A-7B in a seventh operative orientation. Here it is seen that the drill 126 is being retracted but that working channel assembly 124 remains in its full axially forward position, by virtue of latching of collar member 136 to selectable attachment assembly 123.

Reference is now made to FIGS. 9A & 9B, which are simplified pictorial illustrations of the arthroscopic surgical device of FIGS. 1A-8B in an eighth operative orientation and illustrate insertion of the suture cartridge assembly 170 through the working channel assembly 124. It is noted that selectable suture tensioning assembly 186 is automatically latched to collar member 136.

Reference is now made to FIGS. 10A & 10B, which are simplified pictorial illustrations of the arthroscopic surgical device of FIGS. 1A-9B in a ninth operative orientation and which illustrate full extension of arcuate tunneling needle 162, as indicated by indicator 166. This extension is produced by rotation of hand-engageable ratchet handle 150 about axis 152 (FIG. 19B) when knobs 160 are in the upper position in slots 158.

It is seen that arcuate tunneling needle 162 extends between mutually spaced forwardly extending arms 176 of suture cartridge assembly 170. As noted above, each of arms 176 is formed with a suture retaining end notch 178 and a suture retaining side notch 180. A transverse slot 182 is formed rearwardly of arms 176 to enable a folded over suture 184 which extends through a longitudinal bore in longitudinal tube 172 to be looped over arms 176 at notches 178 and 180 as shown in FIG. 25A. It is further seen that suture engagement groove 164 lies below mutually spaced forwardly extending arms 176 of suture cartridge assembly 170.

Reference is now made to FIGS. 11A & 11B, which are simplified pictorial illustrations of the arthroscopic surgical device of FIGS. 1A-10B in a tenth operative orientation. It is seen that lever 188 is manually depressed, thereby unlatching suture tensioning assembly 170 from collar member 136 and causing axially rearward displacement of suture tensioning assembly 170 relative to collar member 136 and concomitant axial retraction of arms 176 of suture cartridge assembly 170 relative to working channel 124. It is seen that suture 184 is looped around needle 162 at a location on needle 162 lying above suture engagement groove 164.

Reference is now made to FIGS. 12A & 12B, which are simplified pictorial illustrations of the arthroscopic surgical device of FIGS. 1A-11B in an eleventh operative orientation. It is seen knobs 160 are lowered to their lower position in slots 158.

Reference is now made to FIGS. 13A & 13B, which are simplified pictorial illustrations of the arthroscopic surgical device of FIGS. 1A-12B in a twelfth operative orientation. It is seen that needle 162 is partially retracted so that it engages suture 184 at suture engagement groove 164.

Reference is now made to FIGS. 14A & 14B, which are simplified pictorial illustrations of the arthroscopic surgical device of FIGS. 1A-13B in a thirteenth operative orientation. It is seen that arcuate tunneling needle 162 is fully retracted, as indicated by indicator 166, in engagement with the forward looped end of suture 184, thus drawing the suture backwards along an arcuate path along with full retraction of the needle 162.

Reference is now made to FIGS. 15A & 15B, which are simplified pictorial illustrations of the arthroscopic surgical device of FIGS. 1A-14B in a fourteenth operative orientation. It is seen that suture cartridge assembly 170 is fully retracted and withdrawn from the working channel assembly 124, leaving the suture 184 in the working channel assembly 124.

Reference is now made to FIGS. 16A & 16B, which are simplified pictorial illustrations of the arthroscopic surgical device of FIGS. 1A-15B in a fifteenth operative orientation. It is seen that the working channel assembly 124 is partially axially retracted by rotation of the selectable attachment assembly 123, which forces collar member 136 axially rearwardly, thus drawing hardened forward tube 130 rearwardly out of tight engagement with the bone.

Reference is now made to FIGS. 17A & 17B, which are simplified pictorial illustrations of the arthroscopic surgical device of FIGS. 1A-16B in a sixteenth operative orientation. It is seen that working channel assembly 124 is fully retracted and that the positions of knobs 160 in slots 158 are shifted upwardly, in order to provide extension of needle 162 in response to operation of ratchet handle 150. The orientation of the needle 162 is shown by indicator 166.

Reference is now made to FIGS. 18A & 18B, which are simplified pictorial illustrations of the arthroscopic surgical device of FIGS. 1A-17B in a seventeenth operative orientation. It is seen that the arcuate tunneling needle 162 is now partially extended in order to permit manual disengagement of the looped forward end of suture 184 from suture engagement groove 164 of needle 162.

Figure 20A:
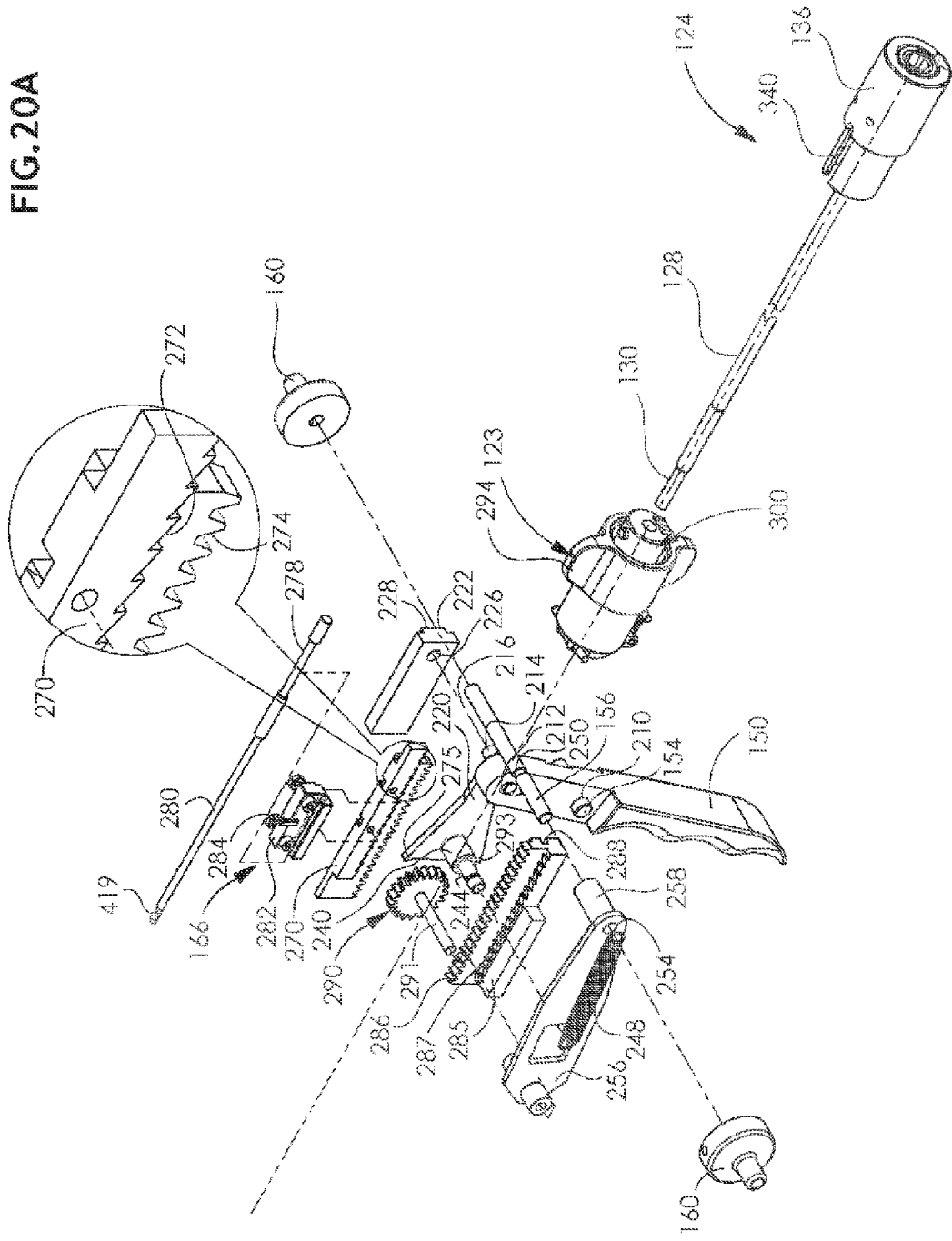
FIGS. 20A and 20B are simplified exploded view illustrations of a portion of the arthroscopic surgical device of FIGS. 1A-19F, showing opposite views.
Figure 20B:
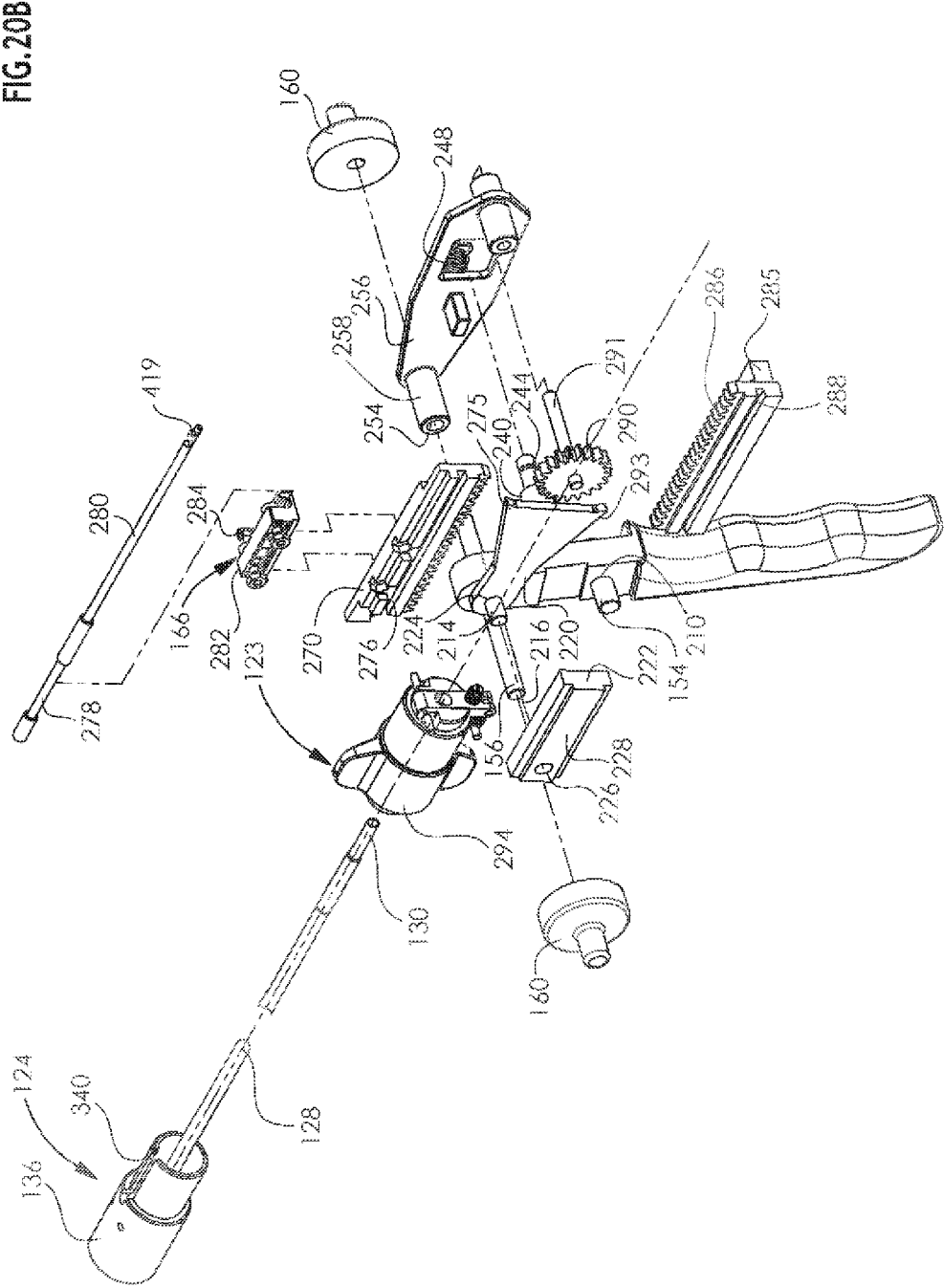
Figure 20C:
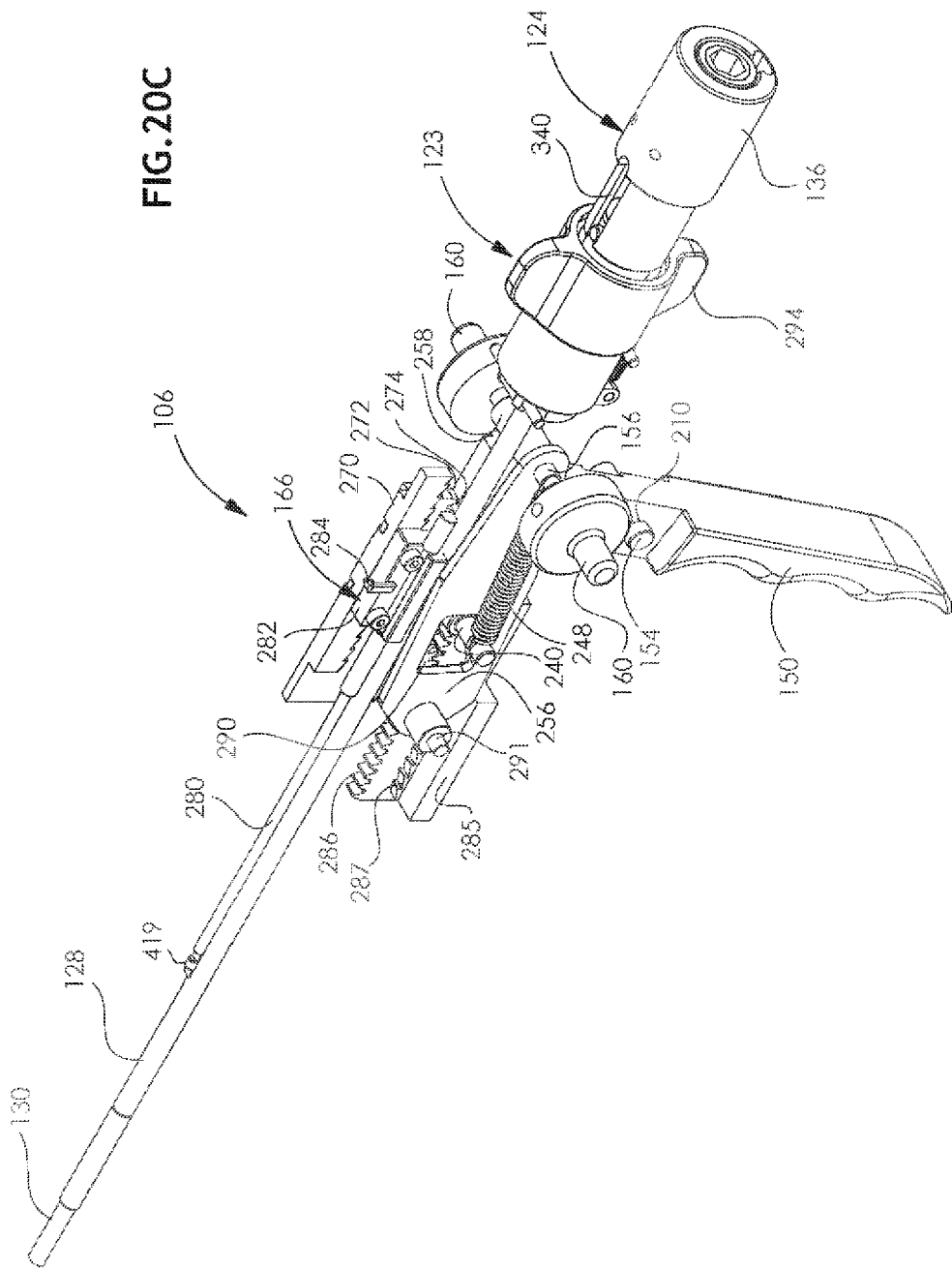
FIG. 20C is a simplified partially assembled view of the portion of the arthroscopic surgical device of FIGS. 20A and 20B.
Figure 20E:
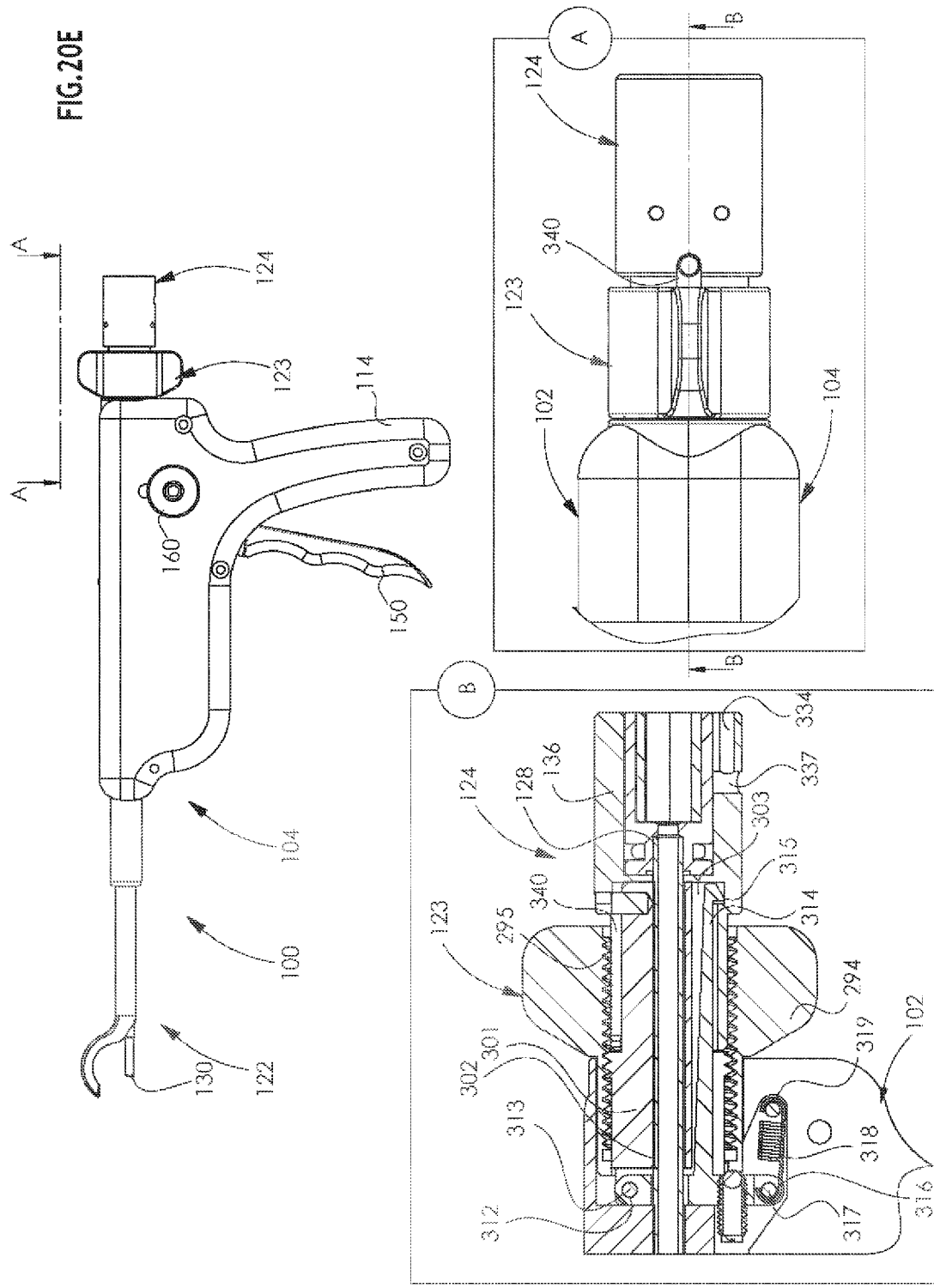

Reference is now made to FIGS. 19A-24B and initially specifically to FIGS. 19A & 19B and to FIGS. 20A and 20B, which are simplified exploded view illustrations of a portion of the arthroscopic surgical device of FIGS. 1A-18B, showing opposite views, to FIG. 20C, which is a simplified partially assembled view, and to FIGS. 20D and 20E, which are simplified illustrations of the apparatus of FIGS. 20A-20C in two different operative orientations, all of which show details of some elements of multiple action driving assembly 106.

It is seen that ratchet handle 150 is typically formed with a lower aperture 210, which accommodates a shaft 154, and a slot 212. A pin 214 is slidably movable in slot 212, such that reciprocal arcuate motion of slot 212 is translated into reciprocal planar forward and rearward motion perpendicular to a longitudinal axis 216 of pin 214. First and second reciprocal motion connection elements 220 and 222 are fixed to pin 214 at respective apertures 224 and 226 and move together therewith in reciprocal forward and rearward linear motion in response to rotational motion of ratchet handle 150.

Connection element 222 includes an elongate protrusion 228, which moves reciprocally in a slot 230 formed in housing portion 102.

Connection element 220 includes a side extending shaft 240 which is formed with a circumferential groove 244 onto which is mounted one end of a tension spring 248. An opposite end of tension spring 248 is mounted in a circumferential groove 250 formed in shaft 156. Shaft 156 extends through an aperture 254 formed in a toggle element 256, which communicates with a hollow shaft portion 258 of toggle element 256. Shaft 156 extends through slots 158 formed on respective housing portions 102 and 104.

A double rack linear toothed element 270 is provided with an upper linear toothed ratchet rack 272 and a lower linear toothed gear rack 274. A pointed corner 275 of connection element 220 selectably engages upper linear toothed rack 272. Double rack linear toothed element 270 is preferably formed with a slot 276 which engages an elongate axial protrusion 277 formed in housing element 102.

An inward recessed portion 278 adjacent an inner end of a generally rigid flexible needle driving strip driving shaft 280 is fixedly mounted onto double rack linear toothed element 270 by means of a mounting element 282, which is typically bolted onto element 270. An indicator finger 284 is formed on mounting element 282 and forms part of indicator 166.

A second double rack linear toothed element 285 is provided with an upper linear toothed gear rack 286 and a lower linear toothed ratchet rack 287. Double rack linear toothed element 285 is preferably formed with a slot 288, which engages an elongate axial protrusion 289 formed in housing element 102.

A gear 290, having a gear shaft 291, engages lower linear toothed gear rack 274 of element 270 and also simultaneously engages upper linear toothed gear rack 286 of element 285. Gear shaft 291 preferably is mounted at its opposite ends in apertures 292 in respective housing elements 102 and 104.

A pointed corner 293 of connection element 220 selectably engages lower linear toothed ratchet rack 287 of element 285.

Reference is now made specifically to FIGS. 19A-19F and 20A-20E, which illustrate the structure of selectable attachment assembly 123. As seen with particularity in FIGS. 19A, 19C & 19F, the selectable attachment assembly 123 comprises a winged nut 294 having a threaded bore 295 extending therealong from a first end 296 of nut 294 to a circumferential recess 297 which is spaced from a second end 298 of nut 294 by a non-threaded bore portion 299.

As seen in FIGS. 19A and 19D-19F, a connection element 300 is arranged for threaded engagement with threaded bore 295 of winged nut 294. Connection element 300 includes a first generally cylindrical portion 301 having a throughgoing axial bore 302 and a throughgoing bottom slit 303 formed therein. A threaded generally cylindrical collar portion 304 is located at an intermediate location along connection element 300 forwardly of first generally cylindrical portion 301 in the sense of FIG. 19A. A second generally cylindrical portion 305 is located forwardly of collar portion 304 and has a cross sectional diameter which is greater than that of first cylindrical portion and less than that of collar portion 304.

Forward of second generally cylindrical portion 305 there are preferably provided a pair of spaced lugs 306 which are separated by a vertical recess 307. Connection element 300 also includes an aperture 308, formed in generally cylindrical portion 301, in which is seated an axial guiding pin 309.

A latch element 310 includes a forward portion 311, having a top transverse bore 312 through which extends a transverse pin 313 for pivotable attachment of latch element 310 to connection element 300 via lugs 306. Latch element 310 also includes a rearwardly facing latch extension portion 314 which is seated in throughgoing bottom slit 303 and includes a depending latch protrusion 315, at a rearward end thereof, for removable latched engagement with collar member 136 of working channel assembly 124.

Forward portion 311 also includes a bottom transverse bore 316 which accommodates a pin 317, onto which is connected a first end of a tension spring 318, whose opposite end is connected to a pin 319 which is mounted at opposite ends thereof at respective locations 320 in right and left housing elements 102 and 104.

Transverse pin 313 is mounted at opposite ends thereof at respective locations 321 in right and left housing elements 102 and 104.

Forward portion 311 is also formed with an aperture 322 for accommodating working channel assembly 124, which extends therethrough.

Returning now to the description of the working channel assembly 124 in greater detail and referring now additionally to FIGS. 26A-26C, as mentioned above, working channel assembly 124 includes a main longitudinal rigid tube 128 and a hardened forward tube 130. Driving socket element 132 is preferably welded onto a rear end of main tube 128 and is rotatably mounted within collar member 136. Driving socket element 132 is restrained against axial movement relative to collar member 136, preferably by a pair of retaining pins 138, which extend through transverse apertures formed in collar member 136 and engage a groove 140 formed in driving socket element 132.

Turning specifically to FIG. 26C, it is seen that socket element 132 is a generally cylindrical element which has a non-circular driving bore 134, typically of hexagonal cross section, extending partially therethrough from a rear end 323 of socket element 132. A narrow bore 324 extends forwardly of driving bore 134 and extends into a broadened bore 325 which terminates at a forward circumferential recess 326. External circumferential recess 140 surrounds part of broadened bore 325.

Collar member 136 includes a generally cylindrical back portion 327 having a bore 328 which is intersected by pins 138 extending through transverse apertures 329 in cylindrical back portion 327. A narrow bore 330 extends forwardly of bore 328 and communicates with a recess 332. Cylindrical back portion 327 is also formed with an axial bottom groove 334 having side lobes 336 and communicating with a transverse aperture 337.

Forward of back portion 327 is a generally cylindrical forward portion 338 having an axial slot 340 which extends partially into cylindrical back portion 327 as shown at reference numeral 342. Axial guiding pin 309 of connection element 300 engages axial slot 340 to ensure proper rotational alignment of working channel assembly 124 and to ensure proper alignment of suture cartridge assembly 170.

The assembly of socket element 132 inside collar member 136 and the mounting therein of main longitudinal rigid tube 128 is shown in an enlarged sectional portion of FIG. 26A.

Reference is now made specifically to FIGS. 21A-24B, which illustrate bone-engaging needle driving assembly 122. The bone-engaging needle driving assembly 122 includes linear gear rack element 270, which is preferably driven along an elongate travel path responsive to reciprocal motion of ratchet handle 150.

Bone-engaging needle driving assembly 122 includes a static forward portion 400, including a mounting base 402, which extends forwardly of a forward end of the housing, which is fixed to an extension shaft 404 extending axially inwardly thereof and forwardly therefrom. Fixed to extension shaft 404 and extending forwardly thereof, there is preferably formed an arcuate needle storage and guiding portion 406.

Mounting base 402 is generally configured as a hollow cylinder to accommodate part of extension shaft 404 therewithin and is formed with matching side apertures 408 which accommodate mounting pins 410 (FIG. 19B), which serve to mount the mounting base 402 onto housing portions 102 and 104, as seen in FIG. 19B.

Extension shaft 404 is preferably formed of two side by side pieces 411. Side pieces 411 together define two mutually spaced axial mounting bores extending therethrough, which bores are designated by reference numerals 412 and 414. Bore 412 slidably accommodates working channel assembly 124 and has a generally round cross-section.

Bore 414 slidably accommodates parts of a flexible arcuate needle driving assembly, which preferably includes a flexible needle driving strip 418, preferably formed of spring steel, and generally rigid flexible needle driving strip driving shaft 280, which is mounted at the rear of flexible needle driving strip 418, preferably as shown in enlargements A & B in FIG. 21A. This mounting is preferably by means of engagement of a protrusion 419 formed adjacent the forward end of rigid flexible needle driving strip driving shaft 280 with a corresponding aperture 420 formed adjacent a rearward end of flexible needle driving strip 418.

As seen in enlargement A of FIG. 21A, bore 414 has a generally circular cross sectional central portion 422 to accommodate shaft 280, from which portion extend a pair of symmetrical side cut outs 424 to accommodate the side edges of strip 418.

As seen particularly in enlargement D of FIG. 21A, forward of extension shaft 404, there is preferably formed an arcuate needle storage and guiding portion 450, which is formed with an arcuate bore 452 including a portion 454 having a generally rectangular cross section, which slidably accommodates needle 162. A pair of symmetrical side cut outs 456 extend outwardly from portion 454 and accommodate the side edges of flexible needle driving strip 418.

It is also seen in an enlargement of FIG. 22A, that the forward end of flexible needle driving strip 418 is attached to arcuate needle 162. This attachment is preferably by means of engagement of a protrusion 466 formed adjacent the rearward end of arcuate needle 162 with a corresponding aperture 467 formed adjacent a forward end of flexible needle driving strip 418.

Reference is now made to FIGS. 27A, 27B, 27C, 27D, 27E, 27F, 27G, 27H, 27I, 27J, 27K, 27L, 27M, 27N, 27O, 27P, 27Q and 27R, which illustrate details of the operation of the arthroscopic surgical device of FIGS. 1A-26C, and to FIGS. 28A, 28B, 28C, 28D, 28E, 28F, 28G, 28H, 28I, 28J, 28K, 28L, 28M, 28N, 28O, 28P, 28Q, 28R, 28S, 28T, 28U, 28V, 28W and 28X, which are simplified illustrations of operation of the arthroscopic surgical device of FIGS. 1A-27R in a clinical context.

Figure 27A:
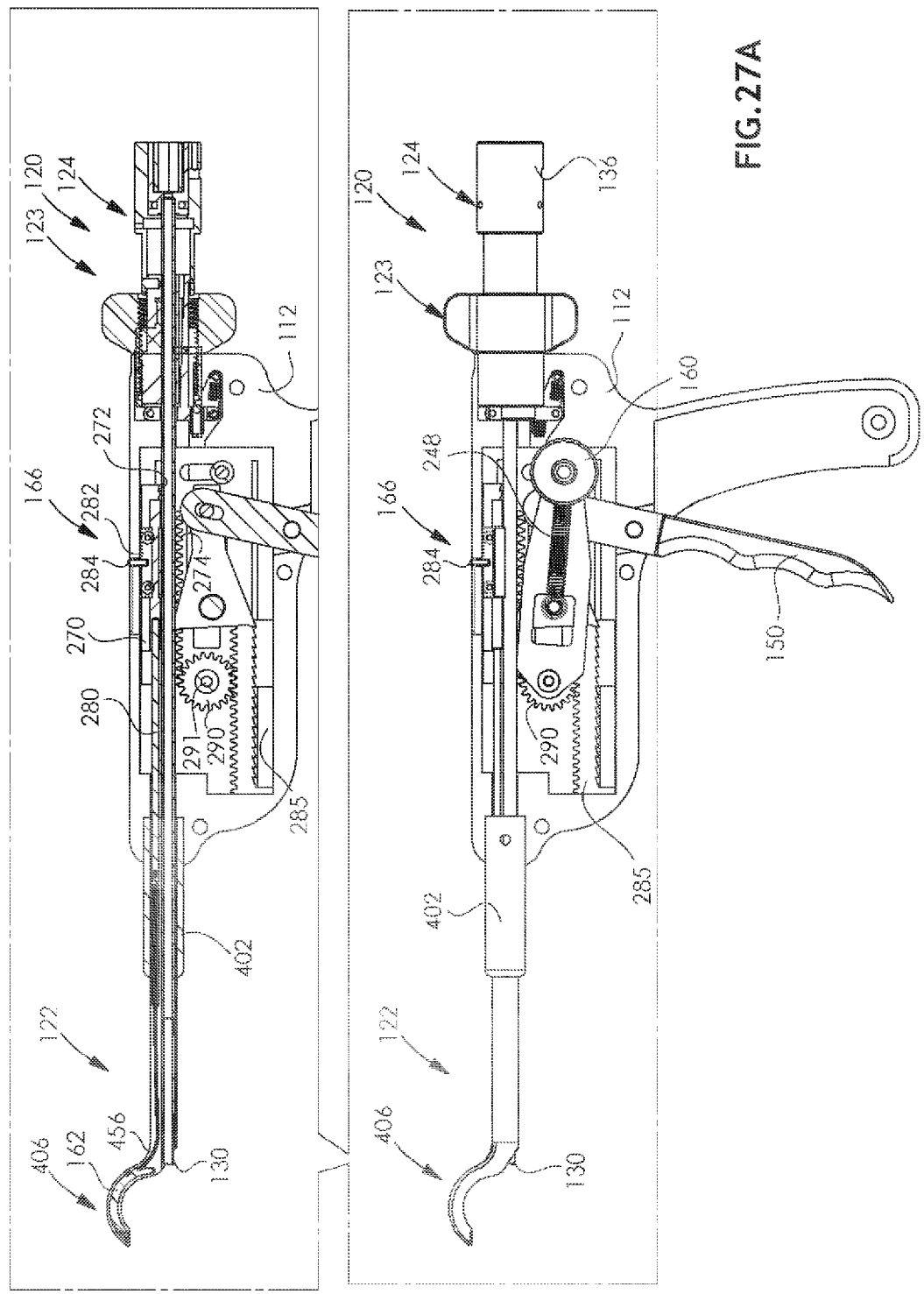
Figure 28B:
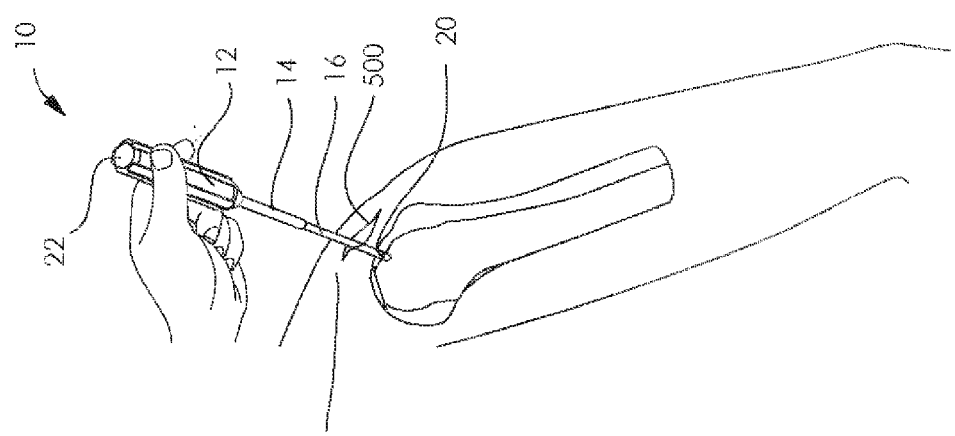
Figure 28A:
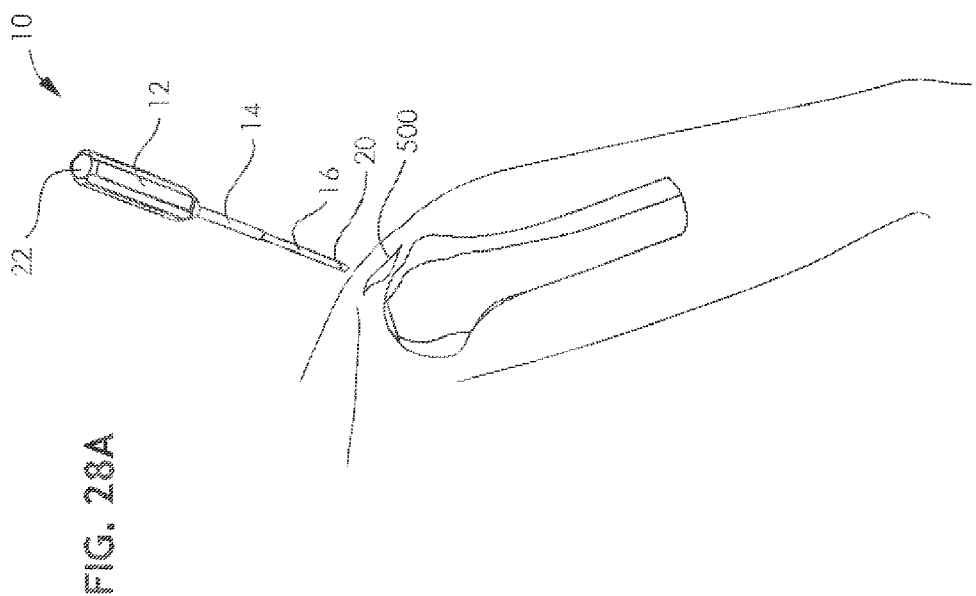
Figure 28C:
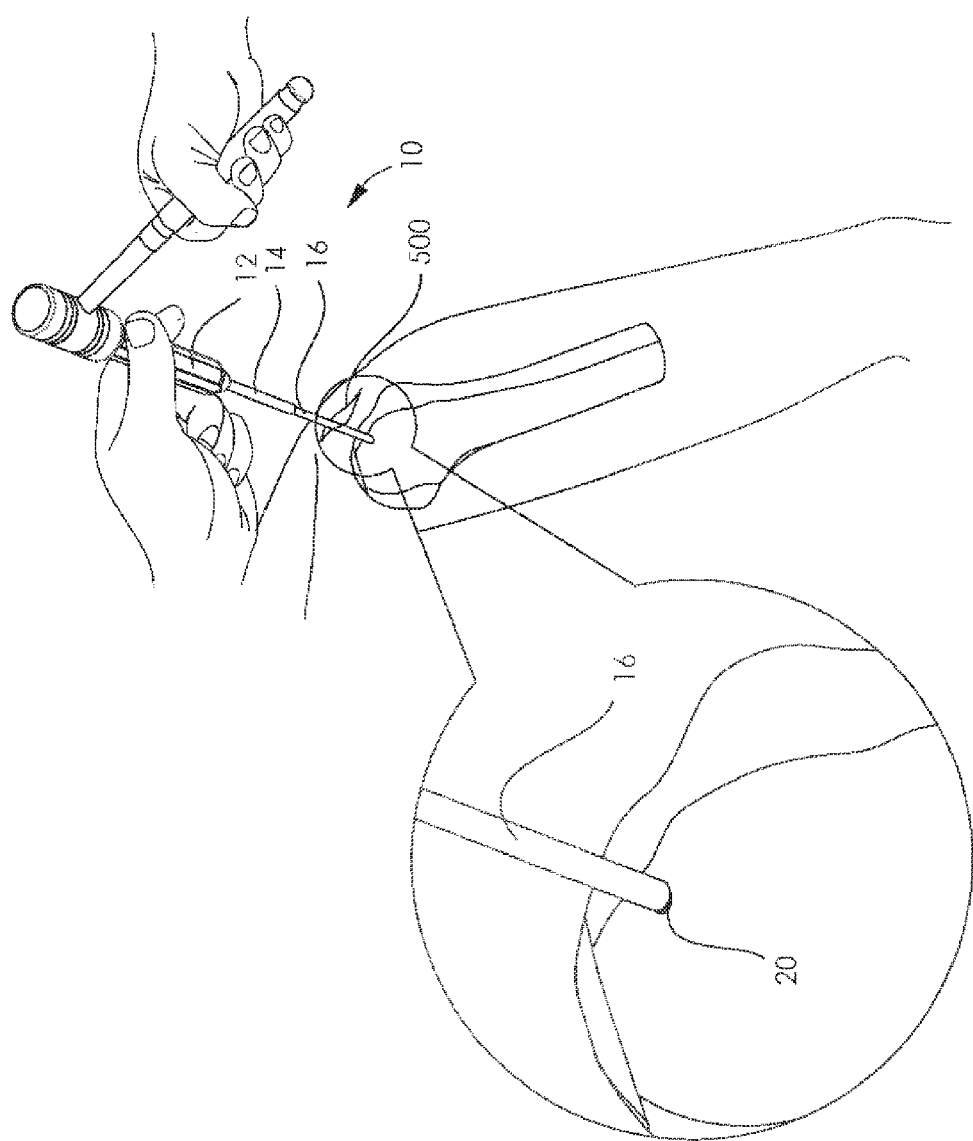
Figure 28D:
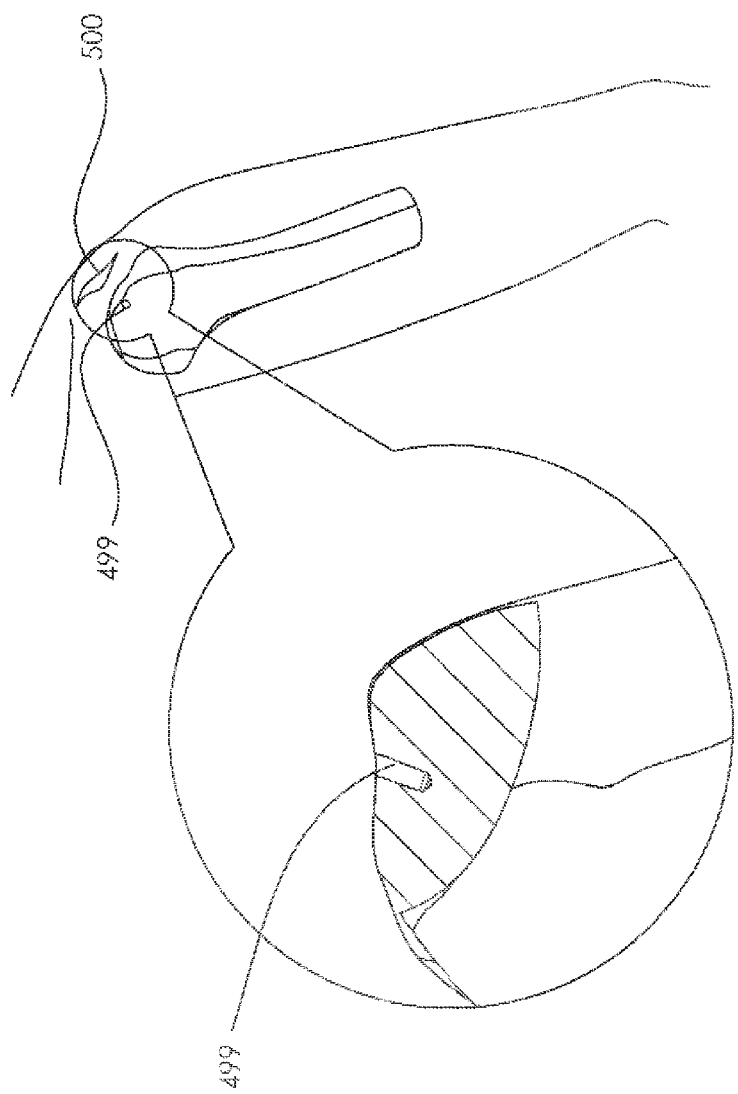
Figure 28E:
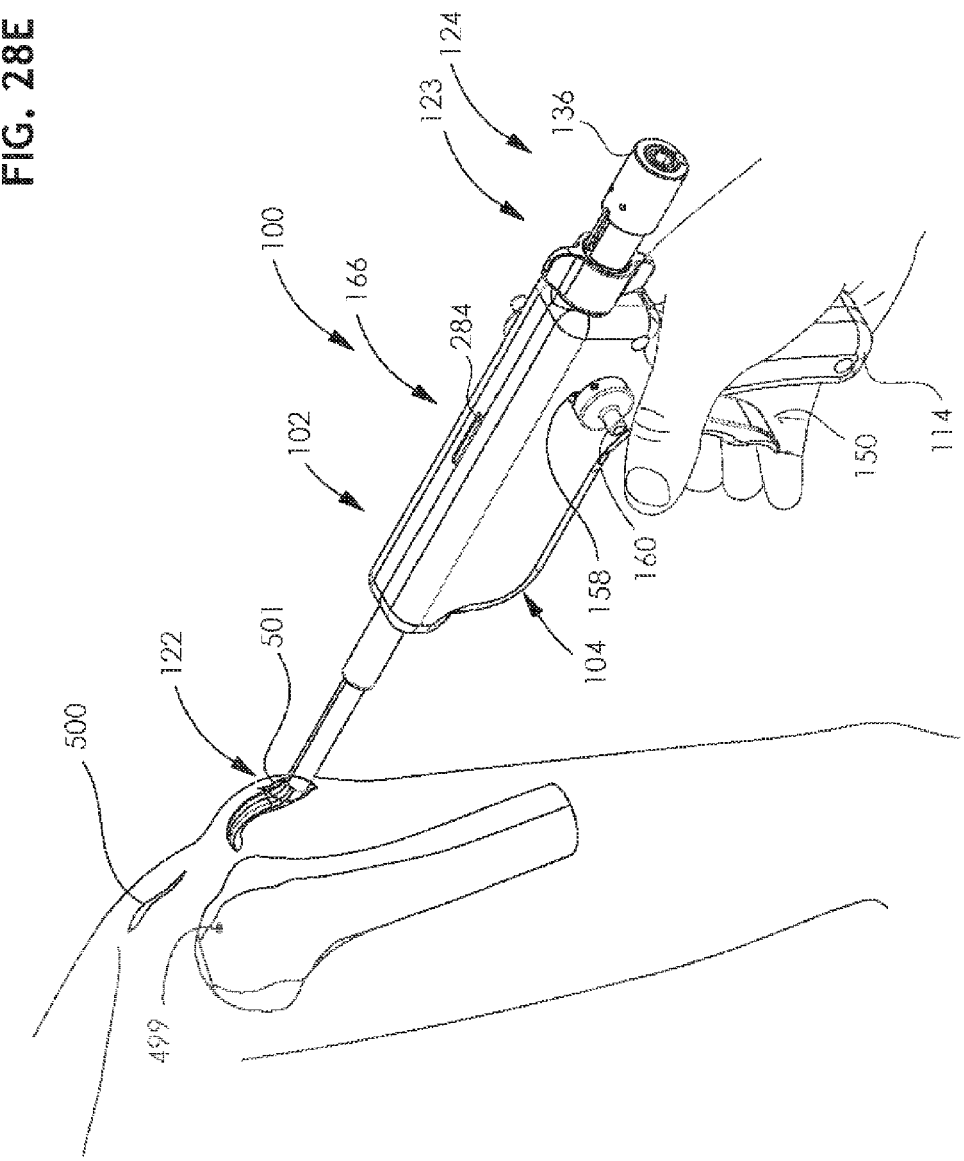

Reference is initially made to FIGS. 28A-28D, which show an initial step of using punch 10 (FIG. 1B) to form a channel 499 in a bone, such as a humerus. A surgeon positions punch 10 opposite an appropriate arthroscopic incision 500 in a patient, as shown in FIGS. 28A and 28B. As seen in FIG. 28C, using a surgical hammer which impacts on impact surface 22 of punch 10, the surgeon forces the forward portion 16 of the punch 10 into the humerus up to line 20. The punch is then withdrawn from the patient, leaving channel 499 in the humerus, as shown in FIG. 28D. FIG. 28E illustrates initial insertion of the arthroscopic surgical device of FIGS. 2A & 2B, in a first operative orientation, as shown in FIG. 27A, through an arthroscopic incision 501 adjacent to incision 500.

Figure 27B:
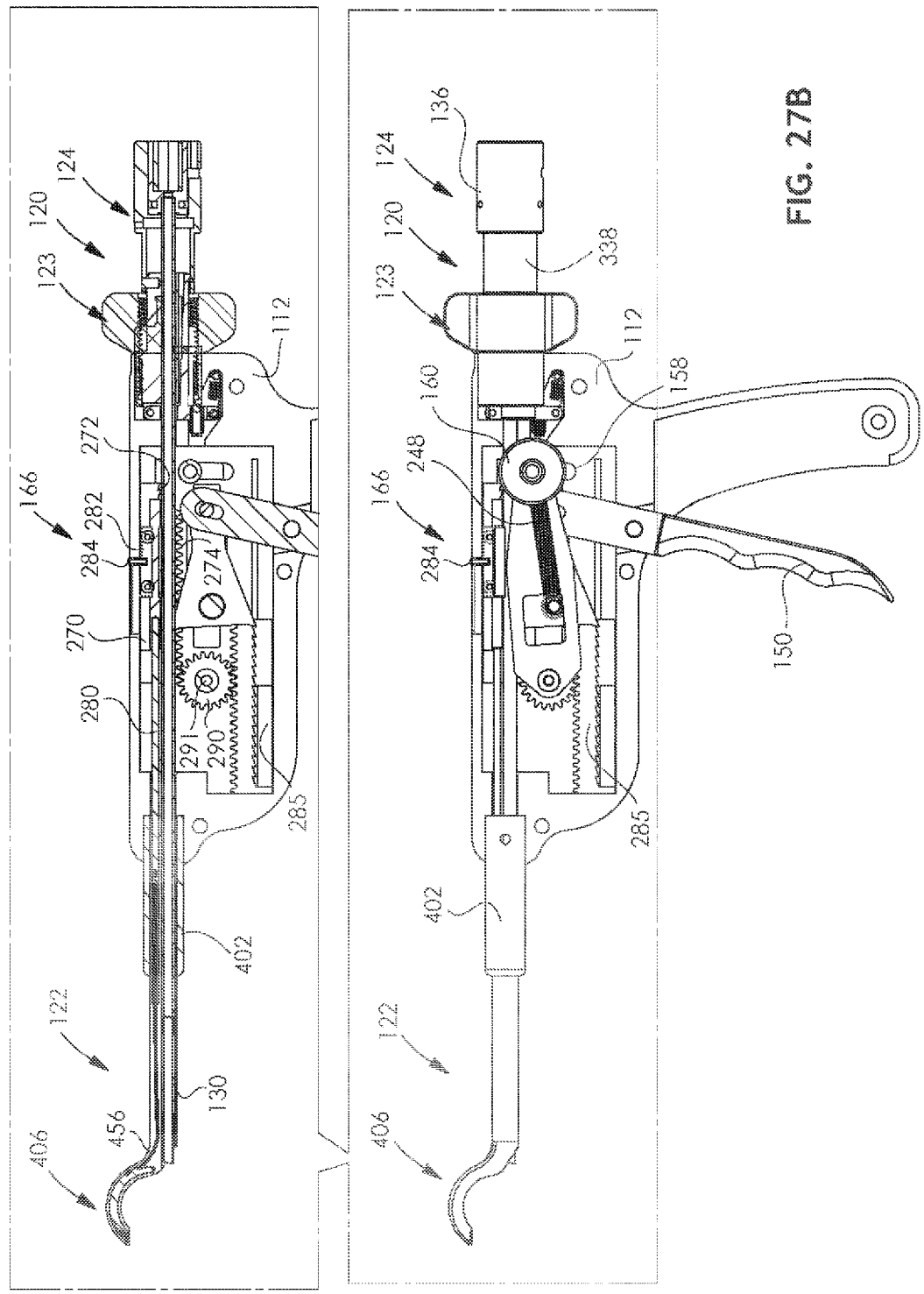
Figure 28F:
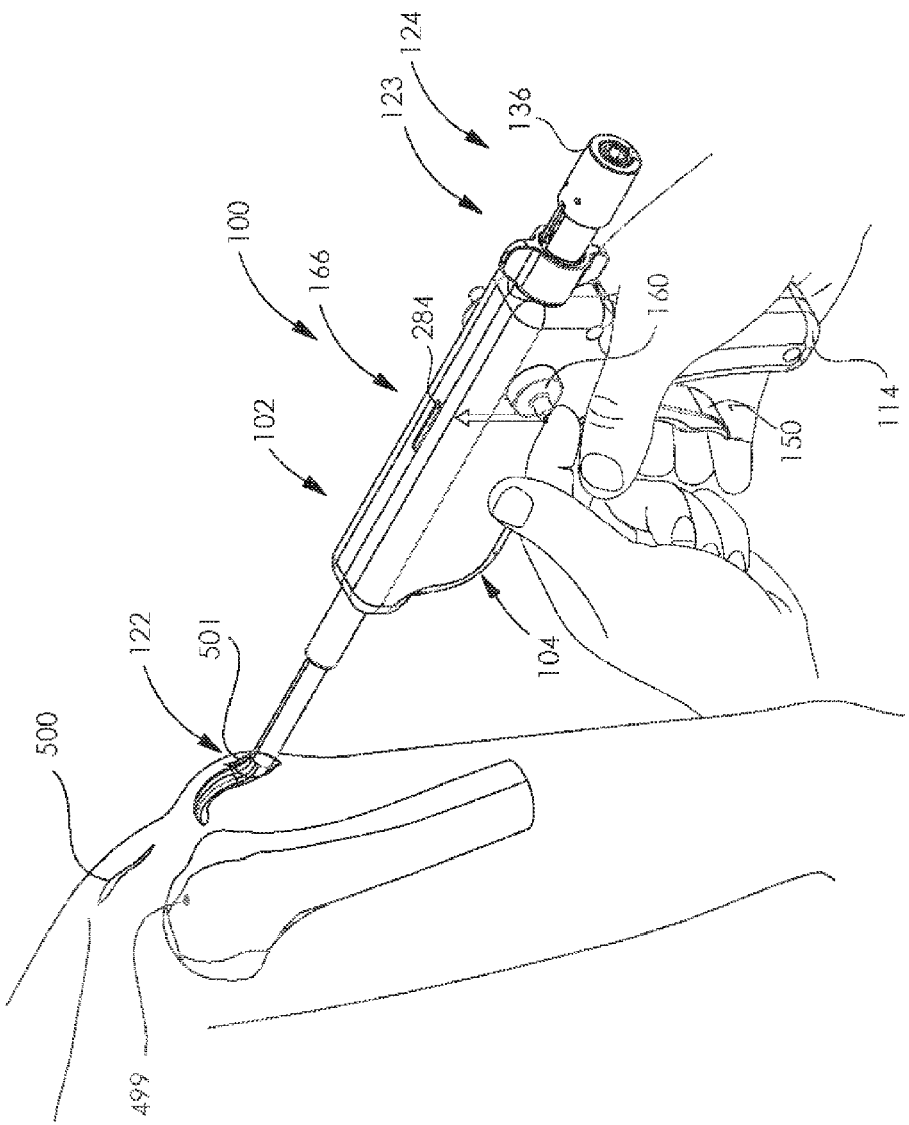

Reference is now made to FIGS. 27B and 28F which illustrate shifting of knobs 160 in slots 158 to their upward positions.

Figure 28G:
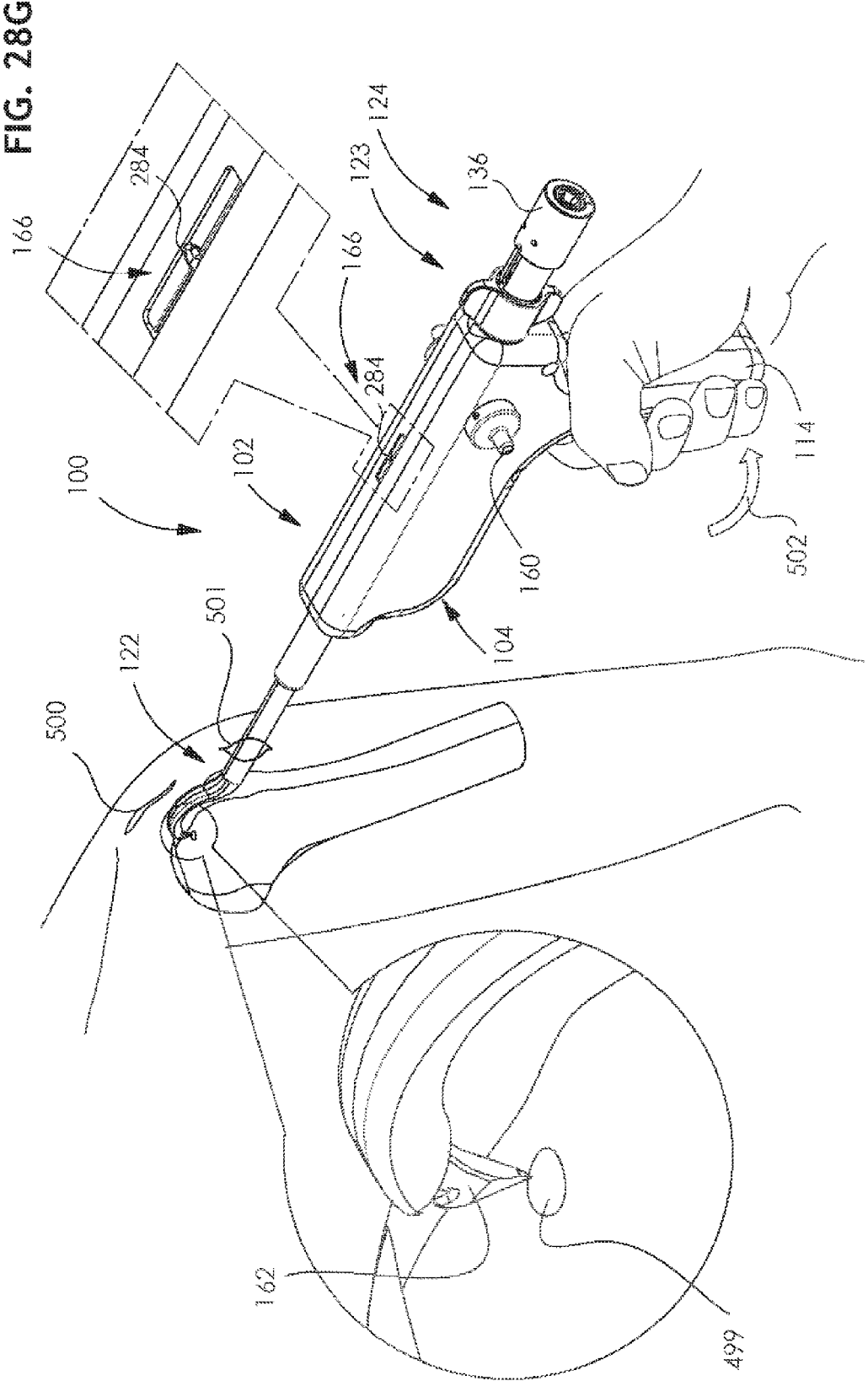
Figure 28H:
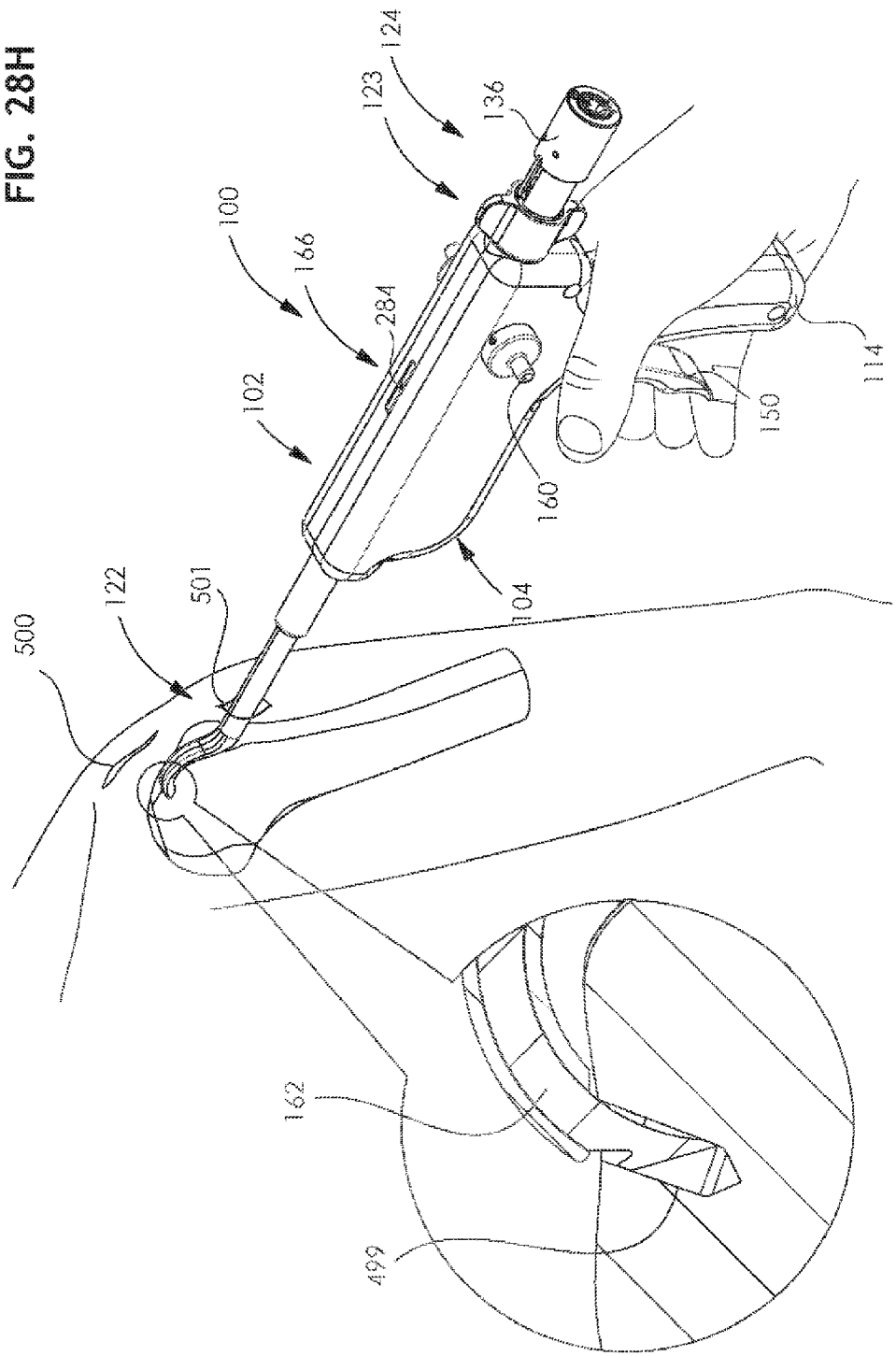

Reference is now made to FIG. 27C and FIG. 28G, which correspond to FIGS. 4A & 4B and show extending of the needle 162, by squeezing of handle 150 as indicated by an arrow 502 and positioning of the extended forward portion of needle 162 in channel 499 in the humerus. FIG. 28H shows the forward portion of needle 162 fully inserted in channel 499.

As seen in FIG. 28C, needle 162 preferably has a radius of curvature which is generally equal to or greater than a length of channel 499. Additionally, it is appreciated that the geometry of needle 162, including its width and inner and outer radii of curvature, and the geometry of channel 499, including its length and width, are such that needle 162 can pass through channel 499 without changing the configuration of channel 499 to add curvature thereto.

Figure 27D:
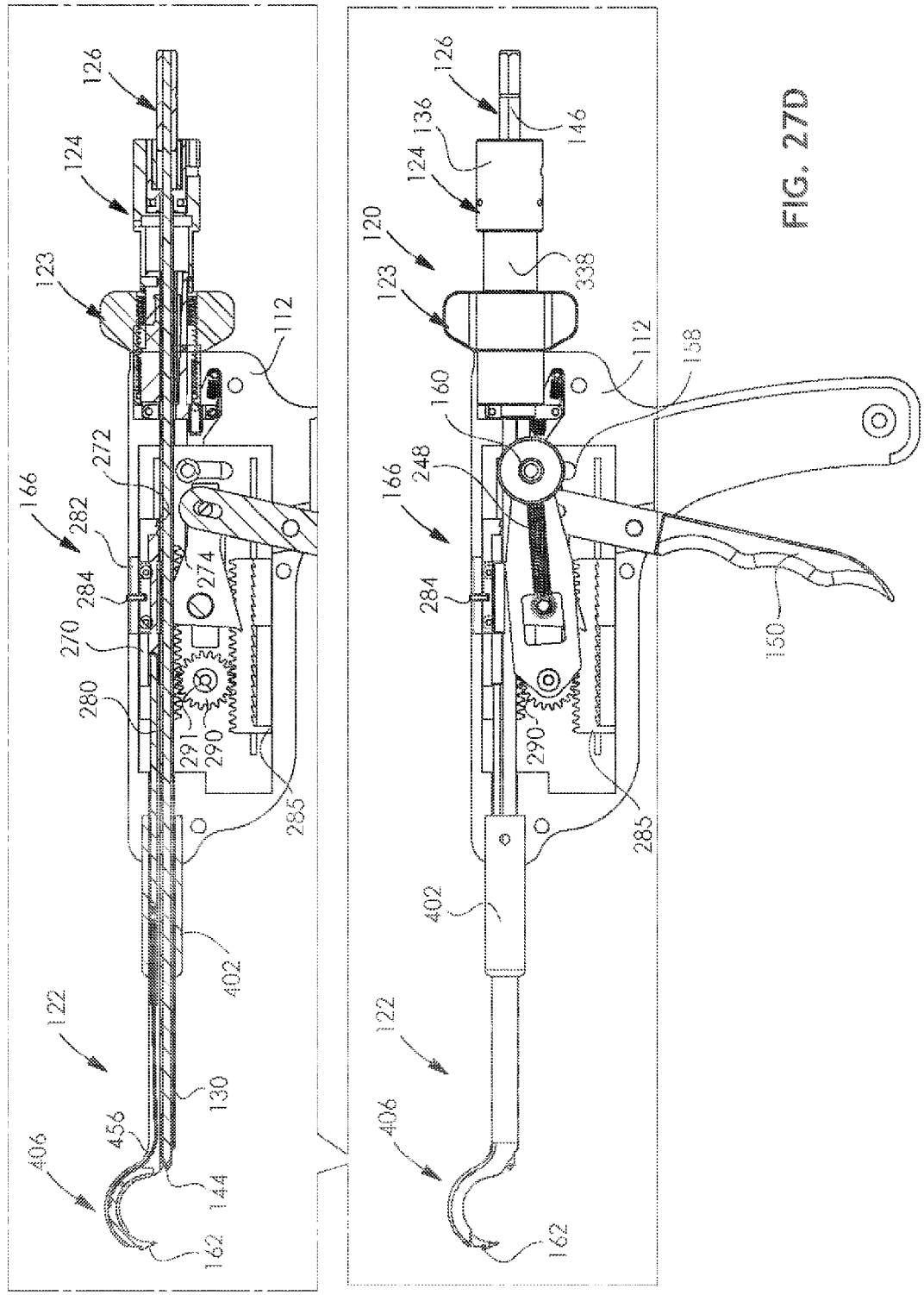

Reference is now made to FIGS. 27D and 28I, which show drill 126, such as that described hereinabove with reference to FIGS. 20A & 20B, being mounted onto the arthroscopic surgical device 100 and being initially positioned, as indicated by an arrow 503, to a position wherein the tip 144 touches the outside surface of the humerus.

Figure 27E:
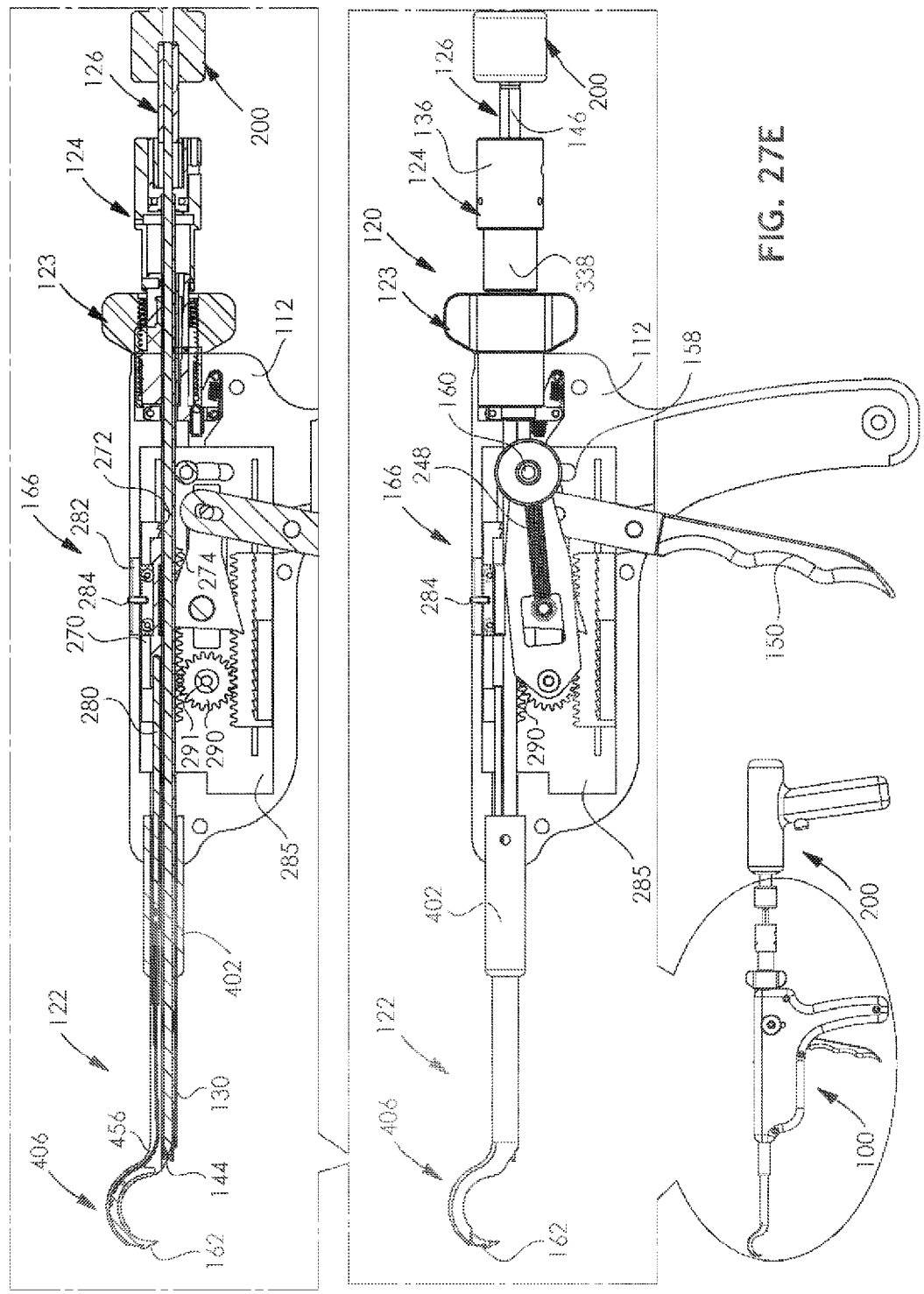

FIGS. 27E and 28J, which correspond generally to FIGS. 6A & 6B, show attachment of surgical drill 200 to widened rear end 146 of drill 126.

Figure 28K:
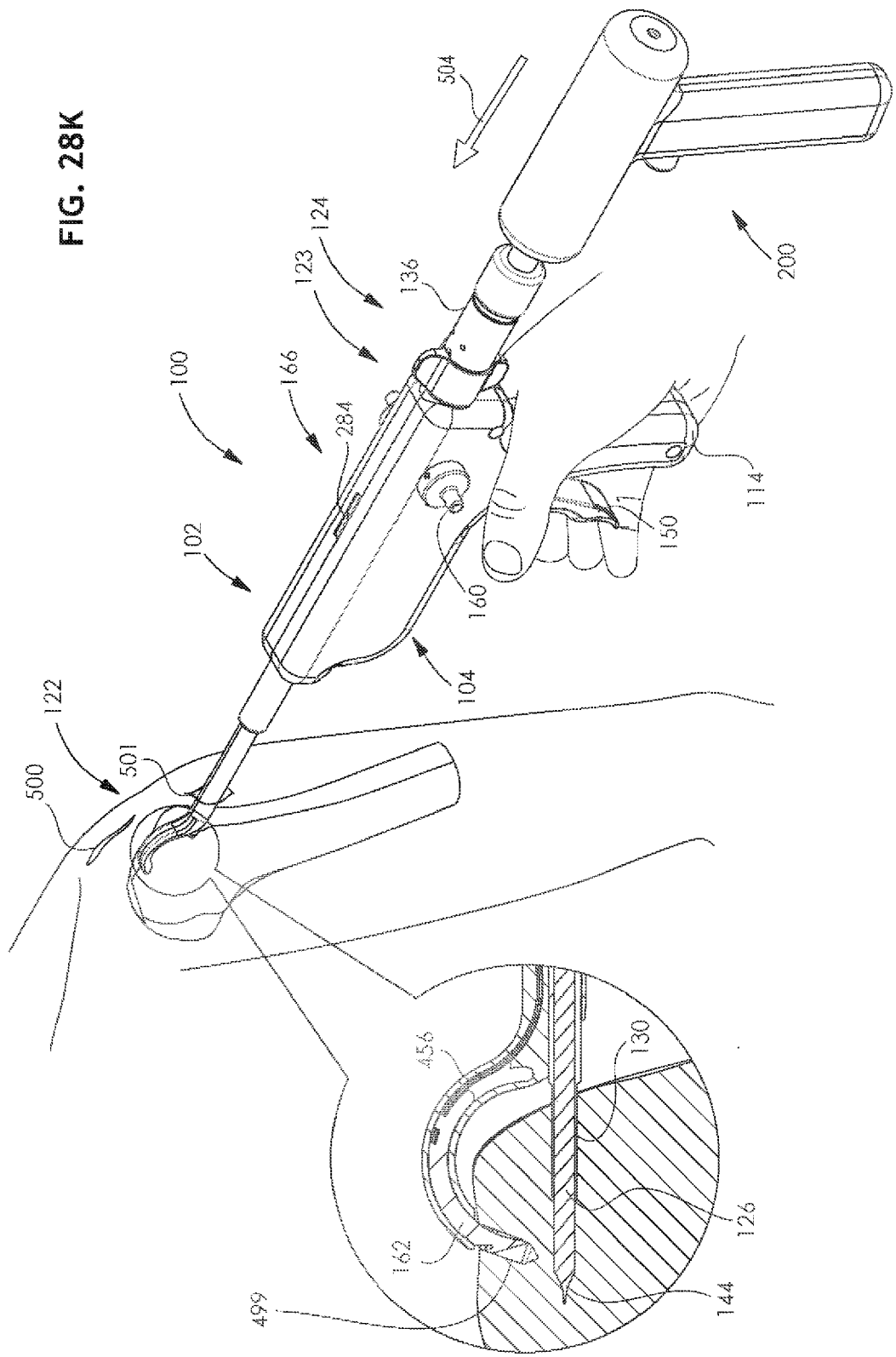

FIGS. 27F and 28K, which correspond generally to FIGS. 7A & 7B, show linear forward displacement of drill 126 and working channel assembly 124 of bone-engaging pin insertion assembly 120 in the arthroscopic surgical device 100, as indicated by an arrow 504. This displacement is preferably achieved by operation of the surgical drill 200 in operative engagement with widened rear end 146 of drill 126. As seen in FIG. 28K, the tip 144 of drill 126 is in its most forward position and tube 130 is in its most forward position.

Figure 27G:
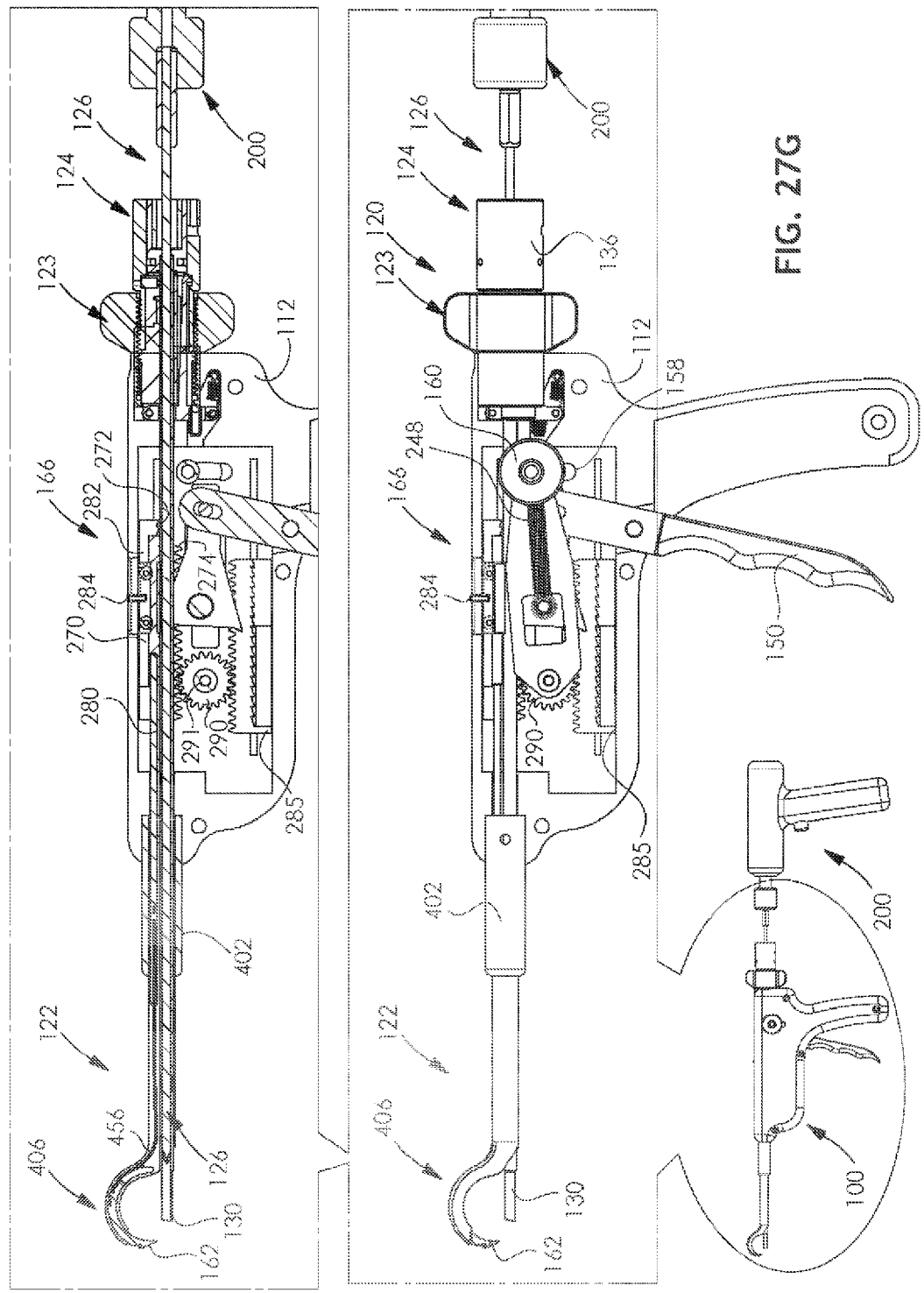

FIGS. 27G and 28L, which correspond generally to FIGS. 8A & 8B, show retraction of the drill 126, as indicated by an arrow 505, while leaving the tube 130 in its most forward position.

As seen in FIG. 28L, a channel formed in the humerus by drill 126 is preferably longer, and more preferably, substantially longer, than channel 499 formed in the humerus by punch 10. It is also seen in FIG. 28L that the channel formed in the humerus by drill 126 does not intersect channel 499.

Additionally, it is appreciated that the channel formed in the humerus by drill 126 and channel 499 formed in the humerus by punch 10 are not parallel channels. Preferably, an angle formed between the channel formed in the humerus by drill 126 and an extension of channel 499 formed in the humerus by punch 10 is generally a right angle or an acute angle greater than 45°.

Figure 27H:
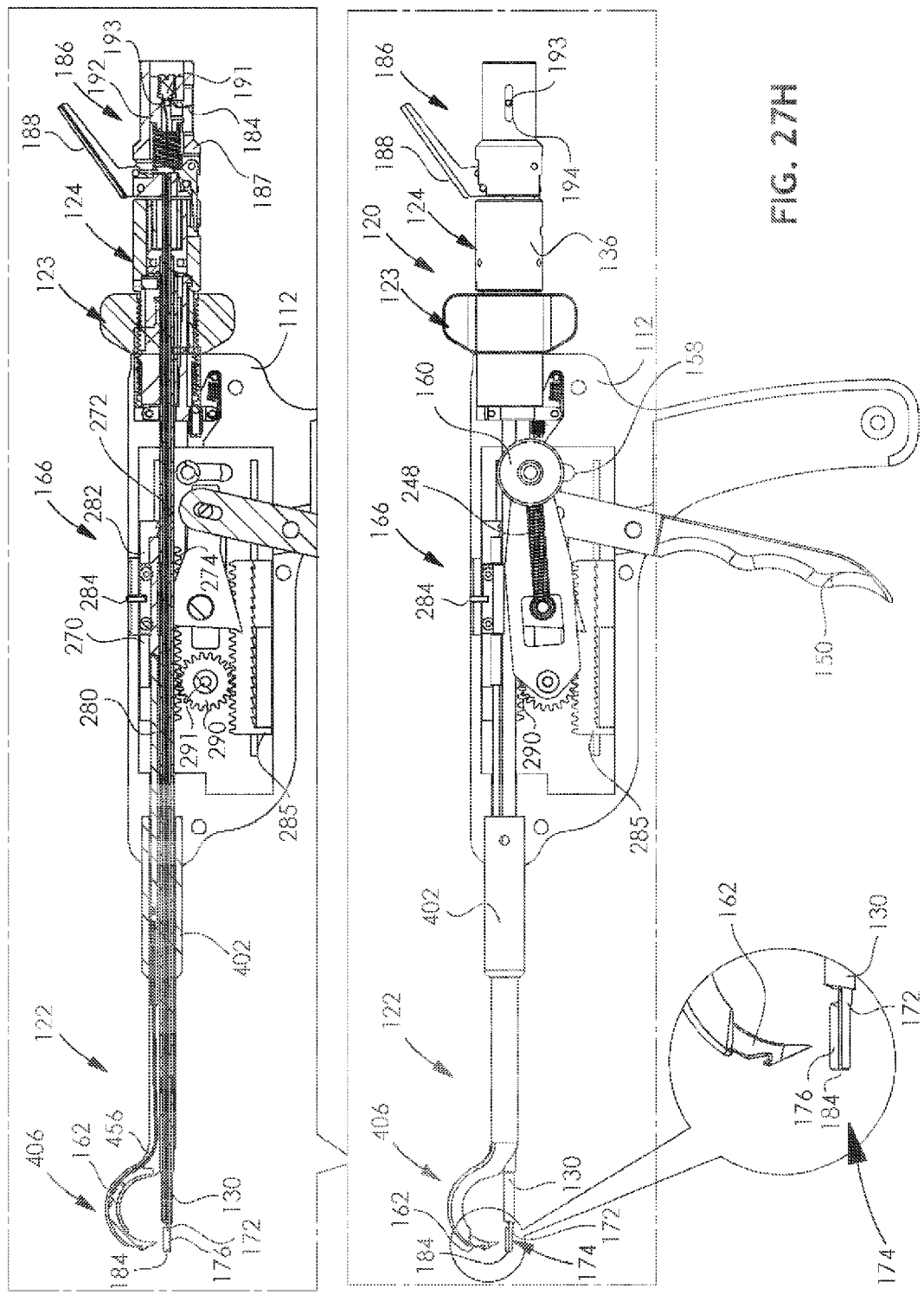
Figure 271:
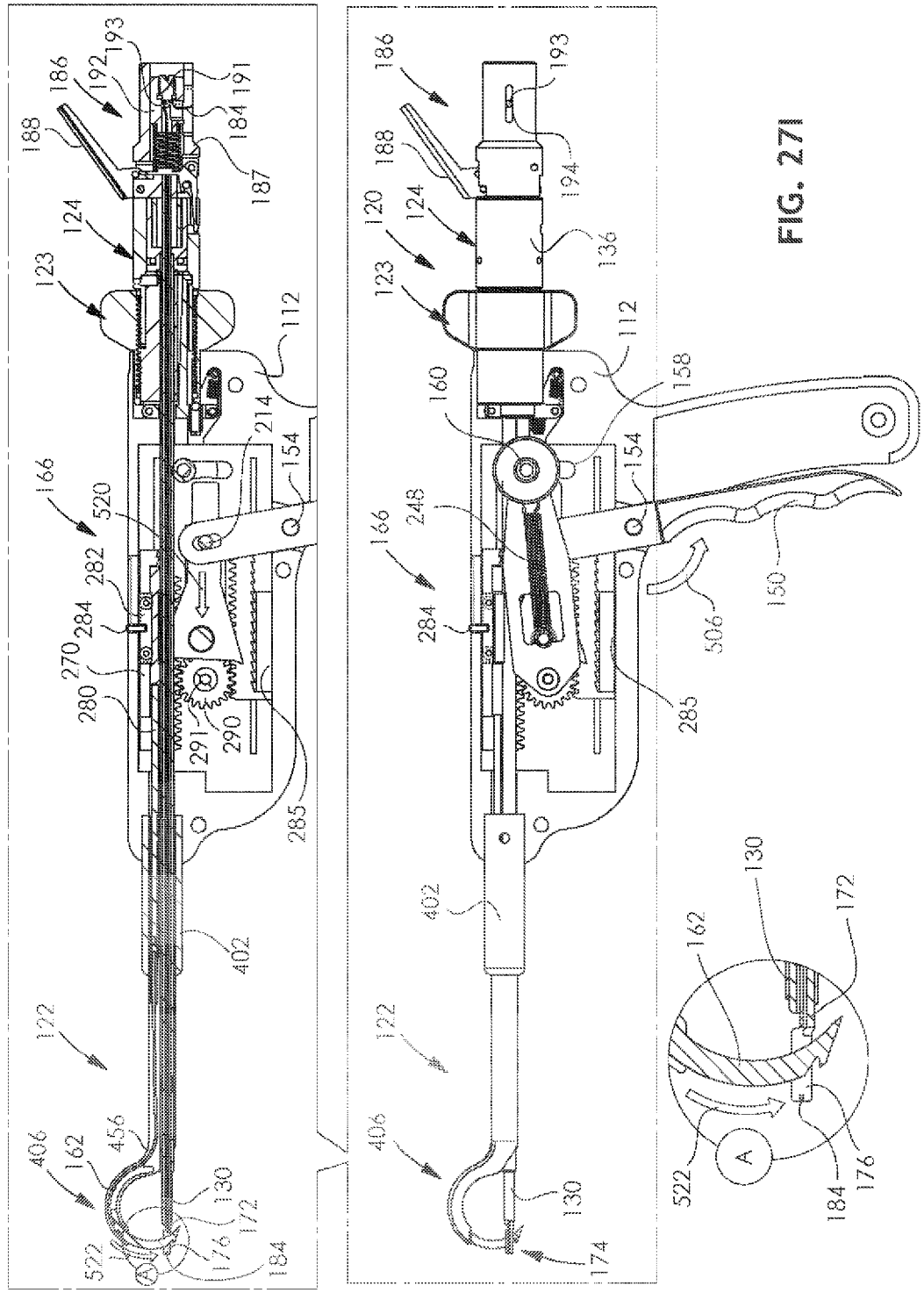
Figure 28M:
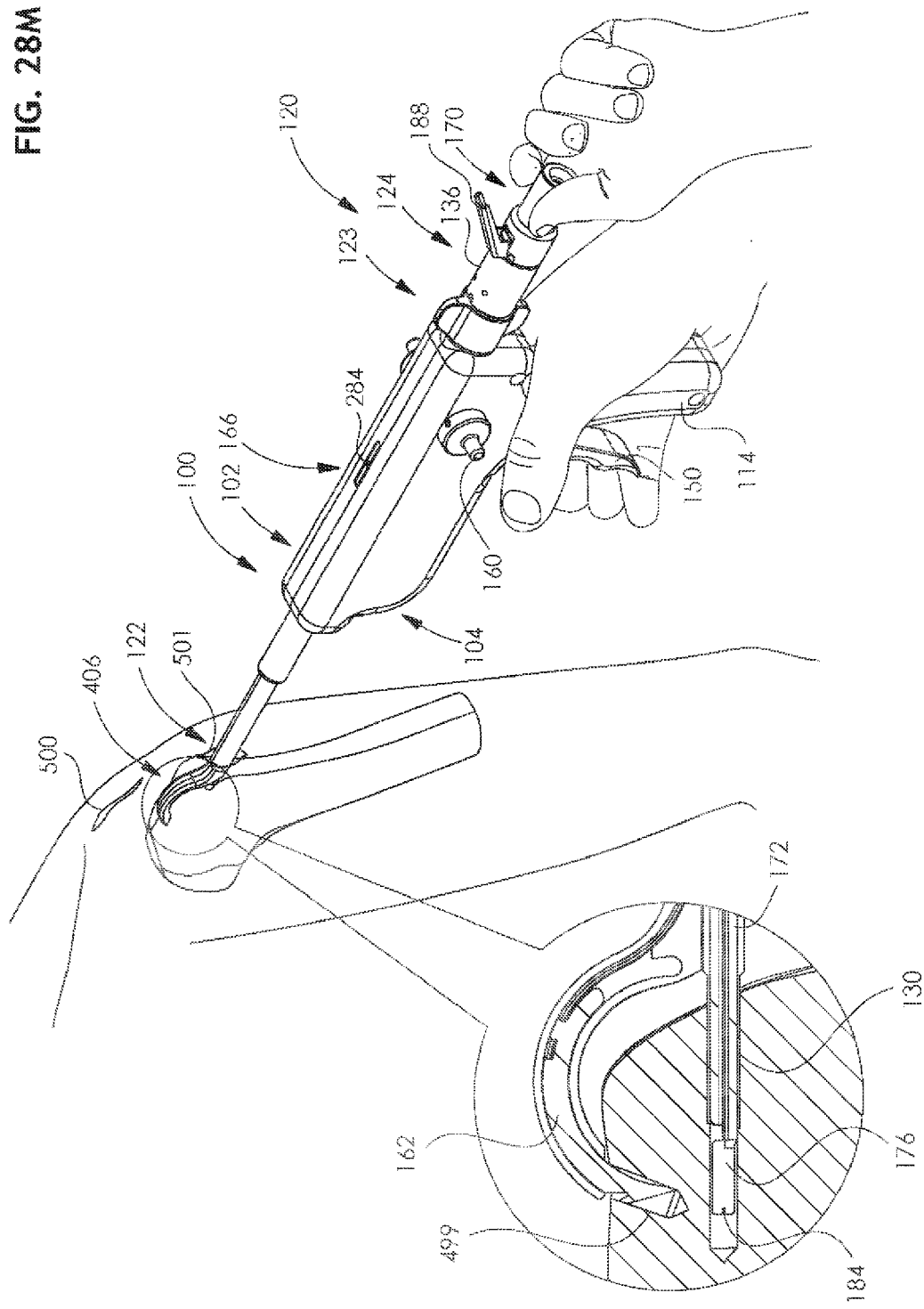
Figure 280:
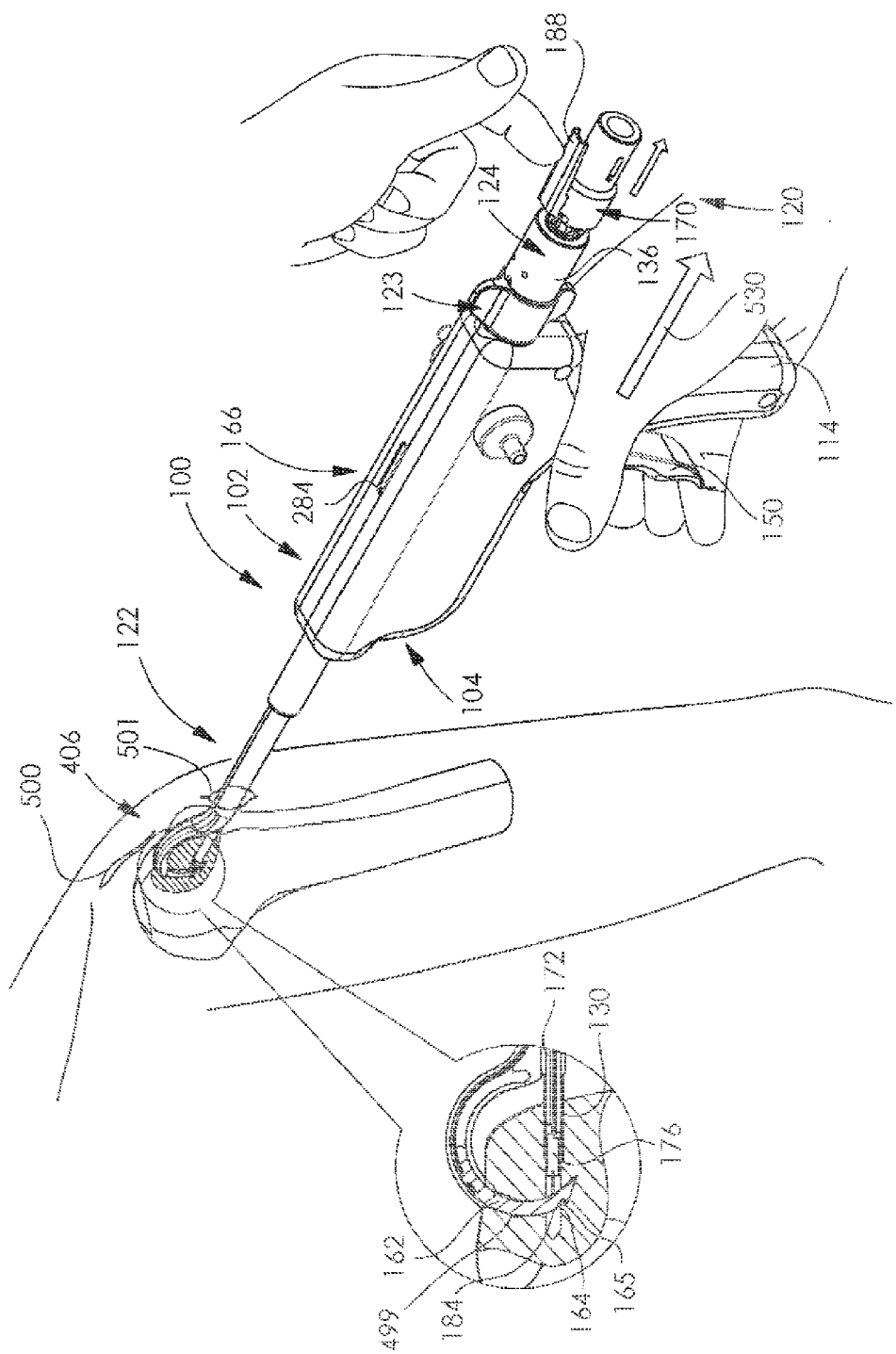

Reference is now made to FIGS. 27H and 28M, which correspond generally to FIGS. 9A and 9B and which show insertion of the suture cartridge assembly 170, including suture 184, in engagement with the working channel assembly 124, such that arms 176 of suture cartridge assembly 170 extend forwardly of a forward edge of tube 130.

Reference is now made to FIGS. 27I and 28N, which correspond generally to FIGS. 10A & 10B and show full extension of arcuate tunneling needle 162 through the bone, as indicated by indicator finger 284 of indicator 166. This full extension is produced by squeezing of handle 150, as indicated by an arrow 506. It is seen that this squeezing of hand-engageable ratchet handle 150 produces rotation thereof, as indicated by arrow 506, about a rotational axis defined by shaft 154 and, via pin 214, displaces first reciprocal motion connection element 220 linearly forwardly, as indicated by an arrow 520, with pointed corner 275 of connection element 220 in engagement with upper linear toothed rack 272 of double rack linear toothed element 270, thereby driving element 270 and needle driving strip driving shaft 280 forwardly and causing arcuate needle 162, driven thereby, to travel along an arcuate path through the portion 454 of arcuate bore 452 having a rectangular cross section and to extend outwardly into tunneling engagement with the bone, as indicated by an arrow 522.

As seen in FIG. 28N, movement of needle 162 forms a curved junction between channel 499 and the channel formed by drill 126.

It is seen that suture engagement groove 164 of arcuate needle 162, which is partially defined by end portion 165, extends between arms 176 rearward of a forward end of suture 184.

Figure 27J:
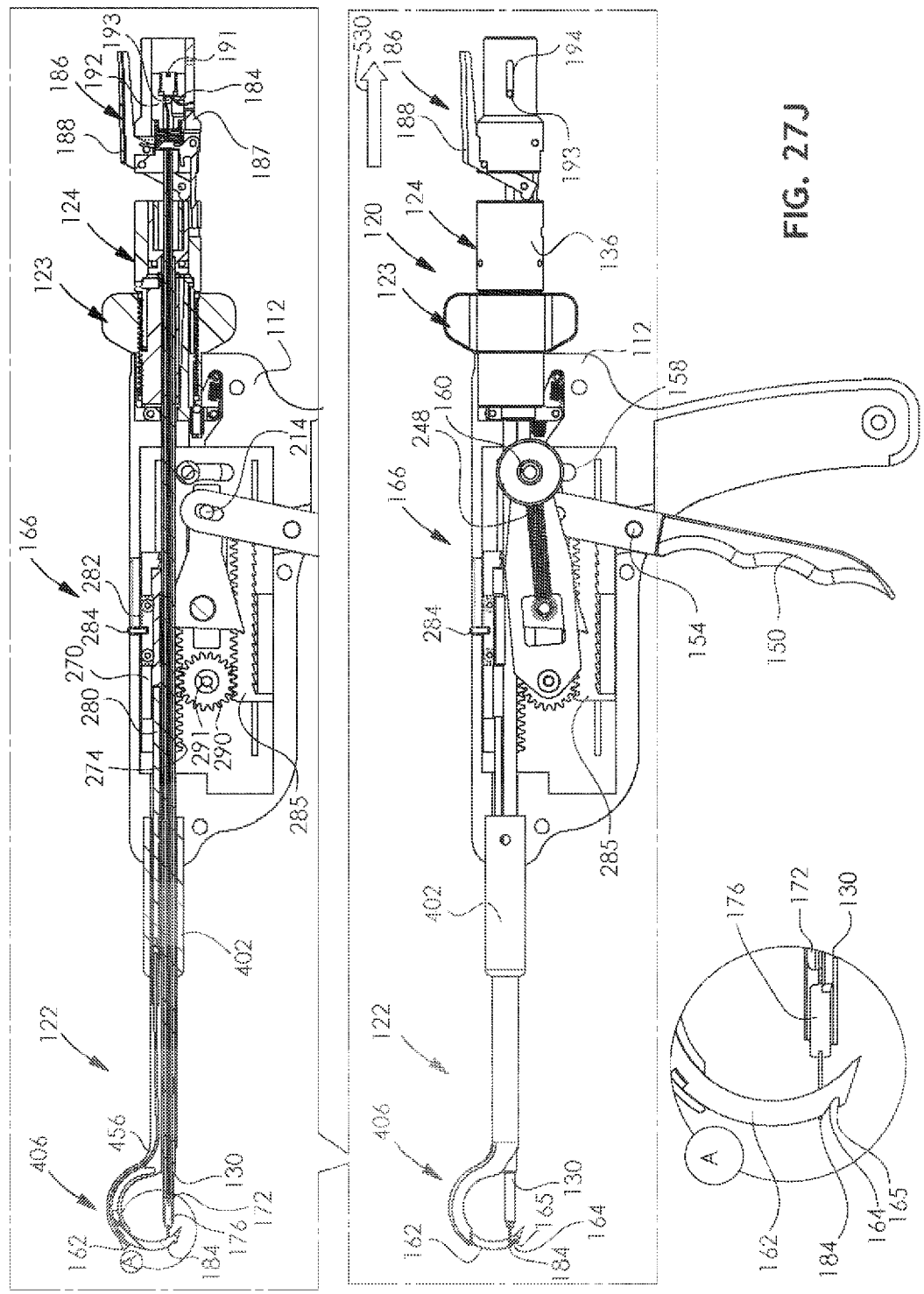

Reference is now made to FIGS. 27J and 28O, which correspond generally to FIGS. 11A & 11B and show partial retraction of the suture cartridge assembly 170 relative to the working channel assembly 124, as indicated by an arrow 530, in response to manual depression of a user-operable suture release lever 188. This retraction causes the forward folded over end of suture 184 to press rearwardly against needle 162.

Figure 27K:
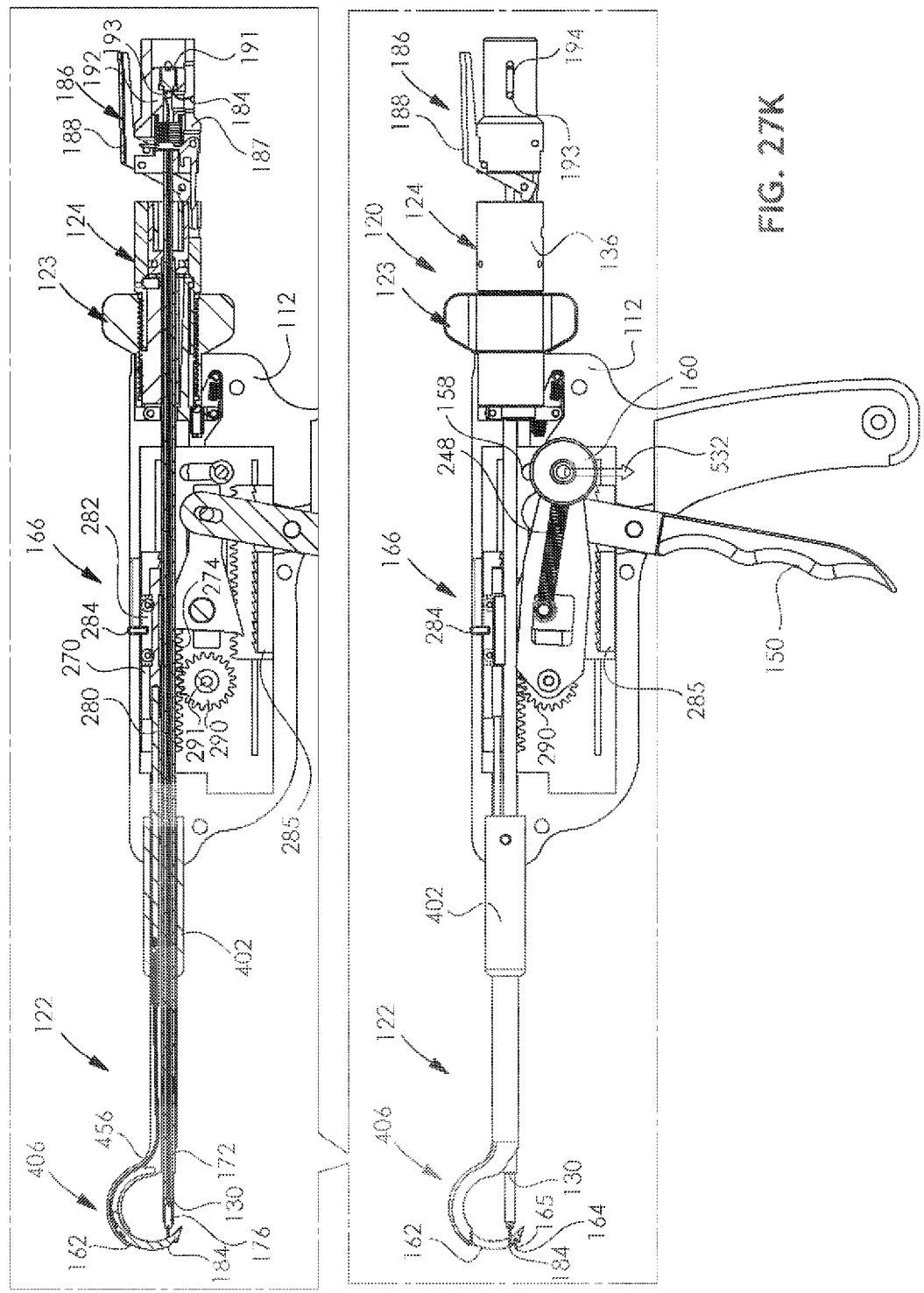
Figure 28P:
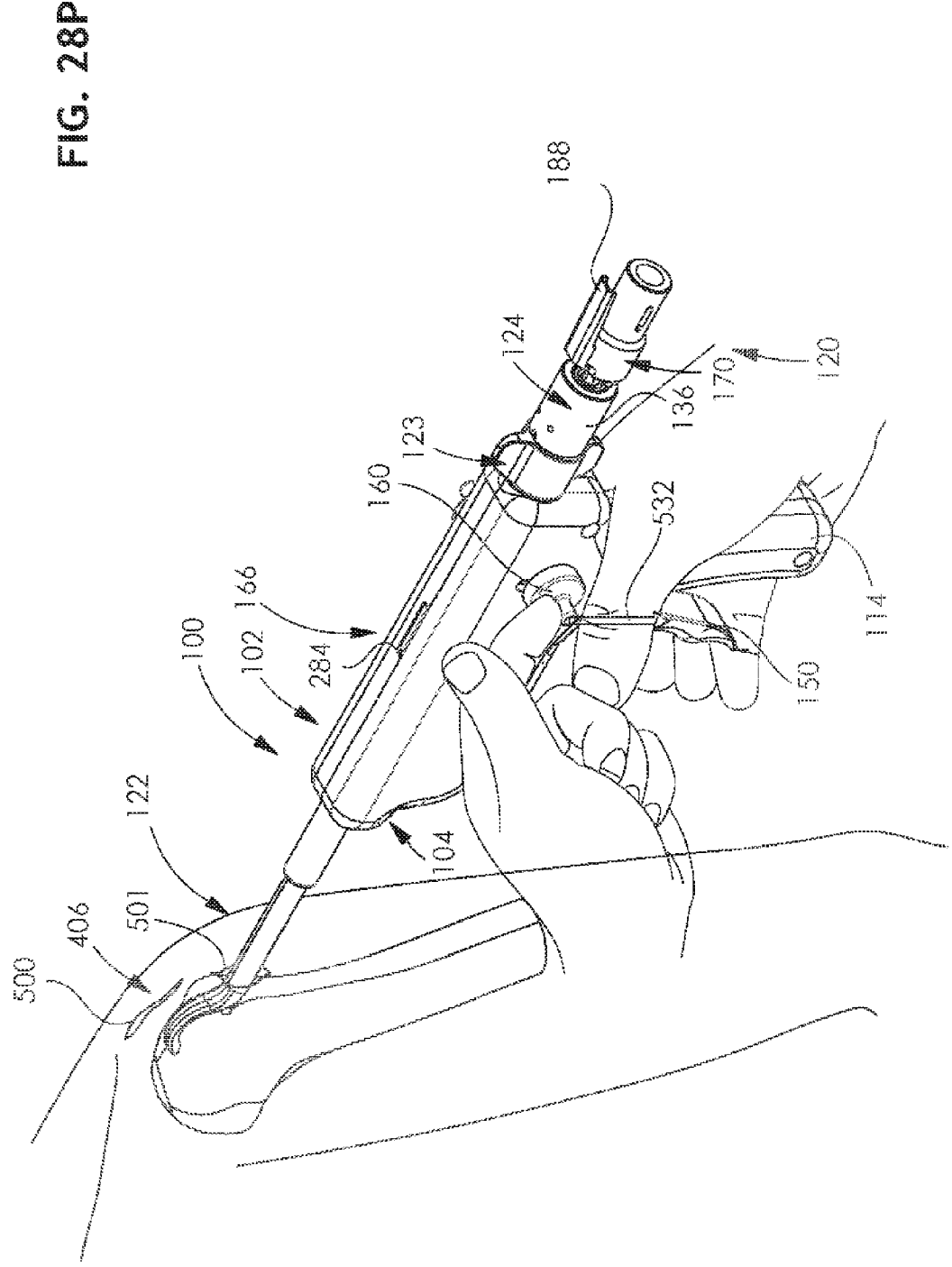

FIGS. 27K and 28P, which correspond generally to FIGS. 12A & 12B, show downward repositioning of knob 160, as indicated by an arrow 532.

FIGS. 27L and 28Q, which correspond generally to FIGS. 13A & 13B, show arcuate retraction of arcuate tunneling needle 162, as indicated by an arrow 534, through the bone, driven by further squeezing of handle 150 as indicated by an arrow 535. The forward folded over end of suture 184 is seen to be in engagement with groove 164 of needle 162, and to be retained therein by end portion 165 of needle 162, such that retraction of the needle 162 pulls the suture 184 together with it along the arcuate travel path of the needle 162.

Figure 27M:
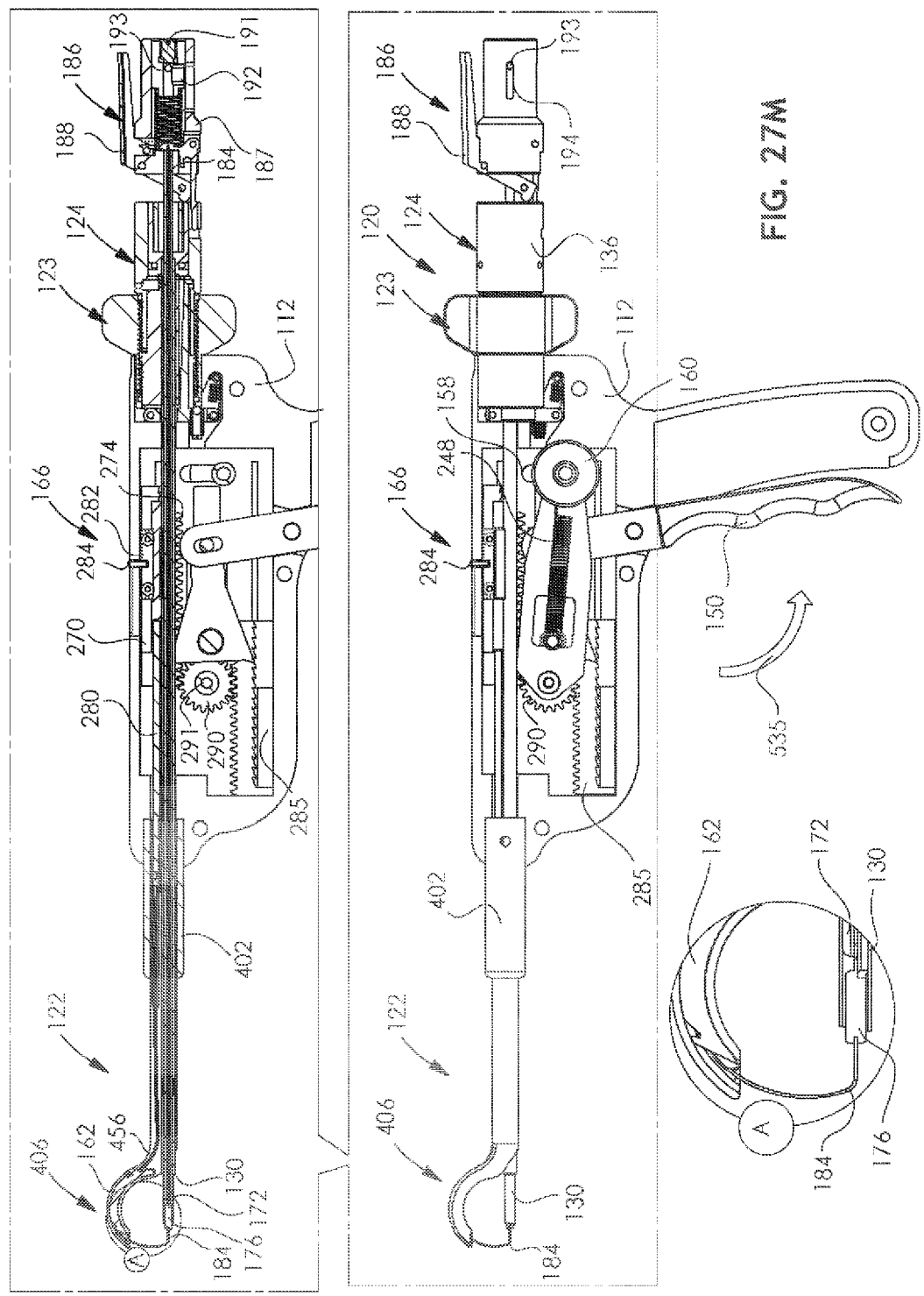
Figure 28R:
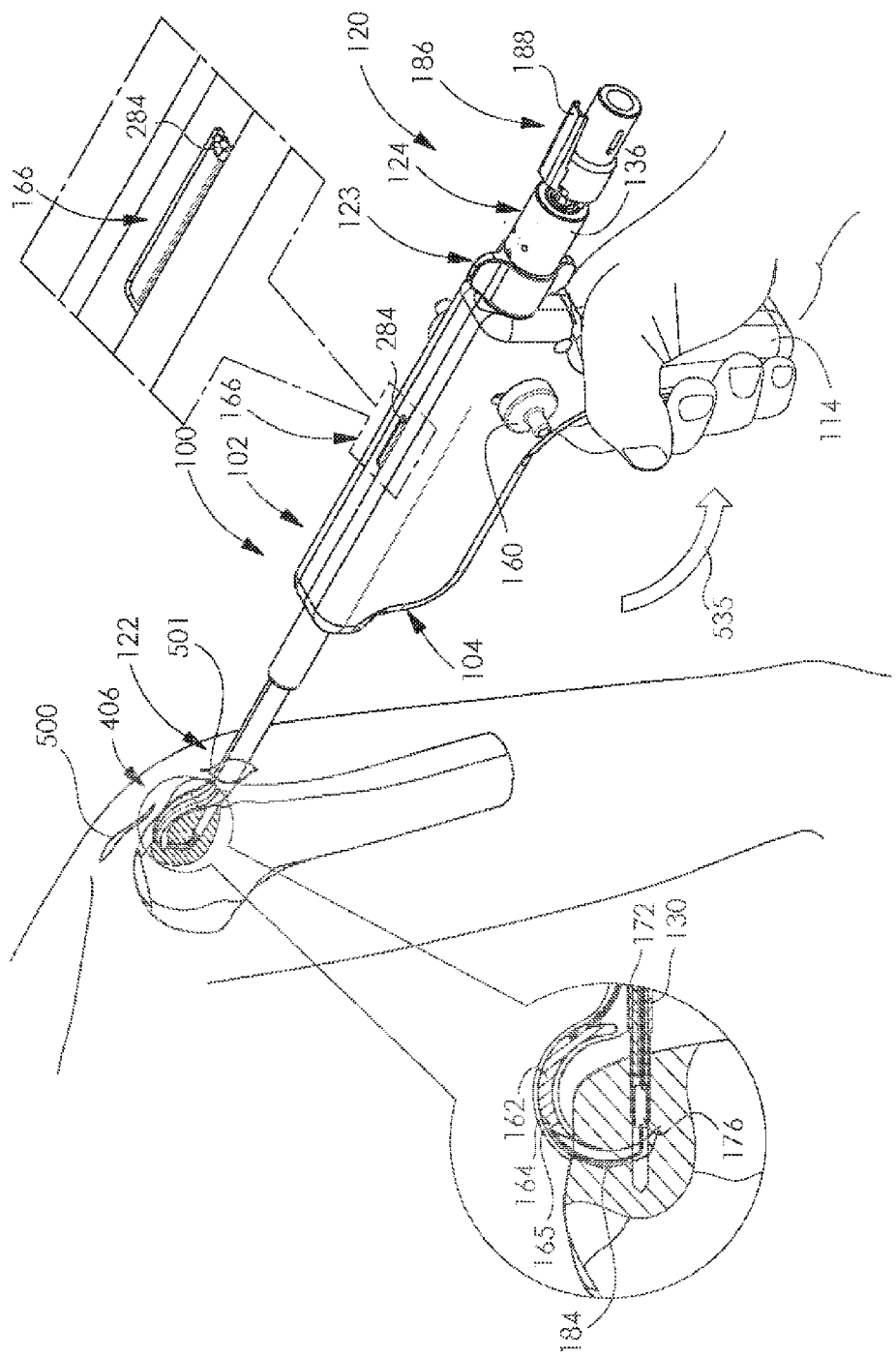

FIGS. 27M & 28R, which correspond generally to FIGS. 14A & 14B, show full retraction of arcuate tunneling needle 162 in engagement with suture 184, thereby pulling suture 184 through the arcuate passageway being traversed by arcuate needle 162. This retraction is provided by further squeezing of handle 150, as indicated by arrow 535. The complete retraction of arcuate tunneling needle 162 is indicated by indicator finger 284 of indicator 166. At this stage, suture 184, in doubled-over configuration, extends entirely through the bone along the arcuate path tunneled by needle 162 through the curved junction formed in the bone by needle 162 and through channel 499. At this stage, the suture 184 is securely retained in engagement with groove 164 of needle 162.

Figure 27N:
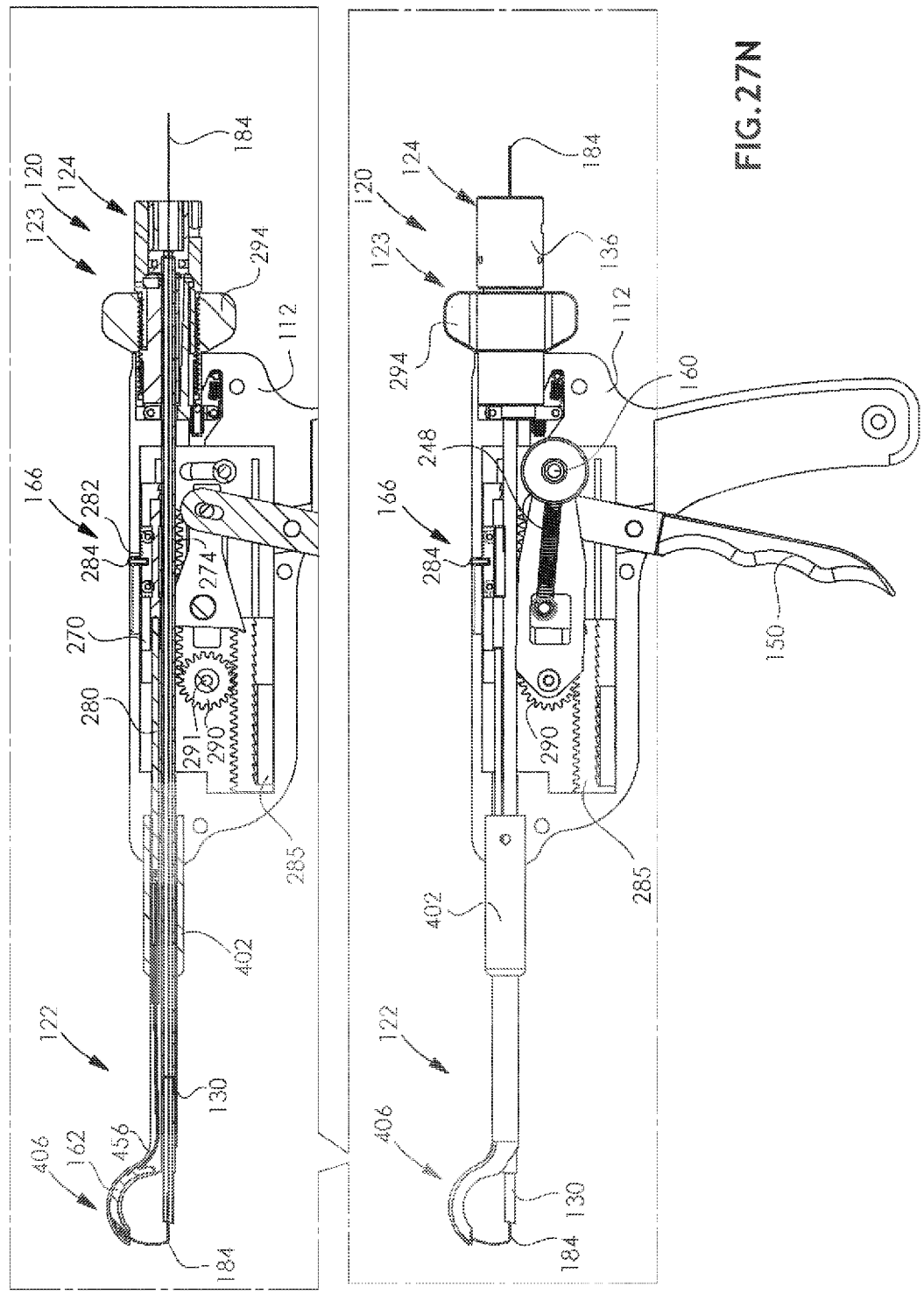
Figure 270:
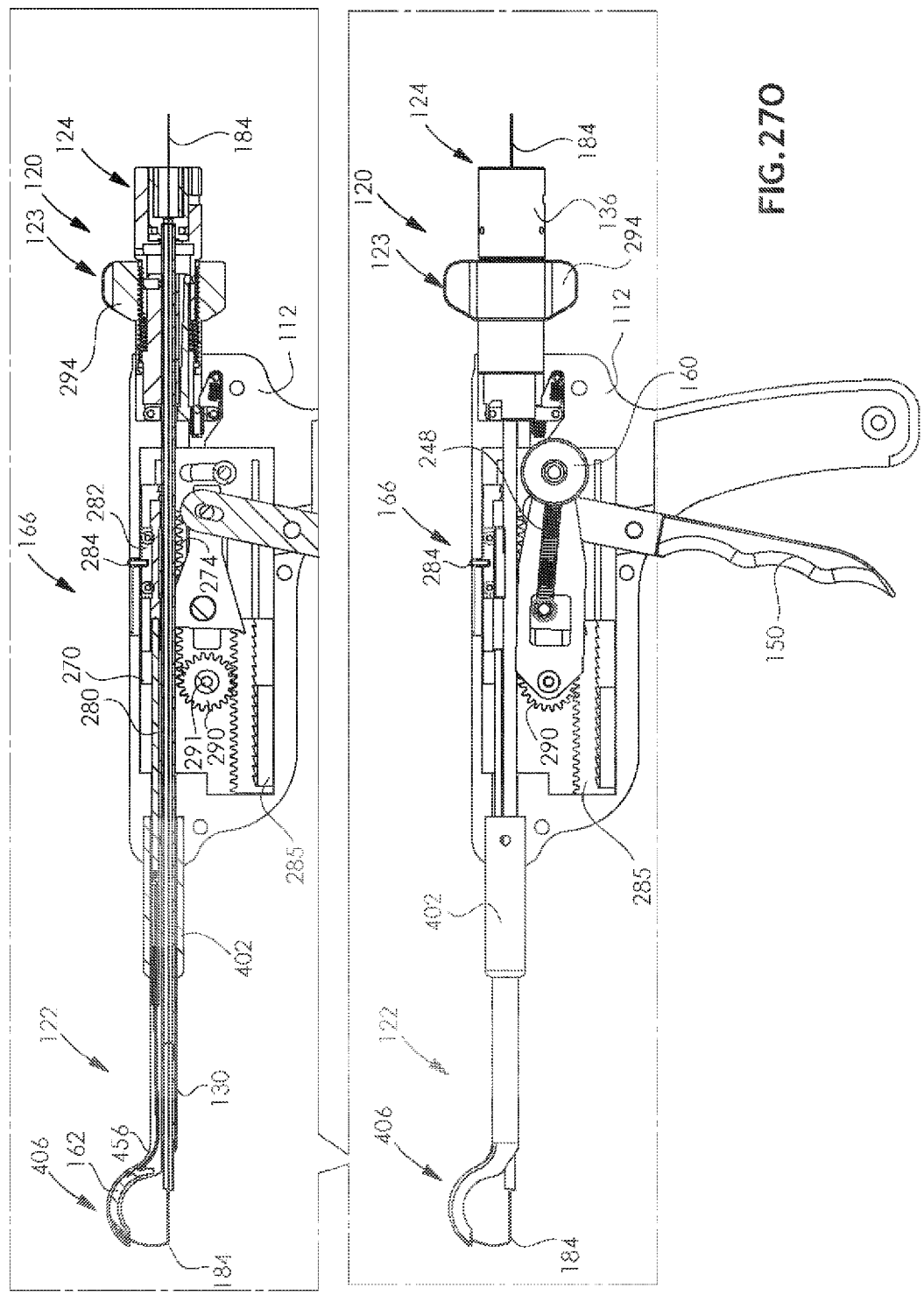
Figure 28S:
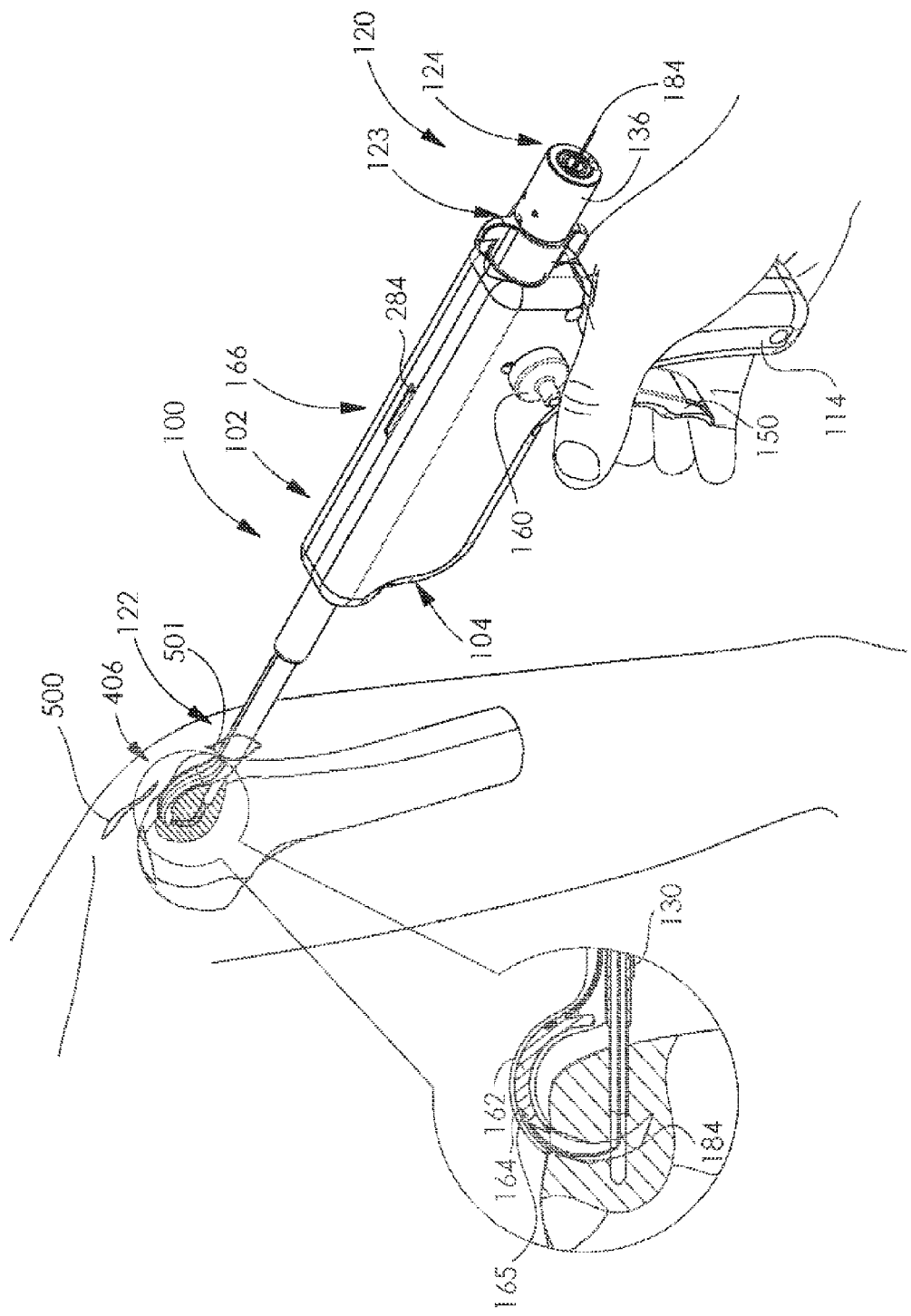

FIGS. 27N and 28S, which correspond generally to FIGS. 15A & 15B, show the arthroscopic surgical device of FIGS. 1A-26C following complete removal and disengagement of the suture cartridge assembly 170 and disengagement of the free ends of the suture 184 therefrom.

Figure 28T:
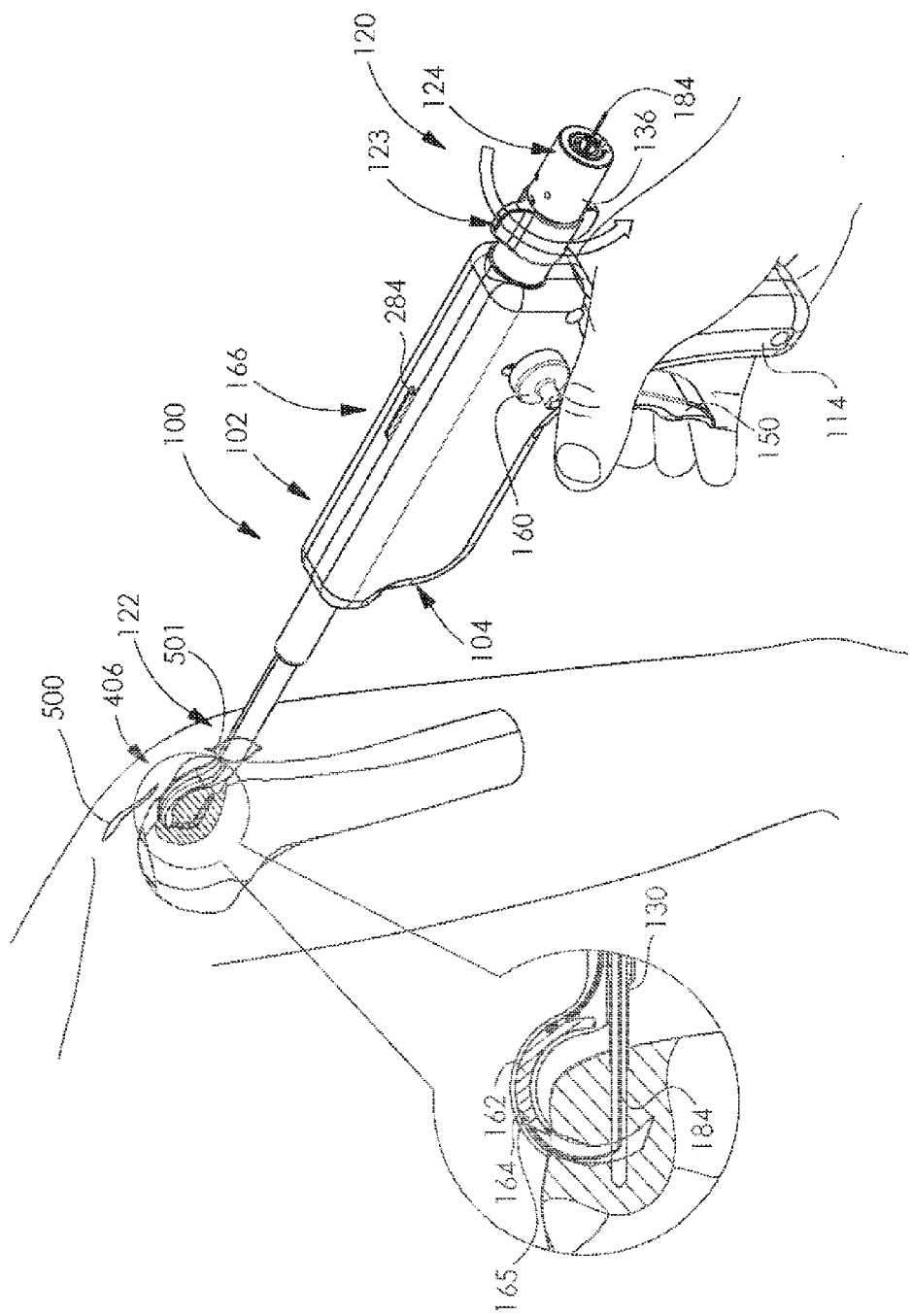

FIGS. 27O and 28T, which correspond generally to FIGS. 16A & 16B, show partial retraction of tube 130 produced by rotation of winged nut 294.

Figure 27P:
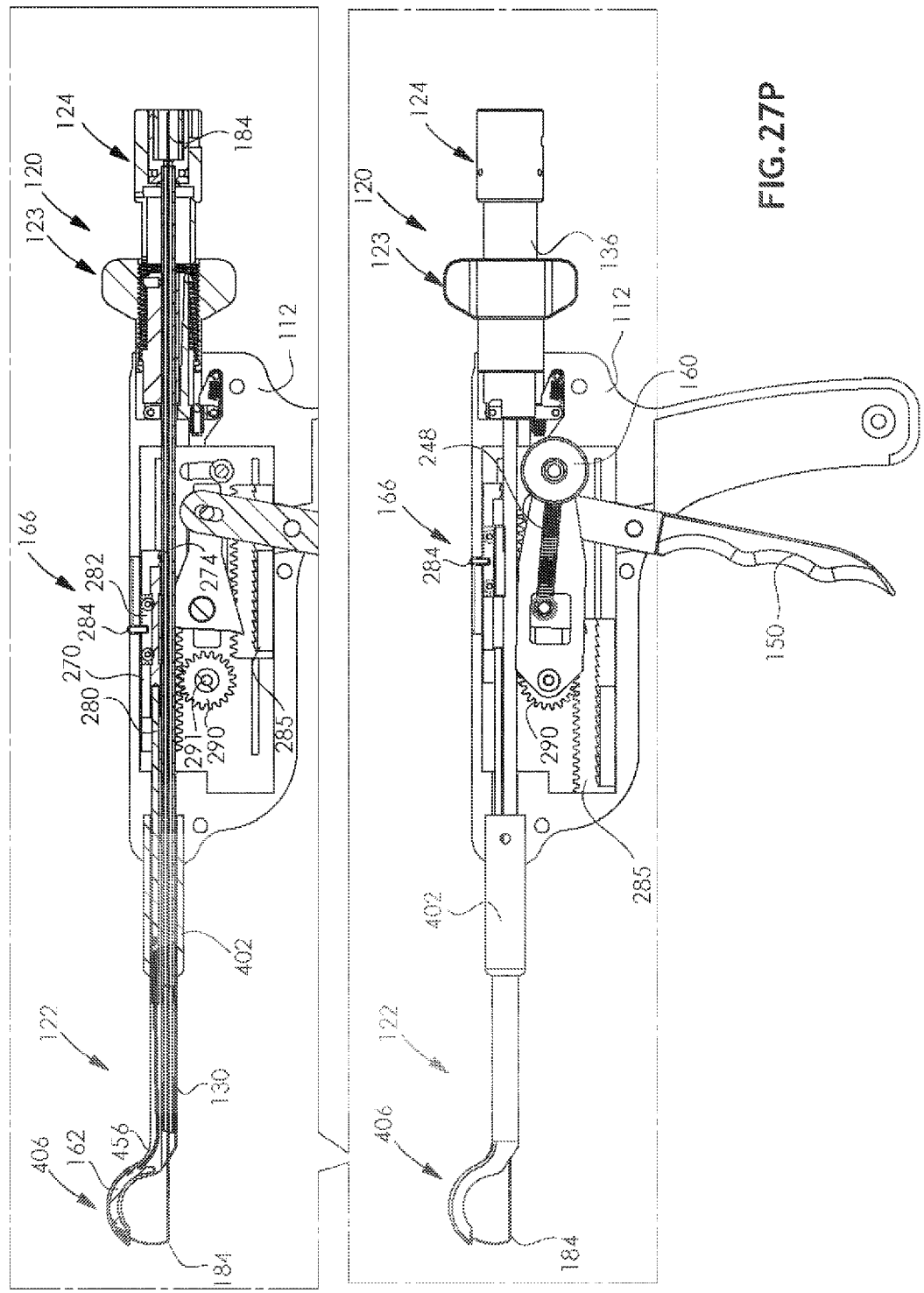
Figure 28U:
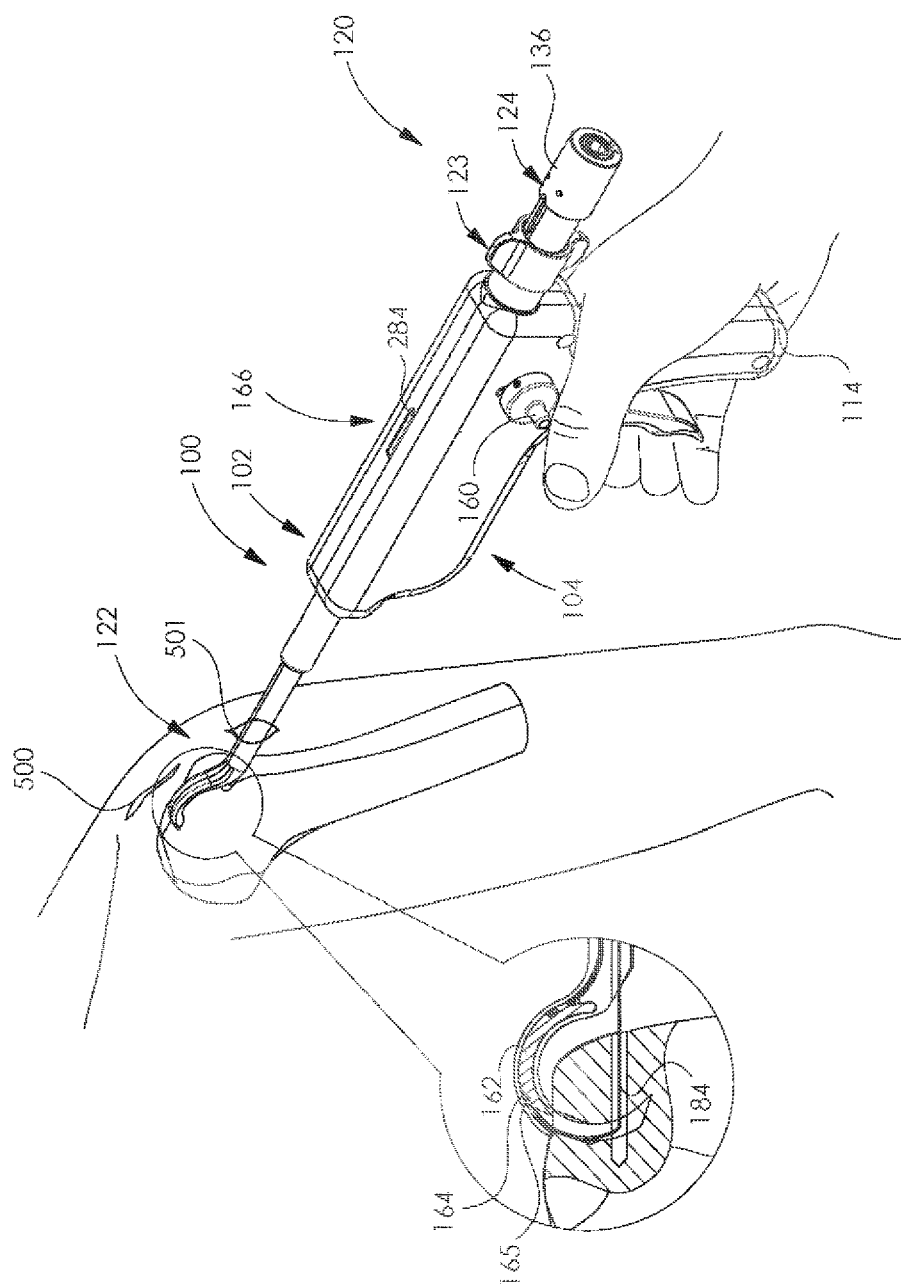

FIGS. 27P and 28U, which correspond generally to FIGS. 17A & 17B, show complete retraction of tube 130.

Figure 28V:
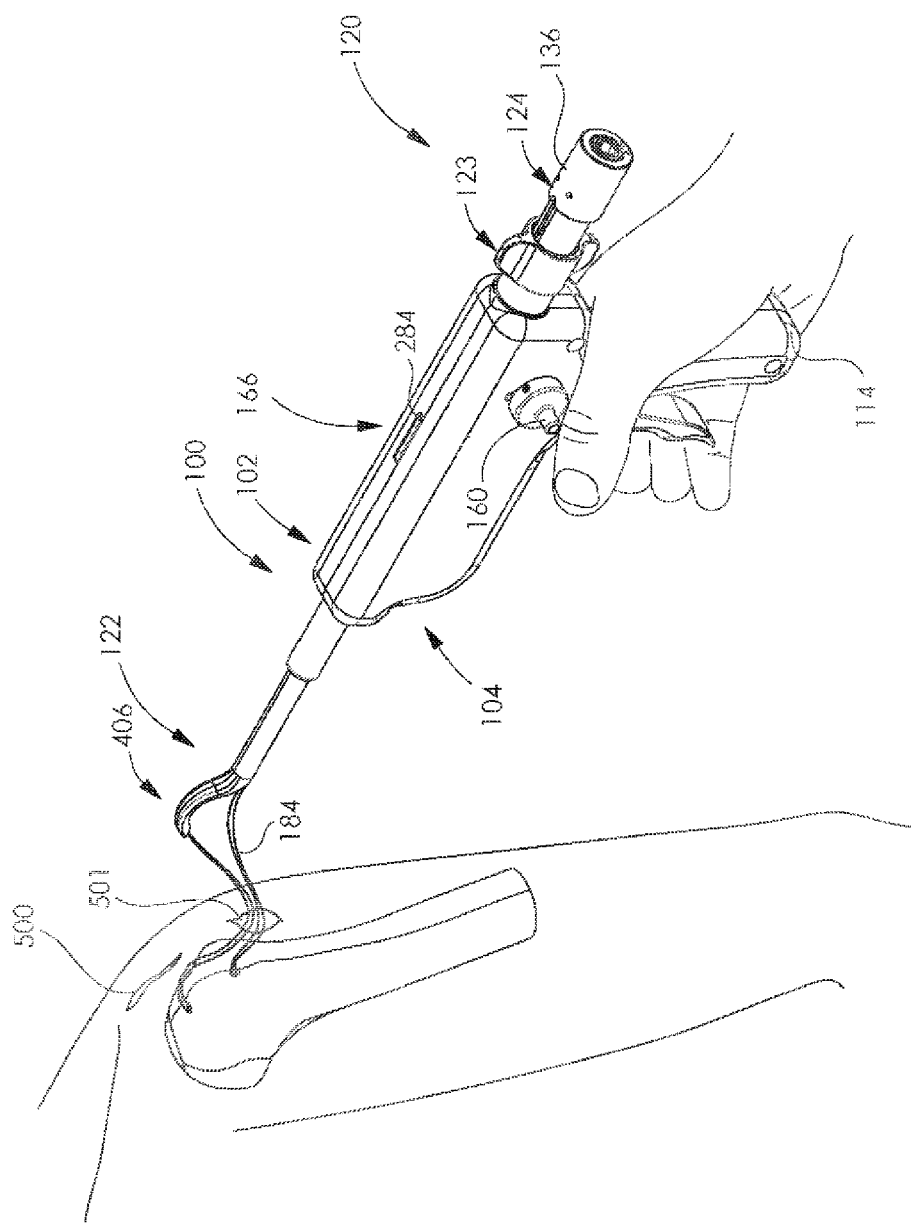

FIG. 28V shows removal of the arthroscopic surgical device from the body from the patient through incision 501, leaving the suture 184 extending through the bone.

Figure 27Q:
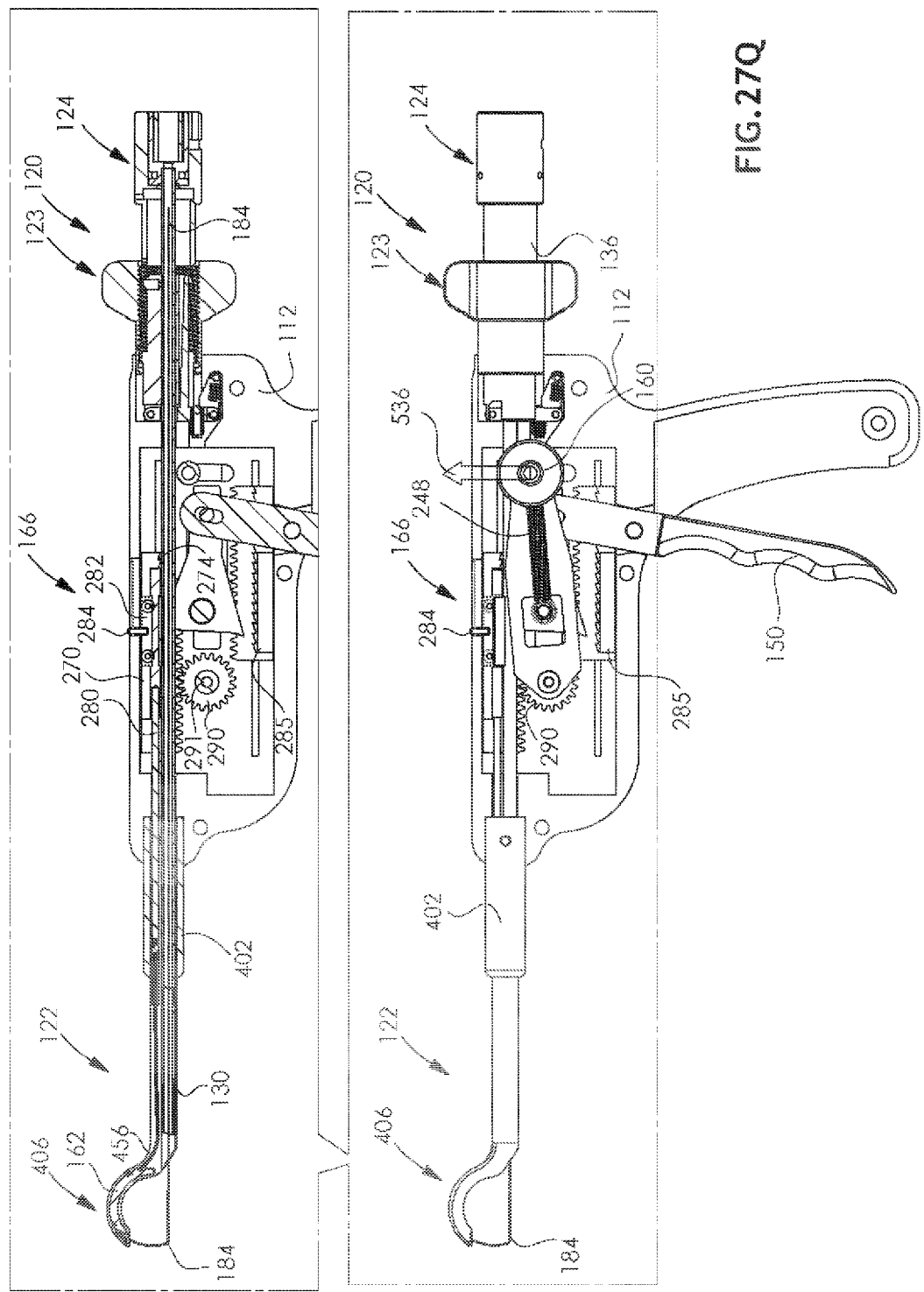
Figure 28W:
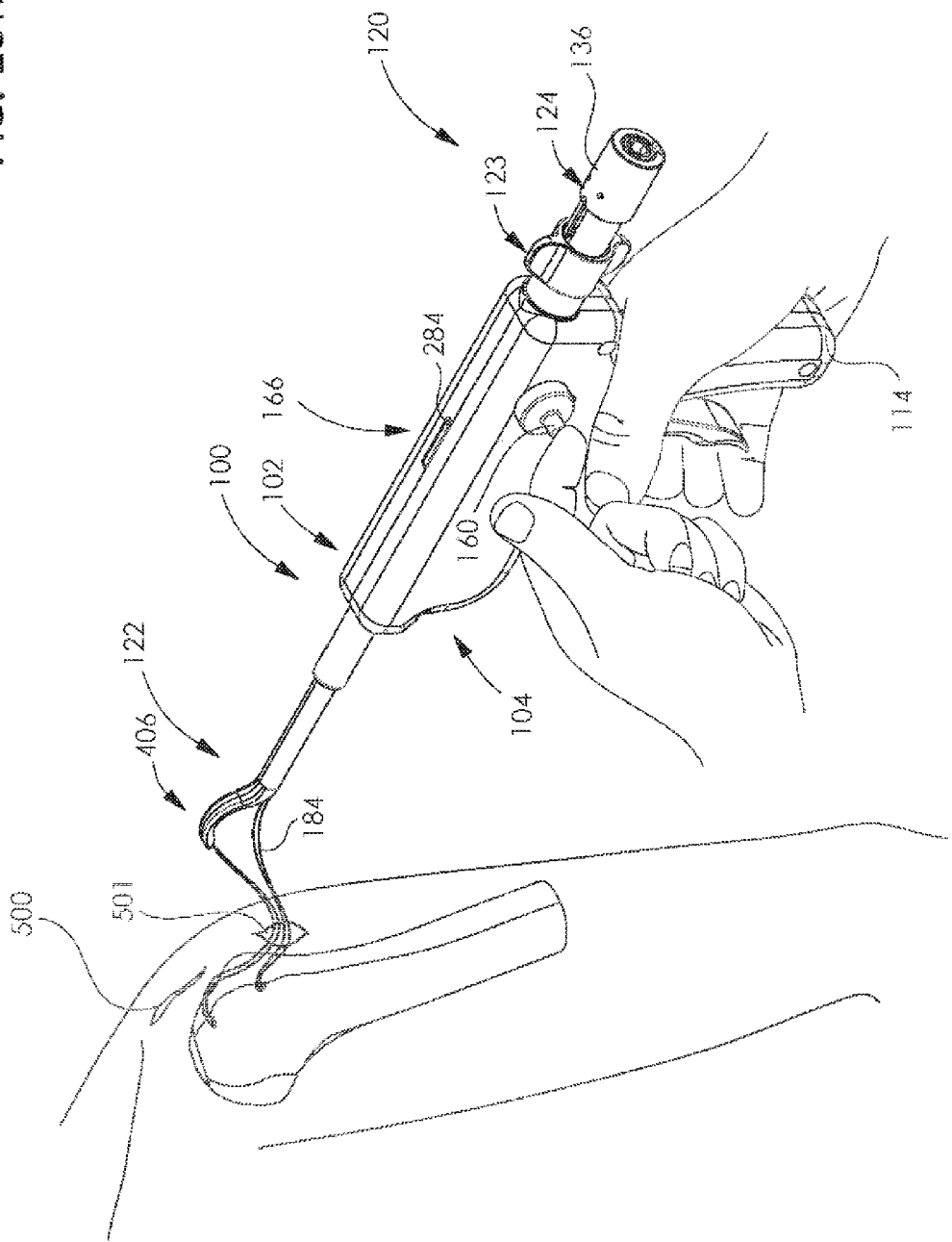

FIGS. 27Q and 28W show upward repositioning of knob 160, as indicated by an arrow 536.

Figure 27R:
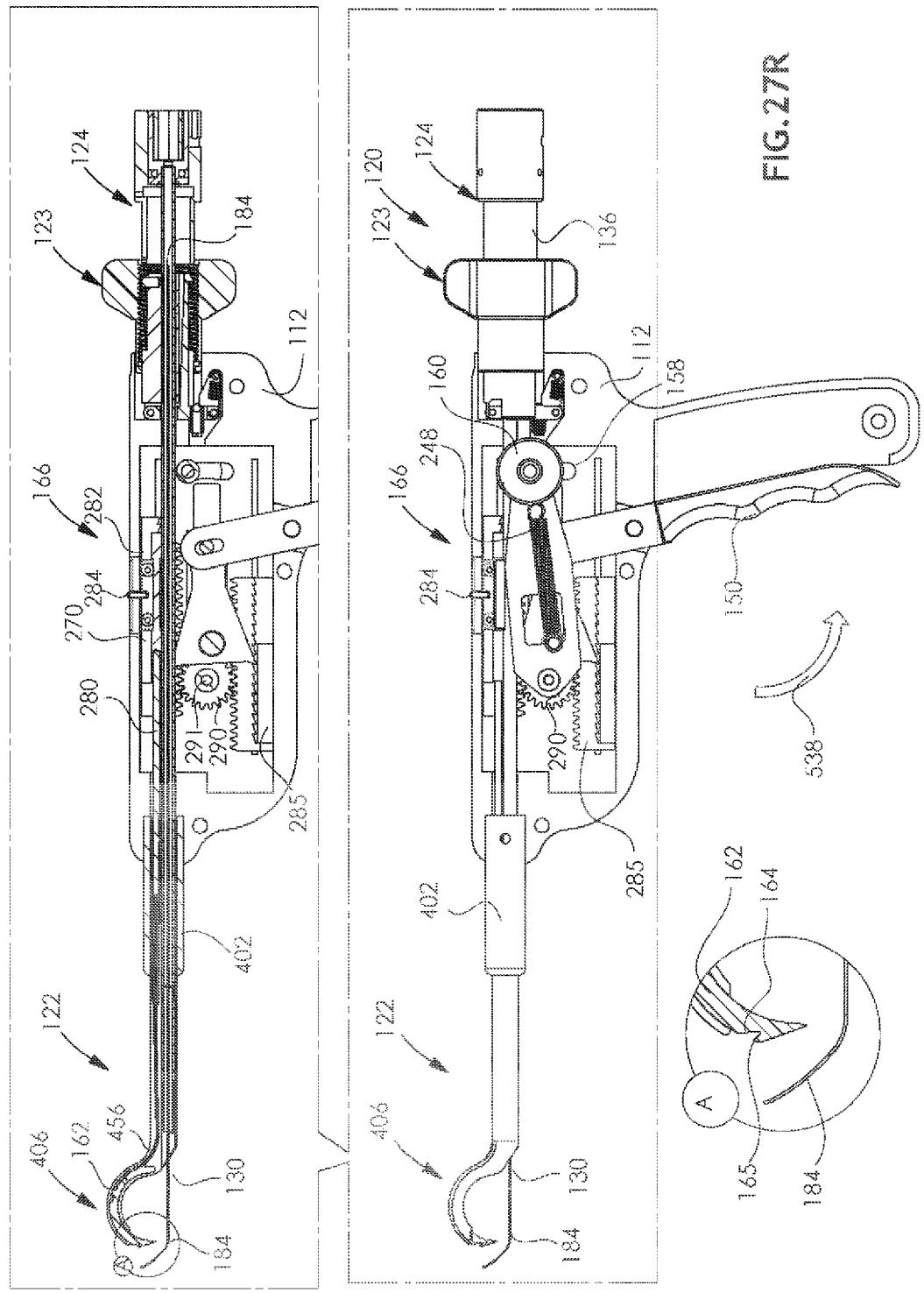
Figure 28X:
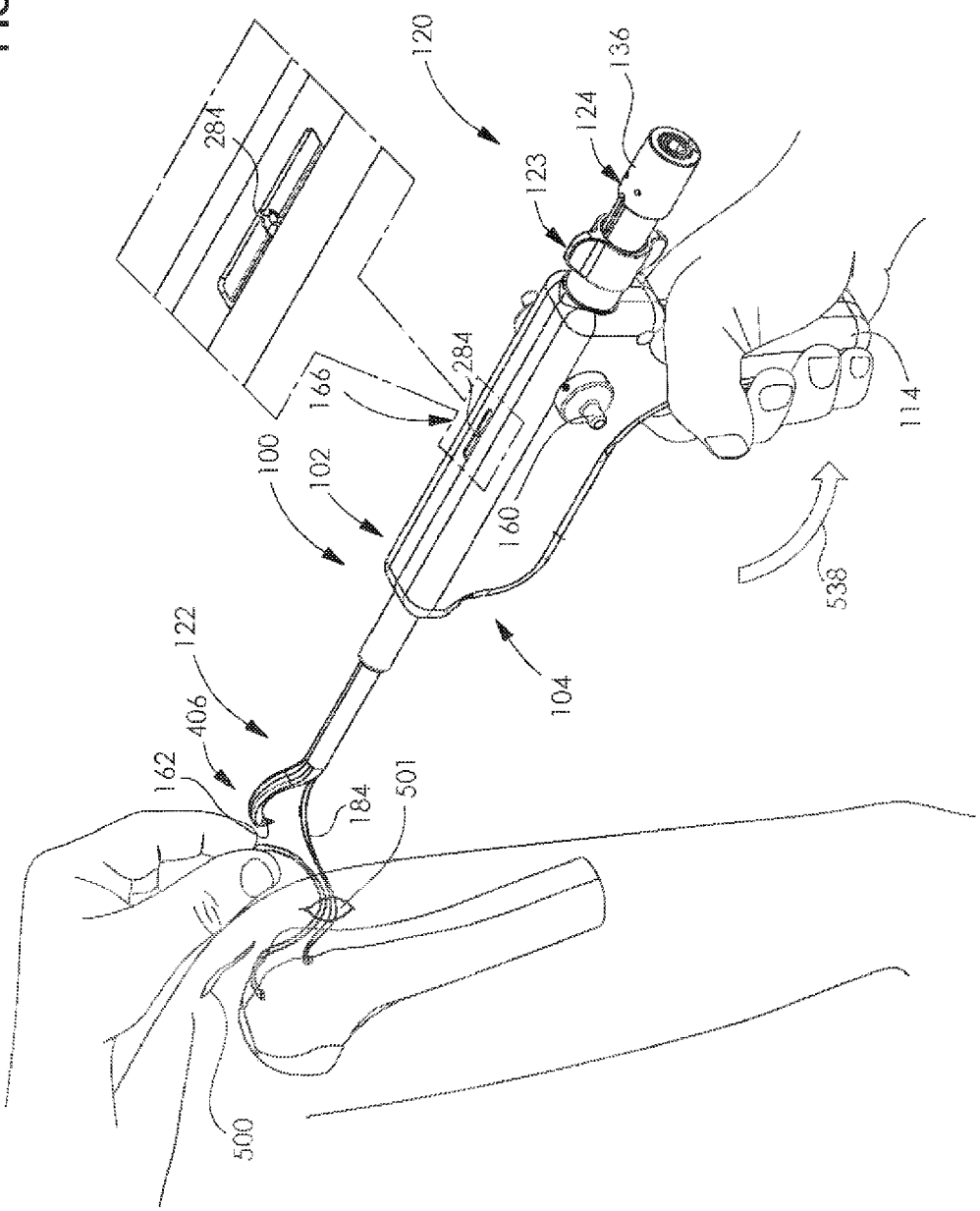

FIGS. 27R and 28X, which correspond generally to FIGS. 18A & 18B, show detachment of the suture 184 from arcuate tunneling needle 162 following extension thereof in response to further squeezing of handle 150, as indicated by an arrow 538.

It is appreciated that following detachment of folded over portion of suture 184 from needle 162 free ends of suture 184 are pulled through working channel assembly 124. As noted above, it is appreciated that free ends of suture 184 remain outside of incision 501 before, during and after the insertion procedure described above with reference to FIGS. 27A-27R and 28A-28X.

It will be appreciated by persons skilled in the art that the present invention is not limited by what has been particularly shown and described hereinabove. Rather the scope of the present invention includes both combinations and sub-combinations of the various features described hereinabove as well as modifications thereof which would occur to persons skilled in the art upon reading the foregoing description and which are not in the prior art.

The invention claimed is:

1. An arthroscopic bone channel forming and suturing system comprising:
   a punch configured to form a first generally straight channel in a bone;
   a drill configured to form a second generally straight channel in said bone, said second generally straight channel not intersecting said first generally straight channel;
   a curved needle configured to be insertable into said first generally straight channel;
   a needle driving assembly configured to manipulate said curved needle to form a curved junction between said first generally straight channel and said second generally straight channel; and
   a suture assembly configured to insert a suture to a suture pick-up location via said second generally straight channel in said bone,
   said curved needle being configured to pull said suture from said suture pick up location and through said junction and said first generally straight channel.

2. An arthroscopic bone channel forming and suturing system according to claim 1 and wherein said curved needle has a radius of curvature which is generally equal to or greater than a length of said first generally straight channel.

3. An arthroscopic bone channeling and suturing system comprising: a punch configured to form a first channel in a bone; a straight drill extending through a straight working channel and being adapted to form a second channel and to insert said working channel in said straight channel in said bone; a needle driving assembly configured to insert a tunneling needle into said first channel; and a suture assembly configured to insert a suture through said working channel and through said second channel in said bone to a suture pick-up location, said needle driving assembly being configured to retract said tunneling needle together with said suture from said suture pick-up location though said first channel, wherein said suture assembly comprises: a pair of forward arms; and said suture looped over said pair of forward arms.

4. An arthroscopic bone channeling and suturing system according to claim 3 and wherein said drill is removable from said working channel to allow insertion of said suture assembly into said working channel.

5. An arthroscopic bone channeling and suturing system according to claim 3 and wherein said drill is formed with a drill bit configuration at a forward end thereof.

6. An arthroscopic bone channeling and suturing system according to claim 3 and wherein said needle driving assembly is configured to drive said tunneling needle through said bone from said first channel to said suture pick-up location.

7. An arthroscopic bone channeling and suturing system according to claim 3 and wherein said tunneling needle includes a suture engagement groove configured to retain said suture and pull said suture from said suture pick-up location through said first channel.

8. An arthroscopic bone channeling and suturing system according to claim 7 and also comprising a suture tensioning assembly and wherein said suture is configured to slide into engagement with said suture engagement groove by tension provided by said tensioning assembly.

* * * * *